(12) United States Patent
Holmgren et al.

(10) Patent No.: US 11,801,262 B2
(45) Date of Patent: *Oct. 31, 2023

(54) ANTIBIOTIC COMPOSITIONS

(71) Applicant: Thioredoxin Systems AB, Rorgängargatan (SE)

(72) Inventors: Arne Holmgren, Sollentuna (SE); Jun Lu, Chongqing (CN); Lili Zou, Yichang (CN)

(73) Assignee: Thioredoxin Systems AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/876,592

(22) Filed: May 18, 2020

(65) Prior Publication Data

US 2020/0281967 A1 Sep. 10, 2020

Related U.S. Application Data

(63) Continuation of application No. 15/832,045, filed on Dec. 5, 2017, now Pat. No. 10,653,717.

(60) Provisional application No. 62/430,101, filed on Dec. 5, 2016.

(51) Int. Cl.
| | | |
|---|---|---|
| *A61K 33/04* | (2006.01) | |
| *A61P 31/04* | (2006.01) | |
| *A61P 31/02* | (2006.01) | |
| *A61K 33/38* | (2006.01) | |
| *A61K 9/00* | (2006.01) | |
| *A61L 24/00* | (2006.01) | |
| *A61L 24/02* | (2006.01) | |

(52) U.S. Cl.
CPC ............ *A61K 33/04* (2013.01); *A61K 9/0014* (2013.01); *A61K 9/0056* (2013.01); *A61K 33/38* (2013.01); *A61L 24/0015* (2013.01); *A61L 24/02* (2013.01); *A61P 31/02* (2018.01); *A61P 31/04* (2018.01); *A61L 2300/104* (2013.01); *A61L 2300/406* (2013.01); *Y02A 50/30* (2018.01)

(58) Field of Classification Search
None
See application file for complete search history.

(56) References Cited

U.S. PATENT DOCUMENTS

| | | |
|---|---|---|
| 6,372,254 B1 | 4/2002 | Ting et al. |
| 7,671,211 B1 | 3/2010 | Holmgren et al. |
| 8,592,468 B2 | 11/2013 | Holmgren et al. |
| 10,058,542 B1 | 8/2018 | Holmgren et al. |
| 2006/0115440 A1 | 6/2006 | Arata |
| 2008/0319092 A1 | 12/2008 | Singh |
| 2015/0283287 A1 | 10/2015 | Agarwal et al. |

FOREIGN PATENT DOCUMENTS

| | | |
|---|---|---|
| CN | 1709243 A | 12/2005 |
| GB | 1401859 A | 7/1975 |
| JP | 2015536725 A | 12/2015 |
| KR | 20070073757 A | 7/2007 |
| WO | 2007087365 A2 | 8/2007 |
| WO | 2012030960 A1 | 3/2012 |
| WO | 2014074503 A1 | 5/2014 |
| WO | WO-2018104777 A1 | 6/2018 |

OTHER PUBLICATIONS

Cereser, et al., Quantitation of reduced and total glutathione at the femtomole level by high-performance liquid chromatography with fluorescence detection: application to red blood cells and cultured fibroblasts. Journal of Chromatography B, vol. 752, No. 1, Mar. 1, 2001.
Coppo et al., Determination of glutaredoxin enzyme activity and protein S-glutathionylation using fluorescent eosin-glutathione, Analytical Biochemistry, Elsevier, Amsterdam, NL, vol. 499, Jan. 31, 2016 (Jan. 31, 2016), pp. 24-33.
Irfan Rahman et al: Assay for quantitative determination of glutathione and glutathione disulfide levels using enzymatic recycling method, Nature Protocols, vol. 1, No. 6, Dec. 31, 2006 (Dec. 31, 2006), pp. 3159-3165.
Aslund, et al., Regulation of the OxyR transcription factor by hydrogen peroxide and the cellular thiol-disulfide status. Proc Natl Acad Sci USA 1999; 96(11):6161-6165.
Brynildsen, et al., Potentiating antibacterial activity by predictably enhancing endogenous microbial ROS production. Nature biotechnology 2013;31(2): 160-165.
Cabe, et al., Effects of selenium, alone and in combination with silver or arsenic, in rats, Neurobehavioral Toxicology, Jan. 1979;1(4): 275-278.
Favrot, et al., Mechanism of inhibition of Mycobacterium tuberculosis antigen 85 by ebselen. Nature communications 2013;4:2748.
Gustafsson, et al., Ebselen and analogs as inhibitors of Bacillus anthracis thioredoxin reductase and bactericidal antibacterials targeting *bacillus* species, *Staphylococcus aureus* and Mycobacterium tuberculosis. Biochimica et biophysica acta 2016;1860(6):1265-1271.
Harbut, M.B. et al. Auranofin exerts broad-spectrum bactericidal activities by targeting thiol-redox homeostasis, Proc Natl Acad Sci USA. 112(14): 4453-4458 (Apr. 7, 2015).
Holmgren, A., Thioredoxin and glutaredoxin systems. The Journal of biological chemistry 1989; 264(24): 13963-13966.
Holmgren, et al., Thioredoxin and thioredoxin reductase. Methods Enzymol 1995;252:199-208.
Keren, et al., Killing by bactericidal antibiotics does not depend on reactive oxygen species. Science 2013;339(6124): 1213-1216.
Kohanski, et al. A common mechanism of cellular death induced by bactericidal antibiotics. Cell. Sep. 7, 2007;130(5):797-810.
Lewis, K. Platforms for antibiotic discovery. Nature Reviews. Drug Discovery. 2013; 12(5):371-387.
Lieberman, et al., High-throughput screening using the differential radial capillary action of ligand assay identifies ebselen as an inhibitor of diguanylate cyclases. ACS chemical biology 2014;9(1):183-192.

(Continued)

*Primary Examiner* — Robert A Wax
*Assistant Examiner* — Quanglong N Truong
(74) *Attorney, Agent, or Firm* — Greenberg Traurig, LLP

(57) ABSTRACT

Disclosed herein are antibiotic compositions, for example compositions that comprise a metal-containing agent and an organoselenium agent, and uses thereof.

19 Claims, 11 Drawing Sheets

(56) References Cited

OTHER PUBLICATIONS

Lillig, et al., Thioredoxin and related molecules-from biology to health and disease. Antioxid Redox Signal 2007;9(1):25-47.
Liu, et al., Cell death from antibiotics without the involvement of reactive oxygen species. Science 2013; 339(6124):1210-1213.
Lu, et al., Ebsulfur is a benzisothiazolone cytocidal inhibitor targeting the trypanothione reductase of Trypanosoma brucei. The Journal of biological chemistry 2013;288(38):27456-27468.
Lu, et al., Inhibition of bacterial thioredoxin reductase: an antibiotic mechanism targeting bacteria lacking glutathione. FASEB journal: official publication of the Federation of American Societies for Experimental Biology 2013;27(4):1394-1403.
Lu, et al., Selenoproteins. The Journal of biological chemistry 2009;284(2):723-727.
Lu, et al., The thioredoxin antioxidant system. Free radical biology & medicine 2014;66:75-87.
Martin, JL., Thioredoxin—a fold for all reasons. Structure 1995; 3(3):245-250.
Morones-Ramirez, et al., Silver enhances antibiotic activity against gram-negative bacteria. Science translational medicine 2013; 5(190): 190ra181.
Nozawa, et al., Susceptibility of methicillin-resistant *Staphylococcus aureus* to the selenium-containing compound 2-phenyl-1,2-benzoisoselenazol-3(2H)-one (PZ51). Antimicrobial agents and chemotherapy 1989;33(8):1388-1390.
Papp, et al., From selenium to selenoproteins: synthesis, identity, and their role in human health. Antioxid Redox Signal 2007;9(7):775-806.

PCT/IB2017/001615 International Search Report and Written Opinion dated Apr. 3, 2018.
Prinz, et al. The Role of the Thioredoxin and Glutaredoxin Pathways in Reducing Protein Disulfide Bonds in the *Escherichia coli* Cytoplasm. J Biol Chem. 1997; 272(25):15661-7.
Ritz, et al., Roles of thiol-redox pathways in bacteria. Annual review of microbiology 2001; 55:21-48.
Russell, et al., Antimicrobial activity and action of silver. Progress in medicinal chemistry 1994; 31:351-370.
Stewart, et al., Disulfide bond formation in the *Escherichia coli* cytoplasm: an in vivo role reversal for the thioredoxins. The EMBO journal 1998;17(19):5543-5550.
Thangamani, et al., Repurposing ebselen for treatment of multidrug-resistant staphylococcal infections. Scientific Reports, Jun. 2015; 5(1):XP055460169.
Tran, et al., Organoselenium coating on cellulose inhibits the formation of biofilms by pseudomonas aeruginosa and *Staphylococcus aureus*. Applied and environmental microbiology, Jun. 2009; 75(11):3586-3592.
Vlamis-Gardikas, et al., Characterization of *Escherichia coli* null mutants for glutaredoxin 2. The Journal of biological chemistry 2002;277(13): 10861-10868.
Walsh, C., Where will new antibiotics come from? Nat Rev Microbiol 2003;1(1):65-70.
Wilkinson, et al., Silver and nanoparticles of silver in wound dressings: a review of efficacy and safety. Journal of wound care 2011;20(11):543-549.
Zhao, et al., A novel antioxidant mechanism of ebselen involving ebselen diselenide, a substrate of mammalian thioredoxin and thioredoxin reductase. Journal of Biological Chemistry 2002;277(42):39456-39462.
Zou, et al., Synergistic antibacterial effect of silver and ebselen against multidrug-resistant gram-negative bacterial infections, EMBO Molecular Medicine, Jul. 2017; 9(8): 1165-1178.

1: Control
2: 5 μM Ag
3: 20 μM Ebselen
4: 40 μM Ebselen
5: 80 μM Ebselen
6: 5 μM Ag + 20 μM Ebselen
7: 5 μM Ag + 40 μM Ebselen
8: 5 μM Ag + 80 μM Ebselen

1    Control
2    Ebselen (25 mg/Kg body weight)
3    AgNO$_3$ (6 mg/Kg body weight)
4    AgNO$_3$ + Ebselen (6 + 25 mg/Kg body weight)

ANTIBIOTIC COMPOSITIONS

CROSS-REFERENCE

This application is a continuation of U.S. application Ser. No. 15/832,045 filed Dec. 5, 2017, now U.S. Pat. No. 10,653,717 issued May 19, 2020, which claims the benefit of U.S. Provisional Application No. 62/430,101 filed Dec. 5, 2016, which is incorporated herein by reference in its entirety.

BACKGROUND

Antibiotic resistance has become a great challenge all over the world. Gram-negative bacteria present a major threat to human life and medicine, with almost no antibiotics left for treatment making it urgent to find new principles and mechanisms. A concerted focus since the 1990s on tackling rising multidrug-resistant (MDR) Gram-positive bacteria within US and European healthcare systems appears to have been instrumental in stimulating the relatively large numbers of products targeting Gram-positive bacteria in recent years. The emergence of MDR Gram-negative bacteria presents a great threat to human life and is a challenge for modern medicine.

BRIEF SUMMARY

In some cases, the present disclosure provides an antibiotic composition, wherein the antibiotic composition comprises: a silver-containing agent; and an organoselenium agent. In some instances, the silver-containing agent can comprise a silver ion. In some instances, the silver-containing agent can comprise silver nitrate. In some instances, the silver-containing agent can comprise silver dihydrogen citrate. The sliver-containing agent can be provided as silver ions, silver nitrate and/or silver dihydrogen citrate. In some instances, the organoselenium agent can comprise a selenazol compound. In some instances, the organoselenium agent can comprise a benzoisoselenazol-3(2H)-one compound. In some instances, the organoselenium agent can comprise an ebselen. The organoselenium compound can comprise a selenazol compound, a benzoisoselenazol-3(2H)-one compound, and/or an ebselen. In some instances, the antibiotic composition can be in a dosage form of liquid. In some instances, the antibiotic composition can be in a dosage form of a solution or a suspension. In some instances, a concentration of the silver-containing agent in the antibiotic composition can be about 0.5 to 50 µM, about 1 to 25 µM, or about 1 to 10 µM. In some instances, a concentration of the silver-containing agent in the antibiotic composition can be about 5 µM. In some instances, a concentration of the organoselenium agent in the antibiotic composition can be about 4 to 25 µM, about 30 to 200 µM, about 30 to 150 µM, or about 30 to 100 µM. In some instances, a concentration of the organoselenium agent in the antibiotic composition can be about 40 µM or about 80 µM. In some instances, the silver-containing agent to the organoselenium agent or the reverse can be a molar ratio of about 1:2 to about 1:20, for example about 1:4, 1:8, or 1:16. In some instances, the antibiotic composition exhibits an $IC_{50}$ value of about 10-100 nM to one or more Gram-negative bacteria. In some instances, the antibiotic composition exhibits an $IC_{50}$ value of about 10-100 nM to one or more Gram-positive bacteria. In some instances, the antibiotic composition exhibits an $IC_{50}$ value of about 50 nM or lower to one or more Gram-negative bacteria. In some instances, the one or more Gram-negative bacteria can comprise K. pneumonia, A. baumannii, P. aeruginosa, E. cloacae, E. coli, or any combination thereof. In some instances, the antibiotic composition can comprise $AgNO_3$ and ebselen. In some instances, the antibiotic composition can comprise 5 µM of $AgNO_3$ and 4 µM of ebselen in a liquid dosage form. In some instances, the antibiotic composition can comprise 5 µM of $AgNO_3$ and 20 µM of ebselen in a liquid dosage form. In some instances, the antibiotic composition can comprise 5 µM of $AgNO_3$ and 40 µM of ebselen in a liquid dosage form. In some instances, the antibiotic composition can comprise 5 µM of $AgNO_3$ and 80 µM of ebselen in a liquid dosage form.

In some cases, the present disclosure provides a pharmaceutical formulation that can comprise the antibiotic composition disclosed herein. In some instances, the pharmaceutical formulation can further comprise an excipient disclosed herein.

In some cases, the present disclosure provides a method of inhibiting or killing one or more bacteria, comprising contacting the antibiotic composition disclosed herein with the one or more bacteria. In some cases, the present disclosure provides a method of treating a bacterial infection, comprising contacting the antibiotic composition disclosed herein with the bacterial infection. In some instances, the one or more bacteria comprise one or more Gram-negative bacteria. In some instances, the one or more bacteria comprise one or more Gram-positive bacteria. In some instances, the one or more bacteria comprise one or more multidrug-resistant bacteria. In some instances, the one or more bacteria comprise one or more multidrug-resistance Gram-negative bacteria. In some instances, the one or more bacteria can comprise K. pneumonia, A. baumannii, P. aeruginosa, E. cloacae, E. coli, or any combination thereof. In some instances, the bacterial infection or one or more bacteria can be on a surface. In some instances, the bacterial infection or one or more bacteria can be in a mammal. In some instances, the bacterial infection or one or more bacteria can be in a human. In some instances, the contacting can be by injection, for example intravenous or subcutaneous injection. In some instances, the contacting can be by topical application. In some instances, the contacting can be by oral administration. In some instances, the contacting lasts for at least about: 1 minute, 2 minute, 3 minutes, 4 minutes, 5 minutes, 10 minutes, 20 minutes, 30 minute, 40 minutes, 50 minutes, 1 hour, 2 hours, 3 hours, 4 hours, 5 hours, 6 hours, 7 hour, 8 hours, 9 hours, 10 hours, 11 hours, 12 hours, 18 hours, one day, two days, three days, four days, five days, six days, one week, or one month. In some instances, the contacting occurs 1, 2, 3, 4, 5, 6, 7, or 8 times hourly or daily. In some instances, the contacting occurs about every 3, 4, 5, 6, 7, 8, 9, 10, 11, or 12 minutes or hours daily. In some instances, the antibiotic composition can be in a single unit dose. In some instances, the amount of the organoselenium agent contacted with the bacterial infection or one or more bacteria can be about 10 to 100 mg, about 10 to 50 mg, or about 20 to 30 mg, for example about 25 mg, per dosage. In some instances, an amount of the silver contacted with the bacterial infection or one or more bacteria can be about 1 to 20 mg, about 1 to 10 mg, or about 5 to 7 mg, for example about 6 mg, per dosage.

In some cases, the present disclosure provides a method of making an antibiotic composition, comprising mixing a silver-containing agent and an organoselenium agent. In some instances, the mixing can be conducted in a liquid. In some instances, the mixing can comprise adding the silver-containing agent to a liquid that can comprise the organoselenium agent. In some instances, the mixing can comprise adding the organoselenium agent to a liquid that can comprise the silver-containing agent.

BRIEF DESCRIPTION OF THE DRAWINGS

FIG. 1A is a line chart showing synergistic effect of ebselen with silver nitrate (AgNO3) in combination on the growth of E. coli. E. coli DHB4 overnight cultures were diluted 1:1000 into 100 µl of LB medium in 96 micro-well plates, and treated by 100 µl serial dilutions of ebselen and AgNO3 in combination for 16 h, and cell viability was determined by measuring $OD_{600\ nm}$. $Ag^+$ alone inhibited E. coli growth with a minimal inhibition concentration (MIC) of 42 µM after 16 h treatment, while 2 µM ebselen dramatically decreased the MIC of $Ag^+$ to 4.2 µM (p=0.000028<0.001). FIG. 1B is a line chart showing effects of ebselen with AgNO3 in combination on the growth of HeLa cells. HeLa cells were treated with serial concentrations of ebselen and AgNO3 for 24 h, and cell toxicity was detected by MTT assay. 5.0 µM $Ag^+$ and 2.5 µM ebselen in combination showed no synergistic toxicity on human HeLa cells (p=0.98>0.05). In FIGS. 1A and 1B, data are presented as means±s. d. of three independent experiments. *: p<0.05, : p<0.01, *: p<0.001 (t-test).

FIG. 2A is a line chart showing cell viability was represented by measuring $OD_{600\ nm}$. The growth curves showed a synergistic bacteriostatic effect of Ag+ with ebselen in combination in LB medium. Five µM Ag+ and 40 µM ebselen in combination inhibited E. coli growth 480 min post-treatment (p=0.0075<0.01). FIG. 2B is a line chart showing changes of colony forming units of E. coli DHB4 on LB plates 0, 10, 60, 120, and 240 min post-treatment. The synergistic bactericidal effect of 5 µM Ag+ and 80 µM ebselen in combination was confirmed by the colony formation assay on LB-agar plates. Five µM Ag+ and 80 µM ebselen in combination killed majority E. coli 60 min post-treatment (p=0.00021<0.001). FIG. 2C is a group of FACS plots of propidium iodide (PI) stained E. coli DHB4, and FIG. 2D is a bar chart showing mean values±s. d. (D) of PI stained E. coli DHB4. Five µM Ag+ and 20 µM ebselen in combination enhanced the frequency of propidium iodide (PI) staining (p=0.00083<0.001). In FIGS. 2A to 2C, data are presented as means±s. d. of three independent experiments. *: p<0.05, : p<0.01, *: p<0.001 (t-test).

FIG. 3A is a bar chart showing TrxR activities were assayed using DTNB reduction in the presence of Trx in E. coli extracts, 50 mM Tris·HCl (pH 7.5), 200 µM NADPH, 1 mM EDTA, 1 mM DTNB, in the presence of 100 nM E. coli TrxR. Five µM $Ag^+$ and 20 µM ebselen in combination resulted in a dramatic loss of TrxR activities (p=0.00018<0.001). FIG. 3B is a bar chart showing Trx activities were assayed using DTNB reduction in the presence of Trx in E. coli extracts, 50 mM Tris·HCl (pH 7.5), 200 µM NADPH, 1 mM EDTA, 1 mM DTNB, 5 µM E. coli Trx. Five µM $Ag^+$ and 20 µM ebselen in combination resulted in a dramatic loss of Trx activities (p=0.0036<0.01). FIG. 3C is a bar chart showing changes of Trx1 redox state in E. coli upon ebselen and AgNO3 treatment. E. coli were precipitated in 5% TCA and alkylated with 15 mM AMS, and the percent of reduced Trx1 were analyzed by Western blot. FIG. 3D is a group of Western blot images showing changes of Trx2 redox state in E. coli upon ebselen and AgNO3 treatment. E. coli were precipitated in 5% TCA and alkylated with 15 mM AMS, diamide oxidized Trx2 was used as a Trx2 positive control, and the percent of reduced Trx2 were analyzed by Western blot. FIG. 3E is a bar chart showing GSH amounts were measured by GR-coupled DTNB reduction assay in E. coli extracts, 50 mM Tris·HCl (pH 7.5), 200 µM NADPH, 1 mM EDTA, 1 mM DTNB, 50 nM GR. Five µM $Ag^+$ and 20 µM ebselen in combination treatment depleted the functional GSH in 10 min compared with control (p=0.000021<0.001). FIG. 3F is a Western blot image showing changes of proteins S-glutathionylation in E. coli. Cells were cultured, washed, and re-suspended in lysis buffer containing 30 mM IAM. After lysed by sonication, Western blotting assay was performed with IgG2a mouse monoclonal antibody (VIROGEN, 101-A/D8) for glutathione-protein complexes. In FIGS. 3A, 3B, and 3E, data are presented as means±s. d. of three independent experiments. *: p<0.05, : p<0.01, *: p<0.001 (t-test).

FIG. 4A is a line chart showing inhibition of E. coli TrxR by AgNO3. Pure recombinant 100 nM TrxR, and 5 µM Trx mixture were incubated with AgNO3 solution in the presence of 200 µM NADPH, and then their activities were detected by DTNB reduction assay. FIG. 4B is a fluorescent spectra of a complex between reduced E. coli 10 µM Trx1 with AgNO3. Reduced 10 µM E. coli Trx1 protein was incubated with a serial concentration of AgNO3 solution and the fluorescent spectra was detected with an excitation wavelength at 280 nm. Oxidized Trx1 (Trx-$S_2$) was used as a control. FIG. 4C is a bar chart showing inhibition of Trx by AgNO3. After the treatment described in (B), Trx activity was assayed by a DTNB method in the presence of E. coli Trx1. FIG. 4D is a bar chart showing inhibition reversibility of E. coli Trx1 by AgNO3. Silver-inhibited E. coli Trx1 was passed through a desalting column to remove small molecules and then Trx activity was measured. E. coli Trx1 without the inhibition was used as a control. The inhibition of Trx1 by $Ag^+$ was irreversible since the Trx1 activity was not recovered after desalting (p=0.00021<0.001). Data are presented as means±s. d. of three independent experiments. *: p<0.05, : p<0.01, *: p<0.001 (t-test).

FIG. 5A shows FACS histograms of $H_2$DCF-DA-stained E. coli. FIG. 5B is a bar chart of mean MFI±s. d. of $H_2$DCF-DA-stained E. coli. E. coli DHB4 grown to $OD_{600\ nm}$ of 0.4 were treated by 20 µM ebselen and 5 µM AgNO3. ROS level was detected by flow cytometry (CyAn adp, Beckman coulter). Treatment with either 5 µM $Ag^+$ or 20 µM ebselen alone did not change ROS concentrations, while the combination of 5 µM $Ag^+$ and 20 ebselen resulted in increased levels of ROS (p=0.00012<0.001). FIG. 5C is a bar chart showing detection of $H_2O_2$ using the Amplex® Red Hydrogen Peroxide/

Peroxidase Assay Kit (Invitrogen). Reactions containing 50 µM Amplex® Red reagent, 0.1 U/mL HRP and the indicated amount of $H_2O_2$ in 50 mM sodium phosphate buffer, pH 7.4, were incubated for 30 minutes at room temperature and detected with absorbance at 560 nm. Background determined for a non-$H_2O_2$ control reaction, has been subtracted from each value. The enhanced $H_2O_2$ generated by 5 µM $Ag^+$ and 20 µM ebselen treated E. coli DHB4 cells were verified (p=0.00057<0.0001). In FIGS. 5B and 5C, data are presented as means±s. d. of three independent experiments. *: p<0.05, : p<0.01, *: p<0.001 (t-test).

FIG. 6A is a line chart of E. coli CFU measurements over 36 hours in the mild mice peritonitis model. Mice were infected by intraperitoneal administration of 100 µl $1.7 \times 10^6$ E. coli ZY-1 cells. After 24 h, 12 mice per group received antibacterial treatments (25 mg ebselen/kg and 6 mg $AgNO_3$/kg body weight). 12, 24, and 36 h after treatment, the peritoneal fluid was collected for analysis of E. coli CFU (n=12 mice for each group) (p=0.0055<0.01), and data are presented as means±s. d. of three independent experiments. *: p<0.05, : p<0.01, *: p<0.001 (t-test). FIG. 6B is a line chart of E. coli CFU measurements over 96 hours in the acute mice peritonitis model. Inoculation was performed by intraperitoneal injection of 100 µl of $6.0 \times 10^6$ CFU/ml E. coli ZY-1 inoculums. After inoculation for 1 h, 10 mice per group received antibacterial treatments, and the mice were observed for 7 days to evaluate overall survival (n=10 mice for each group), and the experiment was performed duplicate.

FIG. 8A is a bar chart showing that ROS level was detected by flow cytometry (CyAnadp, Beckman coulter), and mean MFI±. s. d. of $H_2$DCF-DA-stained E. coli were detected. FIG. 8B is a bar chart showing that detection of H2O2 using the Amplex® Red Hydrogen Peroxide/Peroxidase Assay Kit (Invitrogen). Reactions containing 50 µM Amplex® Red reagent, 0.1 U/mL HRP and the indicated amount of $H_2O_2$ in 50 mM sodium phosphate buffer, pH 7.4, were incubated for 30 minutes at room temperature and detected with absorbance at 560 nm. Background determined by a non-$H_2O_2$ control reaction has been subtracted from each value. Data are presented as means±s. d. of three independent experiments. *: p<0.05, : p<0.01, *: p<0.001 (t-test).

FIG. 9A is a bar chart showing Trx activities assayed using DTNB reduction in the presence of Trx in E. coli extracts. FIG. 9B is a bar chart showing TrxR activities assayed using DTNB reduction in the presence of TrxR in E. coli extracts. FIG. 9C is a Western blot image showing the percent of reduced Trx1. E. coli DHB4 grown to $OD_{600\,nm}$ of 0.4 were treated with antibiotics and AgNO3 in combinations for 60 min, and ebselen and $AgNO_3$ in combination was used as positive control. E. coli extracts were precipitated in 5% TCA and alkylated with 15 mM AMS and the percent of reduced Trx1 was analyzed by Western blot. The means±s. d. of three independent experiments was depicted. The t-test significances were calculated between control and rest groups, and *: p<0.05, : p<0.01, *: p<0.001.

FIG. 10A is a bar chart showing total GSH amounts measured by GR-coupled DTNB reduction assay in E. coli extracts. FIG. 10B is a Western blot image showing changes in protein S-glutathionylation in E. coli. The mean s. d. of three independent experiments is depicted. The t-test significances were calculated between control and test groups, and *: p<0.05, : p<0.01, *: p<0.001.

FIG. 11A is a bar chart showing total GSH amounts were measured by GR-coupled DTNB reduction assay in E. coli extracts. FIG. 11B is a Western blot image showing changes in protein S-glutathionylation in E. coli. The means±s. d. of three independent experiments was depicted. The t-test significances were calculated between control and rest groups, and *: p<0.05, : p<0.01, *: p<0.001.

DETAILED DESCRIPTION

The disclosure herein is generally directed to antibiotic compositions comprising multiple pharmaceutically active agents (two, three, four, or more) that are useful in combination as antimicrobial therapeutics that treat and/or prevent bacterial infection by killing or inhibiting the growth of bacteria. For example, a composition that can comprise a metal-containing agent (e.g., silver ion) and an antimicrobial agent (e.g., ebselen) in synergistic combination disclosed herein targets bacterial thioredoxin and glutathione systems and is potent against bacterial infections such as those caused by Gram-negative bacteria.

An "effective amount" when used in connection with a composition or active agent disclosed herein is an amount sufficient to produce a therapeutic result in a subject in need thereof. For example a therapeutic result includes, but is not limited to, treating, preventing, ameliorating, or lessening bacterial infection and/or any symptom thereof such as inflammation, fever, cough, sneezing, nasal congestion, runny nose, sore throat, pain, nausea, vomiting, or constipation in a subject.

The term "about" means the referenced numeric indication plus or minus 15% of that referenced numeric indication.

The present disclosure shows that multidrug-resistant (MDR) Gram-negative bacteria are highly sensitive to silver and ebselen in a synergistic combination. In contrast, silver shows no synergistic toxicity with ebselen against mammalian cells. Biochemical experiments revealed that silver and ebselen caused a fast depletion of glutathione and inhibition of the thioredoxin system in bacteria. Silver ions were identified as strong inhibitors of *E. coli* thioredoxin and thioredoxin reductase, which are required for ribonucleotide reductase and DNA synthesis and defense against oxidative stress. Bactericidal efficacy of silver and ebselen causing oxidative stress was further verified in the treatment of mild and acute MDR *E. coli* peritonitis in mice. These results demonstrate that thiol-dependent redox systems in bacteria could be targeted in the design of new antibacterial drugs. Silver and ebselen act as a probe to target essential bacterial systems which might be developed for novel efficient treatments against MDR Gram-negative bacterial infections. Silver acted strongly synergistic with the selenazol drug ebselen, to combat difficult-to-treat MDR Gram-negative bacteria in the clinic, by targeting thiol-dependent antioxidant systems. The results were further proven by successfully treating mice with MDR *E. coli* caused mild or acute peritonitis. Redox system is a universal anti-oxidative system which is essential for living organism, inhibition of redox system will result in oxidative stress, which shows a novel antibacterial principle to screen and use new antibiotics.

Figure 6A:
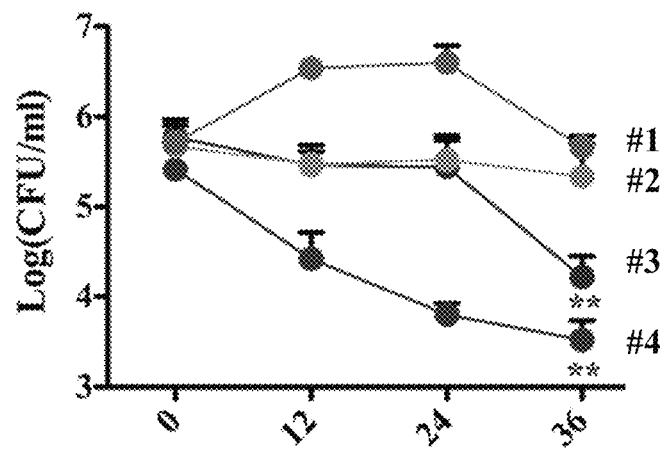
FIGS. 6A to 6B illustrate mode of action of silver and ebselen in in vivo mild and acute mice peritonitis model.
Figure 6B:
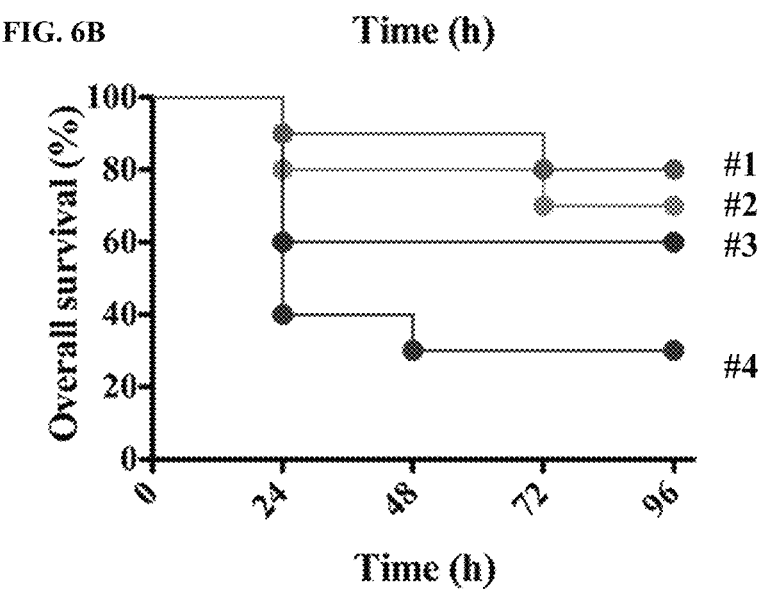

In some cases, an antibiotic composition disclosed herein kills MDR Gram-negative bacteria. In some instances, the antibiotic composition selectively targets bacterial thiol-dependent redox systems via strong bactericidal effect of silver and ebselen in synergistic combination against GSH-positive bacterial infections, particularly on MDR Gram-negative bacteria. In some instances, the silver ions are strong inhibitors of both *E. coli* Trx and TrxR, and the combination with ebselen depletes GSH and gave a steep rise in ROS generation. In some instances, the presence of ebselen improves efficacy of silver and thus decreases the antibacterial concentration of silver needed to elicit an effect, with highly significant selective toxicity on bacteria over mammalian cells. This selective toxicity facilitates the systemic medical application of silver in the treatment of MDR Gram-negative bacteria. In some instances, the synergistic bactericidal effect of $Ag^+$ with ebselen in combination is efficient against these MDR Gram-negative pathogens (Table 1). Further, results from animal experiments indicated that this antibiotic combination can be considered as a candidate for clinical trials against MDR bacteria (FIGS. 6A-6B, Table 1). Silver and ebselen together can be regarded as a probe targeting essential functions in bacteria. The experimental results presented here proposed mechanisms for the synergistic antibacterial effect of $Ag^+$ with ebselen in combination. Silver and ebselen can directly inhibit *E. coli* TrxR, and fast deplete GSH, which resulted in the elevation of ROS production to determine cell death (synopsis). Thiol-dependent redox pathways regulate various central cellular functions. Thus, $Ag^+$ with ebselen in combination can react with SH-groups in GSH, and particularly Trx and TrxR and possibly many other proteins, indicating that the inhibitory effect of $Ag^+$ with ebselen in combination may involve several cellular targets. In addition, $Ag^+$ and ebselen might target other molecules: for example, diguanylate cyclase and *M. tuberculosis* antigen 85. This may impair the development of antibiotic resistance in bacteria.

Active Agents

Disclosed herein is a combination of a metal-containing agent and an antimicrobial agent. A metal-containing agent can comprise a metal or metal ion disclosed herein. The metal-containing agent can comprise a metal ion that possesses antibiotic activity, for example silver, copper, zinc, mercury, tin, lead, bismuth, cadmium, cerium, chromium, and thallium ions. Antimicrobial metal ions of silver, gold, copper and zinc, can be considered safe for in vivo use and not substantially absorbed into the body. The antimicrobial agent can be an antibiotic such as gentamicin, kanamycine, geneticin, tetracycline, a non oragoselenum agent, or an organoselenium agent (e.g., ebselen or an analog thereof), or any antimicrobial agent described herein. In some instances, a metal-containing agent (e.g., silver) enhances the antibacterial effects of an organoselenium agent (e.g., ebselen) or certain antibiotics against Gram-negative bacteria through direct targeting the bacterial thioredoxin (Trx) system, the glutathione (GSH) system, or both. In some instances, targeting/attacking the GSH system increases efficacy of an antibiotic composition in killing one or more bacteria. In some instances, an antibiotic composition can comprise a silver agent and an antibiotic disclosed herein.

In some cases, an antibiotic composition disclosed herein can comprise a metal containing agent, either in the form of a metal atom or a metal ion unlinked or linked to another molecule via a covalent or noncovalent (e.g., ionic) linkage. Silver containing agents can include but are not limited to covalent compounds such as silver dihydrogen citrate, silver sulfadiazine and silver salts such as silver oxide, silver carbonate, silver deoxycholate, silver salicylate, silver iodide, silver nitrate, silver paraaminobenzoate, silver paraaminosalicylate, silver acetylsalicylate, silver ethylenediaminetetraacetic acid ("Ag EDTA"), silver picrate, silver protein, silver citrate, silver lactate and silver laurate. The silver agents can be covalent compounds or for example, silver salts, silver complex ions, colloidal silver, silver/zeolite composites, silver/phosphate, silver/glass particles (antimicrobial, controlled release), or any mixture thereof. In some instances, silver salts are silver chloride, silver nitrate, silver acetate, silver benzoate, silver bromate, silver chlorate, silver lactate, silver molybdate, silver nitrite, silver (I) oxide, silver perchlorate, silver permanganate, silver selenate, silver selenite, silver sulfadiazine, silver sulfate, and mixtures thereof. In some instances, silver complex ions are silver chloro complex ions, silver thiosulfato complex ions, or mixtures thereof. In some instances, colloidal silver particles are silver nanoparticles.

In some instances, the metal containing agent can comprise a metal salt. The metal salt can be a silver salt as silver nitrate, silver acetate, silver benzoate, silver carbonate, silver iodate, silver iodide, silver lactate, silver laurate, silver oxide, silver palmitate, silver protein, or silver sulfadiazine. The metal containing agent can comprise a copper ion source such as copper(II) nitrate, copper sulfate, copper perchlorate, copper acetate, tetracyan copper potassium. The metal containing agent can comprise a zinc ion source such as zinc(II) nitrate, zinc sulfate, zinc perchlorate, zinc acetate and zinc thiocyanate; such a mercury ion source as mercury perchlorate, mercury nitrate and mercury acetate. The metal containing agent can comprise a tin ion source such as tin sulfate. The metal containing agent can comprise a lead ion source such as lead sulfate and lead nitrate. The metal containing agent can comprise a bismuth ion source such as bismuth chloride and bismuth iodide. The metal containing agent can comprise a cadmium ion source such as cadmium perchlorate, cadmium sulfate, cadmium nitrate and cadmium acetate. The metal containing agent can comprise a chromium ion source such as chromium perchlorate, chromium sulfate, chromium ammonium sulfate and chromium acetate. The metal containing agent can comprise a thallium ion source such as thallium ion source as thallium perchlorate, thallium sulfate, thallium nitrate or thallium acetate.

The silver may be provided in a soluble or insoluble form, such as silver chloride, adsorbed on a support or particles selected from the group consisting of titanium oxide, magnesium oxide, aluminum oxide, silicon oxide, calcium oxide, barium oxide, calcium hydroxyapatite, chalk, natural ground or precipitated calcium carbonates, calcium magnesium carbonates, silicates, sheet silicates, zeolites, clays, bentonites and titanium oxide. Insoluble silver on a support material can be useful for topical application. The composition disclosed herein may also include an effective amount of a dispersant, such as polynaphthalenesulfonate, naphthalenesulfonate or alkyl sulfosuccinate.

In some instances, the minimal inhibitory concentration (MIC) to one or more bacteria for an antibiotic metal (e.g., silver) contained in an antibiotic composition disclosed herein can be less than about: 50 µM, 25 µM, 20 µM, 10 µM, 5 µM, 1 µM, 0.5 µM, 0.1 µM, 50 nM, 25 nM, 20 nM, 10 nM, 5 nM, or 1 nM.

Organoselenium agents are chemical compounds containing carbon-to-selenium chemical bonds. Selenium can exist with oxidation state −2, +2, +4, +6, e.g., Se (II). Organoselenium agents include but are not limited to selenols, diselenides, selenyl halides, selenides (selenoethers), selenoxides, selenones, selenenic acids, seleninic acids, perseleninic acids, selenuranes, seleniranes, selones (e.g., selenourea), selenocysteine, selenomethionine, diphenyldiselenide, benzeneselenol. In some instances, the organoselenium agent can comprise selenazol or isoselenazol compound, for example a benzoisoselenazol-3(2H)-one compound, e.g., ebselen (Chemical name: 2-phenyl-1,2-benzisoselenazol-3 (2H)-one, IUPAC name: 2-Phenyl-1,2-benzoselenazol-3-one), ebselen diselenide, or a structural analog such as those disclosed herein.

In some instances, the organoselenium agent can comprise a compound represented by the following general formula (I) or (I'):

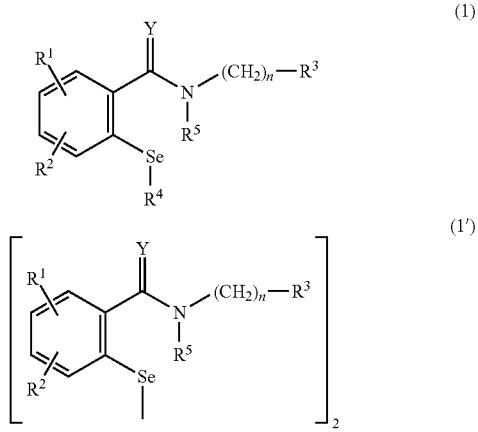

wherein $R^1$ and $R^2$ independently represent a hydrogen atom, a halogen atom, a trifluoromethyl group and the like; $R^3$ represents an aryl group, an aromatic heterocyclic group and the like; $R^4$ represents a hydrogen atom, a hydroxyl group, a —S-α-amino acid group and the like; $R^5$ represents a hydrogen atom or a $C_1$-$C_6$ alkyl group; Y represents oxygen atom or sulfur atom; n represents an integer of from 0 to 5; and the selenium atom may be oxidized, whose example includes 2-phenyl-1,2-benzisoselenazol-3(2H)-one or a ring-opened form thereof. In some instances, the organoselenium agent can comprise a compound selected from the group consisting of 2-phenyl-1,2-benziso-selenazol-3(2H)-one or a ring-opened form thereof and a physiologically acceptable salt thereof. In some instances, the organoselenium agent can comprise a substance selected from the group consisting of 2-phenyl-1,2-benziso-selenazol-3(2H)-one or a ring-opened form thereof and a physiologically acceptable salt thereof. In some instances, the organoselenium agent can comprise a substance selected from the group consisting of 2-phenyl-1,2-benziso-selenazol-3(2H)-one or a ring-opened form thereof and a physiologically acceptable salt thereof.

As the $C_1$-$C_6$ alkyl group represented by $R^1$ and $R^2$, either a straight or a branched chain alkyl group may be used, and examples include methyl group, ethyl group, n-propyl group, isopropyl group, cyclopropyl group, n-butyl group, sec-butyl group, isobutyl group, tert-butyl group, n-pentyl group, and n-hexyl group. As the $C_1$-$C_6$ alkoxyl group represented by $R^1$ and $R^2$, either a straight or a branched chain alkoxyl group may be used, and examples include methoxy group, ethoxy group, n-propoxy group, isopropoxy group, n-butoxy group, sec-butoxy group, tert-butoxy group, n-pentoxy group, and n-hexoxy group.

As the aryl group represented by $R^3$, for example, a monocyclic to a tricyclic, preferably a monocyclic or a bicyclic aryl group having 6 to 14 carbon atoms, preferably 6 to 10 carbon atoms can be used. More specifically, phenyl group or naphthyl group and the like are preferred. As the aromatic heterocyclic group represented by $R^3$, for example, a monocyclic to a tricyclic, preferably a monocyclic or a bicyclic aromatic heterocyclic group containing one ore more heteroatoms such as nitrogen atom, oxygen atom and sulfur atom can be used. When two or more heteroatoms are contained, they may be same or different. Examples include thienyl group, furyl group, pyrrolyl group, imidazolyl group, pyrazolyl group, isoxazolyl group, pyridyl group, pyrazinyl group, pyrimidinyl group, pyridazinyl group, indolizinyl group, isoindolyl group, indolyl group, isoquinolyl group, quinolyl group, phthalazinyl group, naphthylidinyl group, quinoxalinyl group, quinazolinyl group, cinnolinyl group, pteridinyl group, carbazolyl group, acridinyl group, phenanthridinyl group, and phenothiazinyl group.

The aryl group, the aromatic heterocyclic group, the 5- to 7-membered cycloalkyl group, or the 5- to 7-membered cycloalkenyl group represented by $R^3$ may have one or more substituents on the ring. When the ring is substituted with two or more substituents, they may be same or different. The position of the substituent is not particularly limited, and the substituent may be present at any position on the ring. The type of the substituent is not particularly limited, and examples include a $C_1$-$C_6$ alkyl group, a $C_2$-$C_6$ alkenyl group, a $C_2$-$C_6$ alkynyl group, a $C_6$-$C_{14}$ aryl group, a heterocyclic group (the heterocycle used herein includes aromatic heterocyclic groups and partially saturated or saturated heterocyclic groups), a halogen atom (the halogen atom used herein may be any one of fluorine atom, chlorine atom, bromine atom, or iodine atom), hydroxyl group, oxo group, amino group, ammonium group, imino group, mercapto group, thioxo group, cyano group, nitro group, carboxyl group, phosphate group, sulfo group, hydrazino group, a $C_1$-$C_6$ ureido group, a $C_1$-$C_6$ imido group, isothiocyanate group, isocyanate group, a $C_1$-$C_6$ alkoxyl group, a $C_1$-$C_6$ alkylthio group, a $C_6$-$C_{14}$ aryloxy group, a heterocyclic-oxy group, a $C_6$-$C_{14}$ arylthio group, a heterocyclic-thio group, a $C_7$-$C_{15}$ aralkyl group, a heterocycle-alkyl group, a $C_7$-$C_{15}$ aralkyloxy group, a heterocyclic-alkyloxy group, a $C_1$-$C_6$ alkoxycarbonyl group, a $C_6$-$C_{14}$ aryloxycarbonyl group, a heterocyclic-oxycarbonyl group, a $C_2$-$C_7$alkylcarbonyl group, a $C_6$-$C_{14}$ arylcarbonyl group, a heterocyclic-carbonyl group, a $C_2$-$C_7$alkylcarbonyloxy group, a $C_6$-$C_{14}$ arylcarbonyloxy group, a heterocyclic-carbonyl oxygroup, a $C_2$-$C_8$ alkylcarbonylamino group, a $C_1$-$C_6$ sulfonyl group, a $C_1$-$C_6$ sulfinyl group, a $C_1$-$C_6$ sulfonylamino group, a $C_1$-$C_6$ carbamoyl group, and a $C_2$-$C_6$ sulfamoyl group.

The substituents exemplified above may be further substituted with one or more other substituents. Examples of such substituents include a hydroxy-$C_1$-$C_6$ alkyl group, a halogenated-$C_1$-$C_6$ alkyl group, a mono- or di-$C_1$-$C_6$ alkylamino group, a halogenated-$C_1$-$C_6$ alkylcarbonyl group, a halogenated-$C_6$-$C_{14}$ aryl group, a hydroxy-$C_6$-$C_{14}$ aryl group, and a mono- or di-$C_1$-$C_6$ alkylcarbamoyl group. However, the substituents explained above are referred to only for exemplification, and the substituents used are not limited to these examples.

Although the type of the —S-α-amino acid group represented by $R^4$ is not particularly limited, the group may preferably be an amino acid residue containing thiol group. The —S-α-amino acid residue may be a residue of an amino acid which constitutes a protein or a peptide compound. The type of proteins or peptide compounds is not particularly limited so far as they are physiologically acceptable. For example, serum protein such as albumin and globulin may preferably be used. Among serum protein, albumin is more preferred, and human albumin is particularly preferred. Examples of the aralkyl group represented by $R^4$ whose aryl moiety may optionally be substituted with one or more substituents include benzyl group, parahydroxybenzyl group, and 2,4-dihydrobenzyl group. $R^4$ and $R^5$ may combine together to represent single bond, and in that case, a 5-membered ring is formed which contains the nitrogen atom bound to $R^5$ and the selenium atom. As the $C_1$-$C_6$ alkyl group represented by $R^5$, those exemplified above can be used.

Physiologically acceptable salts of the compounds represented by the aforementioned general formula (I) or (I') may be used. The physiologically acceptable salt can suitably be chosen by the person skilled in the art. Hydrates of the compounds as free form or physiologically acceptable salts may also be used. When the compound represented by the aforementioned general formula (I) or (I') has one or more asymmetric carbon atoms, stereoisomers such as optical isomers and diastereoisomers, any mixture of the stereoisomers, racemates and the like may be used.

In some instances, the organoselenium agent can comprise an ebselen or an analog thereof, such as a compound having a formula of:

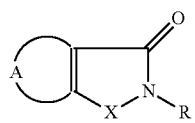

or a pharmaceutically acceptable salt thereof,
wherein X is selenium or sulfur, and
wherein R is selected from the group consisting of: H, alkyl having a carbon chain of 1 to 14 carbon atoms wherein the carbon chain is branched or unbranched which is optionally substituted with bensisoselenazol-3(2H)-one-2-yl, bensisotiazol-3(2H)-one-2-yl, OH, alkoxyl, SH, $NH_2$, N-alkylamino, N,N-dialkylamino, COOH, aryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I, and heteroaryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I, aryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I, heteroaryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I, and wherein A represents a saturated, unsaturated or polyunsaturated 3 to 6 member carbon chain wherein N may optionally substitute for one or more carbons, and which is optionally substituted with one or more of OR, SR, and alkylamino, $C_1$-$C_5$ alkyl, OH, alkoxyl, SH, $NH_2$, N-alkylamino, N,N-dialkylamino, COOH, CHO, $NO_2$, F, Cl, Br, and I.

In some instances, the organoselenium agent can comprise an ebselen having a chemical structure of:

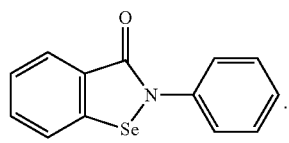

(EbSe 1)

In some instances, the organoselenium agent can comprise an ebselen structural analog, such as from classes of benzisoselenazol-3 (2H)-one-aryl,-alkyl, 2-pyridyl or 4-pyridyl substituted benzisoselenazol-3 (2H)-ones, bisbenzisoselenazol-3 (2H)-ones, 7-azabenzisoselenazol-3(2H)-one, selenamide, and bis(2-carbamoyl)phenyl diselenide, e.g., having a chemical structure below.

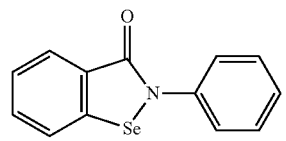

EbSe 2

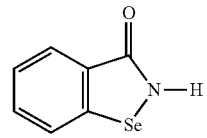

Ebse 3

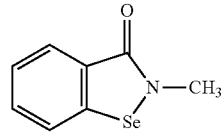

EbSe 4

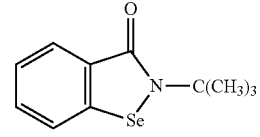

EbSe 5

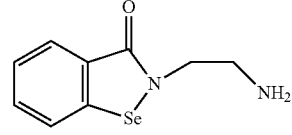

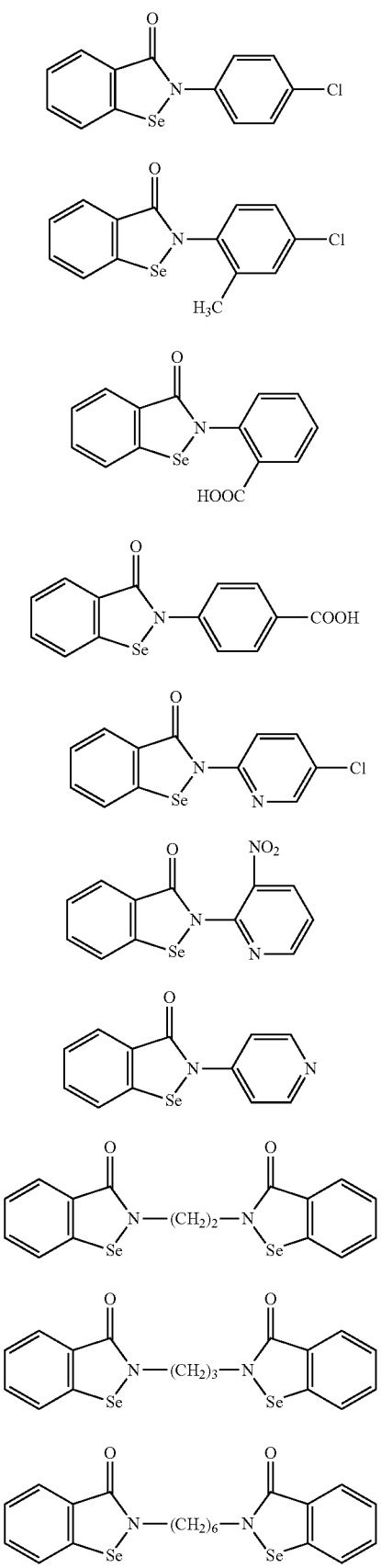
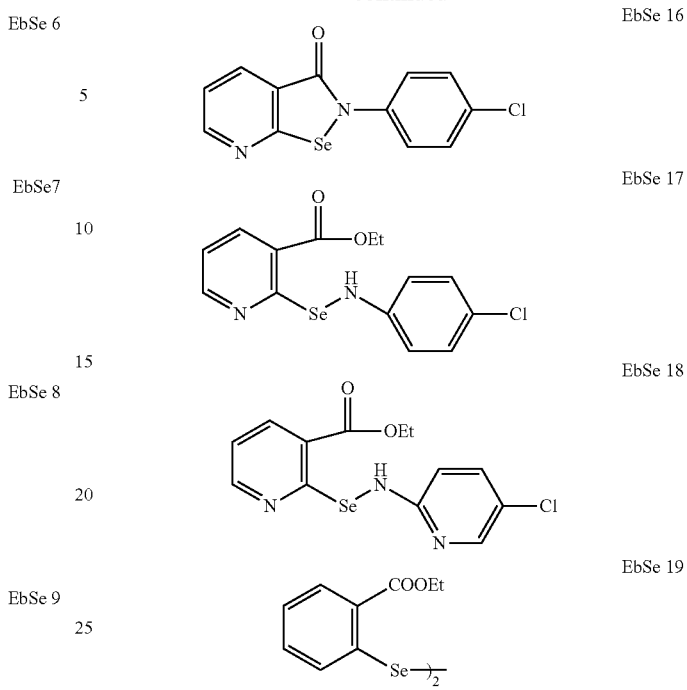

In some instances, the minimal inhibitory concentration (MIC) to one or more bacteria for an organoselenium agent (e.g., ebselen) contained in an antibiotic composition disclosed herein can be less than about: 100 µM, 90 µM, 80 µM, 70 µM, 60 µM, 50 µM, 40 µM, 30 µM, 25 µM, 20 µM, 15 µM, 10 µM, 5 µM, 1 µM, 0.5 µM, or 0.1 µM.

Methods and compositions presented herein can utilize an active agent in a freebase, salt, hydrate, polymorph, isomer, diastereomer, prodrug, metabolite, ion pair complex, or chelate form. An active agent can be formed using a pharmaceutically acceptable non-toxic acid or base, including an inorganic acid or base, or an organic acid or base. In some instances, an active agent that can be utilized in connection with the methods and compositions presented herein can be a pharmaceutically acceptable salt derived from acids including, but not limited to, the following: acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, or p-toluenesulfonic acid. In some instances, the active agent can be a salt of methanesulfonic acid.

In some instances, an antibiotic composition disclosed herein can further comprise or can be co-administered with one or more antibacterial/antimicrobial drugs, for example amikacin, azithromycin, cefixime, cefoperazone, cefotaxime, ceftazidime, ceftizoxime, ceftriaxone, chloramphenicol, ciprofloxacin, clindamycin, colistin, domeclocycline, doxycycline, erythromycin, gentamicin, mafenide, methacycline, minocycline, neomycin, norfloxacin, ofloxacin, oxytetracycline, polymyxin B, pyrimethamine, sulfacetamide, sulfisoxazole, tetracycline, tobramycin, trimethoprim, or any combination thereof.

In some instances, an antibiotic composition disclosed herein can further comprise or can be co-administered with oxazolidinone antibacterial drug(s), and/or one or more drug(s) selected from acebutolol, aceclidine, acetylsalicylic acid, N4 acetylsulfisoxazole, alclofenac, alprenolol, amfenac, amiloride, aminocaproic acid, aminoclonidine, aminozolamide, anisindione, apafant, atenolol, bacitracin, benoxaprofen, benoxinate, benzofenac, bepafant, betamethasone, betaxolol, bethanechol, brimonidine, bromfenac, bromhexine, bucloxic acid, bupivacaine, butibufen, carbachol, carprofen, celecoxib, cephalexin, chloramphenicol, chlordiazepoxide, chlorprocaine, chlorpropamide, chlortetracycline, cicloprofen, cinmetacin, ciprofloxacin, clidanac, clindamycin, clonidine, clonixin, clopirac, cocaine, cromolyn, cyclopentolate, cyproheptadine, demecarium, dexamethasone, dibucaine, diclofenac, diflusinal, dipivefrin, dorzolamide, enoxacin, epinephrine, erythromycin, eserine, estradiol, ethacrynic acid, etidocaine, etodolac, fenbufen, fenclofenac, fenclorac, fenoprofen, fentiazac, flufenamic acid, flufenisal, flunoxaprofen, fluorocinolone, fluorometholone, flurbiprofen and esters thereof, fluticasone propionate, furaprofen, furobufen, furofenac, furosemide, gancyclovir, gentamicin, gramicidin, hexylcaine, homatropine, hydrocortisone, ibufenac, ibuprofen and esters thereof, idoxuridine, indomethacin, indoprofen, interferons, isobutylmethylxanthine, isofluorophate, isoproterenol, isoxepac, ketoprofen, ketorolac, labetolol, lactorolac, latanoprost, levo-bunolol, lidocaine, lonazolac, loteprednol, meclofenamate, medrysone, mefenamic acid, mepivacaine, metaproterenol, methanamine, methylprednisolone, metiazinic, metoprolol, metronidazole, minopafant, miroprofen, MK-663, modipafant, nabumetome, nadolol, namoxyrate, naphazoline, naproxen and esters thereof, neomycin, nepafenac, nitroglycerin, norepinephrine, norfloxacin, nupafant, olfloxacin, olopatadine, oxaprozin, oxepinac, oxyphenbutazone, oxyprenolol, oxytetracycline, parecoxib, penicillins, perfloxacin, phenacetin, phenazopyridine, pheniramine, phenylbutazone, phenylephrine, phenylpropanolamine, phospholine, pilocarpine, pindolol, pirazolac, piroxicam, pirprofen, polymyxin, polymyxin B, prednisolone, prilocaine, probenecid, procaine, proparacaine, protizinic acid, rimexolone, rofecoxib, salbutamol, scopolamine, sotalol, sulfacetamide, sulfanilic acid, sulindac, suprofen, tenoxicam, terbutaline, tetracaine, tetracycline, theophyllamine, timolol, tobramycin, tolmetin, triamcinolone, trimethoprim, trospectomycin, valdecoxib, vancomycin, vidarabine, vitamin A, warfarin, zomepirac, and pharmaceutically acceptable salts thereof.

Formulations

In some cases, the present disclosure provides an antibiotic composition, wherein the antibiotic composition comprises: a silver-containing agent; and an organoselenium agent. In some instances, the silver-containing agent can comprise a silver ion. In some instances, the silver-containing agent can comprise silver nitrate. In some instances, the silver-containing agent can comprise silver dihydrogen citrate. In some instances, the organoselenium agent can comprise a selenazol compound. In some instances, the organoselenium agent can comprise a benzoisoselenazol-3 (2H)-one compound. In some instances, the organoselenium agent can comprise an ebselen. In some instances, the antibiotic composition can be in a dosage form of liquid. In some instances, the antibiotic composition can be in a dosage form of a solution or a suspension. In some instances, a concentration of the silver-containing agent in the antibiotic composition can be about 0.5 to 50 µM, about 1 to 25 µM, or about 1 to 10 µM. In some instances, a concentration of the silver-containing agent in the antibiotic composition can be about 5 µM. In some instances, a concentration of the organoselenium agent in the antibiotic composition can be about 4 to 25 µM, about 30 to 200 µM, about 30 to 150 µM, or about 30 to 100 µM. In some instances, a concentration of the organoselenium agent in the antibiotic composition can be about 40 µM or about 80 µM. In some instances, the silver-containing agent and the organoselenium agent can be a molar ratio of about 1:2 to about 1:20. In some instances, the silver-containing agent and the organoselenium agent can be a molar ratio of about 1:4, 1:8, or 1:16. In some instances, the antibiotic composition exhibits an $IC_{50}$ value of about 10-100 nM to one or more Gram-negative bacteria or Gram-positive bacteria. In some instances, the antibiotic composition exhibits an $IC_{50}$ value of about 50 nM or lower to one or more Gram-negative bacteria or Gram-positive bacteria. In some instances, the one or more Gram-negative bacteria can comprise K. pneumonia, A. baumannii, P. aeruginosa, E. cloacae, E. coli, or any combination thereof. In some instances, the antibiotic composition can comprise $AgNO_3$ and ebselen. In some instances, a composition disclosed herein can be in a liquid dosage form. In some instances, the antibiotic composition can comprise 5 µM of $AgNO_3$ and 4 µM of ebselen in a liquid dosage form. In some instances, the antibiotic composition can comprise 5 µM of $AgNO_3$ and 20 µM of ebselen in a liquid dosage form. In some instances, the antibiotic composition can comprise 5 µM of $AgNO_3$ and 40 µM of ebselen in a liquid dosage form. In some instances, the antibiotic composition can comprise 5 µM of $AgNO_3$ and 80 µM of ebselen in a liquid dosage form.

In some cases, the present disclosure provides a pharmaceutical formulation that can comprise the antibiotic composition disclosed herein. In some instances, the pharmaceutical formulation further can comprise an excipient disclosed herein.

In some cases, the present disclosure provides a method of making an antibiotic composition, comprising mixing a silver-containing agent and an organoselenium agent. In some instances, the mixing can be conducted in a liquid disclosed herein, for example a suspension, a colloid, or a solution. In some instances, the liquid comprises one or more active agents or excipients disclosed herein. In some instances, the mixing can comprise adding the silver-containing agent to a liquid that can comprise the organoselenium agent. In some instances, the mixing can comprise adding the organoselenium agent to a liquid that can comprise the silver-containing agent.

In some instances, an active agent disclosed herein can be present in about: 0.01-0.1, 0.1-1, 1-10, 1-20, 5-30, 5-40, 5-50, 10-20, 10-25, 10-30, 10-40, 10-50, 15-20, 15-25, 15-30, 15-40, 15-50, 20-30, 20-40, 20-50, 20-100, 30-40, 30-50, 30-60, 30-70, 30-80, 30-90, 30-100, 40-50, 40-60, 40-70, 40-80, 40-90, 40-100, 50-60, 50-70, 50-80, 50-90, 50-100, 50-150, 50-200, 50-300, 100-300, 100-400, 100-500, 1, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, or 1000 µM, or any combination thereof. In some instances, an active agent disclosed herein can be present in about: 1 mg-2.5 mg, 2.5-25 mg, 2.5-30 mg, 5-20 mg, 5-15 mg, 5-10 mg, 10-15 mg, 10-20 mg, 10-25 mg, 11.5-13 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 12.5 mg, 13 mg, 13.5 mg, 14 mg, 14.5 mg, 15 mg, 16 mg, 17 mg, 18 mg, 19 mg, or 20 mg. In some instances, an active agent disclosed herein can be present in about: 5-50 mg, 5-40 mg, 5-30 mg, 10-25 mg, 15-20 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 30 mg, 35 mg, 40 mg, 45 mg, or 50 mg, or any combination thereof. In some instances, two active agents are present in a molar or weight ratio by weight of about: 1:10 to 1:30, 1:20 to 1:30, 1:10 to 1:20, 1:1 to 1:15, or 1:1 to 1:0, 1:1 to 1:5, 1:1 to 1:4, 1:1 to 1:3, or 1:1 to 1:2. In some instances, two active agents are present in a molar or weight ratio by weight of about: 1:30, 1:29, 1:28, 1:27, 1:26, 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, or 1:1.

In some cases, an antibiotic composition can comprise multiple active agents administered of at least about 0.001 mg, for example, at least about: 0.01 mg, 0.1 mg, 0.2 mg, 0.3 mg, 0.4 mg, 0.5 mg, 0.6 mg, 0.7 mg, 0.8 mg, 0.9 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, or 10 mg, per kg body weight of a subject in need thereof. The powder composition may comprise a total dose of an active agent administered at about 0.1 to about 10.0 mg, for example, about 0.1-10.0 mg, about 0.1-9.0 mg, about 0.1-8.0 mg, about 0.1-7.0 mg, about 0.1-6.0 mg, about 0.1-5.0 mg, about 0.1-4.0 mg, about 0.1-3.0 mg, about 0.1-2.0 mg, about 0.1-1.0 mg, about 0.1-0.5 mg, about 0.2-10.0 mg, about 0.2-9.0 mg, about 0.2-8.0 mg, about 0.2-7.0 mg, about 0.2-6.0 mg, about 0.2-5.0 mg, about 0.2-4.0 mg, about 0.2-3.0 mg, about 0.2-2.0 mg, about 0.2-1.0 mg, about 0.2-0.5 mg, about 0.5-10.0 mg, about 0.5-9.0 mg, about 0.5-8.0 mg, about 0.5-7.0 mg, about 0.5-6.0 mg, about 0.5-5.0 mg, about 0.5-4.0 mg, about 0.5-3.0 mg, about 0.5-2.0 mg, about 0.5-1.0 mg, about 1.0-10.0 mg, about 1.0-5.0 mg, about 1.0-4.0 mg, about 1.0-3.0 mg, about 1.0-2.0 mg, about 2.0-10.0 mg, about 2.0-9.0 mg, about 2.0-8.0 mg, about 2.0-7.0 mg, about 2.0-6.0 mg, about 2.0-5.0 mg, about 2.0-4.0 mg, about 2.0-3.0 mg, about 5.0-10.0 mg, about 5.0-9.0 mg, about 5.0-8.0 mg, about 5.0-7.0 mg, about 5.0-6.0 mg, about 6.0-10.0 mg, about 6.0-9.0 mg, about 6.0-8.0 mg, about 6.0-7.0 mg, about 7.0-10.0 mg, about 7.0-9.0 mg, about 7.0-8.0 mg, about 8.0-10.0 mg, about 8.0-9.0 mg, or about 9.0-10.0 mg, per kg body weight of a subject in need thereof.

In some instances, a composition disclosed herein can comprise two or more active agents (e.g., a metal compound, ebselen or a derivative thereof), each of which can be independently present at a dose of about: 1-10 mg, 2.5-30 mg, 2.5-20 mg, 1-20 mg, 1-30 mg, 5-30 mg, 10-40 mg, 20-50 mg, 30-60 mg, 40-70 mg, 50-80 mg, 60-90 mg, or 1-100 mg, including but not limited to about: 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, or 100 mg.

Excipients

In some instances, the antibiotic composition disclosed herein can further comprise one or more excipients, e.g., different substance, or same substance but different sizes. In some instances, the excipient can comprise a carrier, e.g., water-insoluble polysaccharide or oligosaccharide. In some instances, the carrier can be selected from a group consisting of cellulose acetate, cellulose acetate butyrate, cellulose acetate propionate, cellulose acetate phthalate, chitosan, β-cyclodextrin, ethyl cellulose, hydroxypropylmethyl cellulose phthalate (HPMCP), microcrystalline cellulose, starch, and any combination thereof. In some instances, the excipient can comprise a thickening agent, e.g., a water-soluble polysaccharide. In some instances, the thickening agent can be selected from the group consisting of hydroxy propyl methyl cellulose (HPMC), acacia, alginic acid, colloidal silicone dioxide, carboxymethylcellulose calcium, gelatin, hydroxy propyl cellulose, hydroxyl propyl cellulose (hypromellose), methyl cellulose, sucrose, sodium alginate, sodium carboxy methyl cellulose, and any combination thereof. In some instances, the excipient can comprise a first excipient (any excipient disclosed herein) and a second excipient (any excipient disclosed herein). In some instances, the excipient can comprise a carrier (e.g., microcrystalline cellulose) and a thickening agent (e.g., HPMC).

In some instances, the antibiotic composition disclosed herein can further comprise one or more pharmaceutical excipients, for example ascorbic acid, EDTA dihydrate, glycerin, citric acid monohydrate, sodium citrate dihydrate, sodium benzoate, sodium propionate, 70% sorbitol solution, sucralose, FD&C Yellow #6, artificial orange flavor, artificial peppermint flavor, purified water, or any combination thereof. In some instances, the one or more pharmaceutical excipients comprise ascorbic acid, EDTA dihydrate, glycerin, citric acid monohydrate, sodium citrate dihydrate, proplyparaben, methylparaben, propylene glycol, 70% sorbitol solution, sucralose, FD&C Yellow #6, artificial orange flavor, artificial peppermint flavor, purified water, or any combination thereof.

Suitable preservatives non-restrictively include mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

One or more acceptable pH adjusting agents and/or buffering agents can be included in a composition disclosed herein, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in a pharmaceutically acceptable range.

In some instances, an antibiotic composition disclosed herein can comprise a pH adjusting agent. In some instances, the pH adjusting agent can be selected from the group consisting of ascorbic acid, sodium ascorbate, tartaric acid, sodium tartrate, potassium tartrate, calcium tartrate, lithium tartrate, citric acid, sodium citrate, potassium citrate, calcium citrate, lithium citrate, phosphoric acid, sodium dihydrogenphosphate, sodium monohydrogenphosphate, lithium phosphate, potassium phosphate, calcium phosphate, sodium carbonate, sodium hydrogencarbonate, lactic acid, sodium lactate, potassium lactate, calcium lactate, acetic acid, sodium acetate, potassium acetate, calcium acetate, propionic acid, sulphuric acid, sodium sulphate, potassium sulphate, boric acid, sodium borate, maleic acid, lithium maleate, sodium maleate, potassium maleate, calcium maleate, succinic acid, lithium succinate, sodium succinate, potassium succinate, calcium succinate, fumaric acid, glutamic acid, formic acid, malic acid, hydrochloric acid, nitric acid, sodium hydroxide, potassium hydroxide, triethanolamine, diisopropanolamine, ammonia solution, monoethanole amine, diethanoleamine, triethanoleamine meglumine, sodium citrate, sodium bicarbonate, potassium bicarbonate, and any combination thereof. In some instances, a pH adjusting agent disclosed herein can be acetic acid; adipic acid; ammonium aluminum sulphate; ammonium bicarbonate; ammonium carbonate; ammonium citrate, dibasic; ammonium citrate, monobasic; ammonium hydroxide; ammonium phosphate, dibasic; ammonium phosphate, monobasic; calcium acetate; calcium acid pyrophosphate; calcium carbonate; calcium chloride; calcium citrate; calcium fumarate; calcium gluconate; calcium hydroxide; calcium lactate; calcium oxide; calcium phosphate, dibasic; calcium phosphate, monobasic; calcium phosphate, tribasic; calcium sulphate; carbon dioxide; citric acid; cream of tartar; fumaric acid; gluconic acid; glucono-delta-lactone; hydrochloric acid; lactic acid; magnesium carbonate; magnesium citrate; magnesium fumarate; magnesium hydroxide; magnesium oxide; magnesium phosphate; magnesium sulphate; malic acid; manganese sulphate; metatartaric acid; phosphoric acid; potassium acid tartrate; potassium aluminum sulphate; potassium bicarbonate; potassium carbonate; potassium chloride; potassium citrate; potassium fumarate; potassium hydroxide; potassium lactate; potassium phosphate, dibasic; potassium phosphate, tribasic; potassium sulphate; potassium tartrate; potassium tripolyphosphate; sodium acetate; sodium acid pyrophosphate; sodium acid tartrate; sodium aluminum phosphate; sodium aluminum sulphate; sodium bicarbonate; sodium bisulphate; sodium carbonate; sodium citrate; sodium fumarate; sodium gluconate; sodium hexametaphosphate; sodium hydroxide; sodium lactate; sodium phosphate, dibasic; sodium phosphate, monobasic; sodium phosphate, tribasic; sodium potassium hexametaphosphate; sodium potassium tartrate; sodium potassium tripolyphosphate; sodium pyrophosphate, tetrabasic; sodium tripolyphosphate; sulphuric acid; sulphurous acid; tartaric acid; or any combination thereof.

In some instances, an antibiotic composition disclosed herein can comprise a sugar alcohol. In some instances, the sugar alcohol can be selected from the group consisting of mannitol, glycerol, galactitol, fucitol, inositol, volemitol, maltotriitol, maltoetetraitol, polyglycitol, erythritol, threitol, ribitol, arabitol, xylitol, allitol, dulcitol, glucitol, sorbitol, altritol, iditol, maltitol, lactitol, isomalt, and any combination thereof. In some instances, the sugar alcohol has 3, 4, 5, 6, 7, 12, 18, or 24 carbons.

In some instances, a composition disclosed herein can comprise suitable additives, including, but not limited to, diluents, binders, surfactants, lubricants, glidants, coating materials, plasticizers, coloring agents, flavoring agents, or pharmaceutically inert materials. Examples of diluents include, for example, cellulose; cellulose derivatives such as microcrystalline cellulose and the like; starch; starch derivatives such as corn starch, cyclodextrin and the like; sugar; sugar alcohol such as lactose, D-mannitol and the like; inorganic diluents such as dried aluminum hydroxide gel, precipitated calcium carbonate, magnesium aluminometasilicate, dibasic calcium phosphate and the like. Examples of binders include, for example, hydroxypropylcellulose, methylcellulose, hydroxypropylmethylcellulose (hydroxypropyl methylcellulose), povidone, dextrin, pullulane, hydroxypropyl starch, polyvinyl alcohol, scacia, agar, gelatin, tragacanth, macrogol and the like. Examples of surfactants include, for example, sucrose esters of fatty acids, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, lauromacrogol, quaternary ammonium salts (e.g., Benzyldimethyltetradecylammonium Chloride Hydrate, Benzethonium Chloride, Benzylcetyldimethylammonium Chloride Hydrate, Benzyldimethylstearylammonium Chloride Hydrate, Benzyldodecyldimethylammonium Chloride Dihydrate, Benzyldodecyldimethylammonium Bromide), and the like. Examples of lubricants include, for example, stearic acid, calcium stearate, magnesium stearate, talc and the like. Examples of glidants include, for example, dried aluminum hydroxide gel, magnesium silicate and the like. Examples of coating materials include, for example, hydroxypropylmethyl cellulose 2910, aminoalkyl methacrylate copolymer E, polyvinylacetal diethylaminoacetate, macrogol 6000, titanium oxide and the like. Examples of plasticizers include, for example, triethyl citrate, triacetin, macrogol 6000 and the like.

Dosage Forms

In some instances, active agents disclosed herein are formulated as a dosage form of tablet, capsule, gel, lollipop, parenteral, intraspinal infusion, inhalation, spray, aerosol, transdermal patch, iontophoresis transport, absorbing gel, liquid, liquid tannate, suppositories, injection, I.V. drip, or a combination thereof to treat subjects. In some instances, the agents are formulated as single oral dosage form such as a tablet, capsule, cachet, soft gelatin capsule, hard gelatin capsule, extended release capsule, tannate tablet, oral disintegrating tablet, multi-layer tablet, effervescent tablet, bead, liquid, oral suspension, chewable lozenge, oral solution, lozenge, lollipop, oral syrup, sterile packaged powder including pharmaceutically-acceptable excipients, other oral dosage forms, or a combination thereof. In some instances, a composition of the disclosure herein can be administered using one or more different dosage forms which are further disclosed herein. For example, a composition comprising multiple active agents can be administered in solid, semi-solid, micro-emulsion, gel, patch or liquid form. Such dosage forms are further disclosed herein. In some instances, the disclosure herein relates to methods and compositions formulated for oral delivery to a subject in need. In some instances, a composition can be formulated so as to deliver one or more pharmaceutically active agents to a subject through a mucosa layer in the mouth or esophagus. In some instances, the composition can be formulated to deliver one or more pharmaceutically active agents to a subject through a mucosa layer in the stomach and/or intestines.

In some instances, compositions disclosed herein are provided in modified release dosage forms (such as immediate release, controlled release or both), which comprise an effective amount of an active agent; and one or more release controlling excipients as disclosed herein. Suitable modified release dosage vehicles include, but are not limited to, hydrophilic or hydrophobic matrix devices, water-soluble separating layer coatings, enteric coatings, osmotic devices, multi-particulate devices, and combinations thereof. In some instances, the compositions comprise non-release controlling excipients. In some instances, compositions disclosed herein are provided in enteric coated dosage forms. In some instances, compositions disclosed herein comprise non-release controlling excipients. In some instances, compositions disclosed herein are provided in effervescent dosage forms. In some instances, the compositions comprise non-release controlling excipients.

In some instances, a composition disclosed herein can be provided in a dosage form that has at least one component that facilitates the immediate release of an active agent, and at least one component that can facilitate the controlled release of an active agent. In some instances, the dosage form can be capable of giving a discontinuous release of the compound in the form of at least two consecutive pulses separated in time from 0.1 up to 24 hours. The compositions can comprise one or more release controlling and non-release controlling excipients, such as those excipients suitable for a disruptable semi-permeable membrane and as swellable substances. In some instances, a composition disclosed herein can be provided in a dosage form for oral administration to a subject, which comprise one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer. In some instances, the compositions further comprise cellulose, disodium hydrogen phosphate, hydroxypropyl cellulose, hypromellose, lactose, mannitol, or sodium lauryl sulfate. In some instances, the compositions further comprise glyceryl monostearate 40-50, hydroxypropyl cellulose, hypromellose, magnesium stearate, methacrylic acid copolymer type C, polysorbate 80, sugar spheres, talc, or triethyl citrate. In some instances, the compositions further comprise carnauba wax, crospovidone, diacetylated monoglycerides, ethylcellulose, hydroxypropyl cellulose, hypromellose phthalate, magnesium stearate, mannitol, sodium hydroxide, sodium stearyl fumarate, talc, titanium dioxide, or yellow ferric oxide. In some instances, the compositions further comprise calcium stearate, crospovidone, hydroxypropyl methylcellulose, iron oxide, mannitol, methacrylic acid copolymer, polysorbate 80, povidone, propylene glycol, sodium carbonate, sodium lauryl sulfate, titanium dioxide, and triethyl citrate.

In some instances, compositions disclosed herein are in unit-dosage forms or multiple-dosage forms. Unit-dosage forms, as used herein, refer to physically discrete units suitable for administration to human or non-human animal subjects and packaged individually. Each unit-dose contains a predetermined quantity of an active ingredient(s) sufficient to produce the desired therapeutic effect, in association with the required pharmaceutical carriers or excipients. Examples of unit-dosage forms include, but are not limited to, ampules, syringes, and individually packaged tablets and capsules. In some instances, unit-dosage forms are administered in fractions or multiples thereof. A multiple-dosage form can be a plurality of identical unit-dosage forms packaged in a single container, which can be administered in segregated unit-dosage form. Examples of multiple-dosage forms include, but are not limited to, vials, bottles of tablets or capsules, or bottles of pints or gallons. In some instances, the multiple dosage forms comprise different pharmaceutically active agents.

In some instances, a kit can be provided comprising an antibiotic composition disclosed herein. In some instances, the kit further can comprise a set of instructions.

In some instances, compositions disclosed herein can be formulated in dosage forms for oral, parenteral, or topical administration. In some instances, the compositions can be formulated as a modified release dosage form, including immediate-, delayed-, extended-, prolonged-, sustained-, pulsatile-, controlled-, extended, accelerated- and fast-, targeted-, programmed-release, and gastric retention dosage forms. In some instances, the compositions can be in one or more dosage form. For example, a composition can be administered in a solid or liquid form. Examples of solid dosage forms include but are not limited to discrete units in capsules or tablets, as a powder or granule, or present in a tablet conventionally formed by compression molding. In some instances, such compressed tablets are prepared by compressing in a suitable machine the three or more agents and a pharmaceutically acceptable carrier. The molded tablets can be optionally coated or scored, having indicia inscribed thereon and can be so formulated as to cause immediate, substantially immediate, slow, controlled or extended release of the active agents disclosed herein. In some instances, dosage forms disclosed herein comprise acceptable carriers or salts known in the art, such as those described in the Handbook of Pharmaceutical Excipients, American Pharmaceutical Association (1986), incorporated by reference herein in its entirety. In some instances, one or more pharmaceutically active agents are mixed with a pharmaceutical excipient to form a solid preformulation composition comprising a homogeneous mixture of compounds disclosed herein. When referring to compositions disclosed herein as "homogeneous", it can be meant that the agents are dispersed evenly throughout the composition so that the composition can be subdivided into unit dosage forms such as tablets or capsules. In some instances, this solid preformulation composition can be then subdivided into unit dosage forms of the type described above comprising from, for example, about 1.0 mg to about 15 mg of an active agent disclosed herein.

In some instances, compositions disclosed herein are formulated, in the case of capsules or tablets, to be swallowed whole, for example with water. The inclusion of the side-effect-reducing agent such as an antihistamine or antiemetic to abate common symptoms of nausea and vomiting are believed beneficial in that promethazine or a salt thereof, or the like will eliminate or minimize the amount of discomfort. Adverse effects reduced or eliminated include but are not limited to nausea, vomiting, other gastric upsets, constipation, skin rashes, allergic reactions such as swelling, difficulty breathing, closing of throat, abdominal pain, unusual bleeding or bruising, CNS suppression and respiratory suppression.

In some instances, a dosage form disclosed herein can be manufactured using processes that are well known to those of skill in the art. For example, for the manufacture of tablets (including but not limited to single layer, bi-layer, coated, of multi-layer tablets) or capsules, the agents can be dispersed uniformly in one or more excipients, for example, using high shear granulation, low shear granulation, fluid bed granulation, or by blending for direct compression. Excipients include diluents, binders, disintegrants, dispersants, lubricants, glidants, stabilizers, surfactants and colorants. Diluents, also termed "fillers", are used to increase the bulk of a tablet so that a practical size can be provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. In some instances, binders impart cohesive qualities to a tablet formulation, or a particle formulation in a capsule, and are used to help a tablet remain intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, waxes, natural and synthetic gums, e.g., acacia, tragacanth, sodium alginate, and synthetic polymers such as polymethacrylates and polyvinylpyrrolidone. In some instances, lubricants facilitate tablet manufacture; non-limiting examples thereof include magnesium stearate, calcium stearate, stearic acid, glyceryl behenate, and polyethylene glycol. In some instances, disintegrants facilitate tablet disintegration after administration, and non-limiting examples thereof include starches, alginic acid, crosslinked polymers such as, e.g., crosslinked polyvinylpyrrolidone, croscarmellose sodium, potassium or sodium starch glycolate, clays, celluloses, starches, gums and the like. Non-limiting examples of suitable glidants include silicon dioxide, talc and the like. In some instances, stabilizers inhibit or retard drug decomposition reactions, including oxidative reactions. In some instances, a surfactant can be anionic, cationic, amphoteric or nonionic. In some instances, the tablets (or particles) comprise nontoxic auxiliary substances such as pH buffering agents, preservatives, e.g., antioxidants, wetting or emulsifying agents, solubilizing agents, coating agents, flavoring agents, and the like. In some instances, exemplary excipients include cellulose ethers such as hydroxypropylmethylcellulose (e.g., Methocel K4M) or silicified microcrystalline cellulose; polyvinylacetate-based excipients such as, e.g., Kollidon SR, and polymers and copolymers based on methacrylates and methacrylic acid such as, e.g., Eudragit NE 30D; microcrystalline cellulose, sodium carboxymethyl cellulose, sodium starch glycolate, corn starch, colloidal silica, Sodium Laurel Sulphate, Magnesium Stearate, Prosolve SMCC (HD90), croscarmellose Sodium, Crospovidone NF, Avicel PH200 or a combination thereof. In some instances, compositions disclosed herein comprise one or more combination of excipients that slow the release of the agents by coating or temporarily bonding or decreasing their solubility of the active agents. Examples of these excipients include cellulose ethers such as hydroxypropylmethylcellulose (e.g., Methocel K4M) or silicified microcrystalline cellulose, polyvinylacetate-based excipients such as, e.g., Kollidon SR, and polymers and copolymers based on methacrylates and methacrylic acid such as, e.g., Eudragit NE 30D.

In some instances, compositions comprise one or more carriers that protect the agents against rapid elimination from the body, such as time-release formulations or coatings. Such carriers include controlled-release formulations, including, for example, microencapsulated delivery systems. In some instances, the active agents are included in the pharmaceutically acceptable carrier in amounts sufficient to treat a subject's pain, with reduced adverse effects. In some instances, the compositions are in oral-dosage form and comprise a matrix that includes, for example, an active agent formulated for controlled release. In some instances, the matrix can be compressible into a tablet and can be optionally overcoated with a coating that controls the release of the active agent from the composition. In some instances, blood levels of analgesics are maintained within a therapeutic range over an extended period of time. In certain some instances, the matrix can be encapsulated. Tablets or capsules containing a composition disclosed herein can be coated or otherwise compounded to provide a dosage form affording the advantage of prolonged action. For example, the tablet or capsule contains an inner dosage and an outer dosage component, the latter being in the form of an envelope over the former. The two components can be separated by an enteric layer that serves to resist disintegration in the stomach and permit the inner component to pass intact into the duodenum or to be controlled in release. In some instances, for controlled extended release, the capsule has micro drilled holes. In some instances, a coating comprising a side-effect-reducing compound can be prepared by admixing a compound like promethazine with polyvinylpyrrolidone (PVP) 29/32 or hydroxypropyl methylcellulose (HPMC) and water/isopropyl alcohol and triethyl acetate. Such a coating can be spray coated onto the tablet cores. In some instances, the coating can be applied using a press-coating process with a blend consisting of 80% by weight promethazine and 20% by weight of lactose and hydroxypropyl methylcellulose type 2910. Press-coating techniques are known in the art and are described in U.S. Pat. No. 6,372,254, which can be herein incorporated by reference in its entirety.

In some instances, a dosage form disclosed herein can be an effervescent dosage form. Effervescent means that the dosage form, when mixed with liquid, including water and saliva, evolves a gas. Some effervescent agents (or effervescent couple) evolve gas by means of a chemical reaction which takes place upon exposure of the effervescent disintegration agent to water and/or to saliva in the mouth. This reaction can be the result of the reaction of a soluble acid source and an alkali monocarbonate or carbonate source. The reaction of these two general compounds produces carbon dioxide gas upon contact with water or saliva. An effervescent couple (or the individual acid and base separately) can be coated with a solvent protective or enteric coating to prevent premature reaction. In some instances, such a couple can be mixed with previously lyophilized particles (such as one or more pharmaceutically active agents coated with a solvent protective or enteric coating. In some instances, the acid source can be any which are safe for human consumption and includes food acids, acid and hydrite antacids such as, for example: citric, tartaric, amalic, fumeric, adipic, and succinics. Carbonate sources include dry solid carbonate and bicarbonate salt such as, for example, sodium bicarbonate, sodium carbonate, potassium bicarbonate and potassium carbonate, magnesium carbonate and the like. Reactants which evolve oxygen or other gasses and which are safe for human consumption are also included. In some instances, citric acid and sodium bicarbonate can be used.

In some instances, a dosage form disclosed herein can be in a candy form (e.g., matrix), such as a lollipop or lozenge. In some instances, one or more pharmaceutically active agents are dispersed within a candy matrix. In some instances, the candy matrix can comprise one or more sugars (such as dextrose or sucrose). In some instances, the candy matrix can be a sugar-free matrix. The choice of a particular candy matrix can be subject to wide variation. In some instances, conventional sweeteners such as sucrose are utilized, or sugar alcohols suitable for use with diabetic patients, such as sorbitol or mannitol might be employed. In some instances, other sweeteners, such as the aspartanes, are easily incorporated into a composition in accordance with compositions disclosed herein. The candy base can be very soft and fast dissolving, or can be hard and slower dissolving. Various forms will have advantages in different situations. In some instances, a candy mass comprising at least one pharmaceutically active agent can be orally administered to a subject in need thereof so that the agent will be released into the subject's mouth as the candy mass dissolves. The drug rapidly enters the subject bloodstream, and importantly, the blood in the veins draining from the mouth and the pharyngeal and esophageal areas passes through a substantial portion of the body (so that the drug can be absorbed) before the blood passes through the liver (where the drug can be inactivated). In some instances, a subject in need thereof can be a human adult or child in suffering from a cough and/or pain. In some instances, a candy matrix (e.g., lollipop or lozenge) disclosed herein can comprise a composition that lacks a stimulant. In some instances, the composition has a sedative effect in addition to providing cough and/or pain relief to a subject in need thereof. In some instances, the candy matrix (lollipop or lozenge) can comprise a composition that can comprise a stimulant. In some instances, the composition provides an anti-sedative effect in addition to providing cough and/or pain relief to a subject in need thereof. In some instances, a candy mass disclosed herein can comprise one or more layers which comprise different pharmaceutically active agents and or rates of dissolution. In some instances, a multilayer candy mass (such as a lollipop) can comprise an outer layer with a concentration of one or more pharmaceutically active agents differing from that of one or more inner layers. Such a drug delivery system has a variety of applications. By way of example, it can be desirable to quickly get a predetermined dose of a first pharmaceutically active agent into the bloodstream to obtain a desired effect and then use a different inner layer to deliver one or more other agents. The choices of matrix and the concentration of the drug in the matrix are important factors with respect to the rate of drug uptake. In some instances, a matrix that dissolves quickly delivers drug into the patient's mouth for absorption more quickly than a matrix that can be slow to dissolve. In some instances, a candy matrix that contains one or more pharmaceutically active agents in a high concentration releases more of the one or more pharmaceutically active agents in a given period of time than a candy having a low concentration.

In some instances, dosage forms disclosed herein take the form of pharmaceutical particles manufactured by a variety of methods, including but not limited to high-pressure homogenization, wet or dry ball milling, or small particle precipitation (e.g., nGimat's NanoSpray). Other methods useful to make a suitable powder formulation are the preparation of a solution of active ingredients and excipients, followed by precipitation, filtration, and pulverization, or followed by removal of the solvent by freeze-drying, followed by pulverization of the powder to the desired particle size. In some instances, the pharmaceutical particles have a final size of 3-1000 μm, such as at most 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000 μm. In some instances, the pharmaceutical particles have a final size of 10-500 μm. In some instances, the pharmaceutical particles have a final size of 50-600 μm. In some instances, the pharmaceutical particles have a final size of 100-800 μm. In some instances, these dosage forms include immediate-release particles in combination with controlled-release particles in a ratio sufficient useful for delivering the desired dosages of active agents.

Liquid Compositions

In some aspects, liquid compositions disclosed herein are shelf-stable, for examples, the liquid compositions do not separate on the shelf (both floating and settling) or do not require vigorous shaking (which greatly affects dosing consistency). In some instances, one or more active agents in liquid compositions disclosed herein are provided as in modified release, e.g., controlled release, immediate release, or mixed. In some instances, one or more active agents in liquid compositions disclosed herein can comprise a decongestant, antitussive, expectorant or analgesic in a matrix formulated for modified release. Exemplary expectorants include ammonium chloride, N-acetylcysteine, ambroxol, guaifenesin (e.g., glycerol, guaiacolate), terpin hydrate, glyceryl guaiacolate, potassium iodide, potassium citrate, potassium guaicolsulfonate, Oregano Leaf Extract 25-500 mg (which can be a liquid extract), Red Clover 25-500 mg, Buckthorn Root 25-500 mg, Fenugreek 25-500 mg, or any mixture thereof. Examples of carriers for the actives include any degradable, partially degradable or non-degradable and generally biocompatible polymer, e.g., polystirex, polypropylene, polyethylene, polacrilex, poly-lactic acid (PLA), polyglycolic acid (PGA) and/or poly-lactic polyglycolic acid (PGLA), e.g., in the form or a liquid, matrix, or bead.

In some instances, a liquid composition disclosed herein has a viscosity (spindle viscosity) from about 150 to about 1000 centipoises at 50 RPM, for example from about 200 to about 1000 centipoises at 50 RPM or from about 400 to about 700 centipoises at 50 RPM; or from about 150 to about 1200 centipoises measured at 10 RPM. Viscosity can be measured by a method in USP (United States Pharmacopeia), selected from <911> Viscosity-Capillary Viscometer Methods, <912> Rotational Rheometer Methods, and/or <913> Rolling Ball Viscometer Method. In some instances, an amount of viscosity modifier used depends on the desired "thickness" of the composition and the type viscosity modifier used. In some instances, combinations of viscosity modifiers are employed. For example, in an exemplary embodiment with a viscosity of about 1500 to about 4500 cps, up to about 1.0 w/v xanthan gum can be used with up to about 3.0 w/v microcrystalline cellulose can be as a viscosity modifier. In some instances, a pH of a liquid composition disclosed herein can be about: 2.5-5, 6-8, 5-9, 4-10, 7-8, 7-9, 7-10, 6-7, 5-7, or 4-7. In some instances, a pH of a liquid composition disclosed herein can be about: 2, 3, 4, 5, 6, 7, 8, 9, 10, 11, or 12. In some instances, the pH can be about 6.0, 6.1, 6.2, 6.3, 6.4, 6.5, 6.6, 6.7, 6.8, 6.9, 7.0, 7.1, 7.2, 7.3, 7.4, 7.5, 7.8, 7.9, 7.10, for example, ranging from about 6.8 to about 7.4.

In one aspect, a liquid composition disclosed herein can be a suspension comprising beads (e.g., microbeads), wherein a portion of the one or more beads have an immediate release profile and another portion have a controlled release profile. In some instances, one or more beads include an enteric coat, a resin coat, a lacquer coat, a pH-sensitive coating, a biodegradable polymer matrix, a water soluble matrix, an ionic matrix, or any combination thereof. In some instances, one or more beads include one or more polymers selected from cellulose, ethylcellulose, methylcellulose, propylcellulose, methoxypropylcellulose, cellulose nitrate, poly(vinyl alcohol), poly(vinyl chloride), polystyrene, polyethylene, polypropylene, poly(ethylene-co-vinyl acetate), poly(hydroxybutyric acid), poly(hydroxy-valerianic acid-co-hydroxybutyric acid), poly(lactic acid), poly(glycolic acid), poly(lactic acid-co-glycolic acid), poly (.epsilon.(-caprolactones), poly(.epsilon.-caprolactone-co-DL-lactic acid), poly(maleic anhydride), polyamides, gelatin, chitosan, collagen, poly(hydroxyalkyl)-L-glutamines, poly(.gamma.-ethyl-L-glutaminate-co-glutamic acid), poly (L-leucine-co-L-aspartic acid), poly(proline-co-glutamic acid), poly(alkyl 2-cyanoacrylates), polyurethanes, poly(methyl methacrylate), poly(methyl methacrylate-co-methacrylic acid) and poly(methacrylate-co-hydroxypropyl methacrylate), polystyrene, polistirex, polacrilex, salts thereof, and any combination thereof.

In some instances, a liquid composition disclosed herein can be a syrup, a ready-to-use suspension, or extemporaneously prepared liquid syrup or suspension such as, for example, dry powder for reconstitution with water, liquid concentrate for dilution, dispersible tablet or capsule. In the case of extemporaneously prepared syrup or suspension, the concentration of ingredients can be based on the reconstituted product. In some instances, the liquid dosing form can be for oral administration, intravenous injection, intramuscular injection, or for topical administration (e.g., as a cream, gel, ointment, or bandage). An orally administered liquid dosing form can be beneficial for subjects that have dysphagia or difficulty swallowing. In some instances, the liquid dosage form includes one or more pharmaceutically acceptable carriers or excipients. In some instances, the liquid pharmaceutical composition contains one or more active agents, e.g., present at therapeutically effective amounts in the dosage form. These amounts differ depending on the drug and prescribed dosage regimens. For instance, liquid preparations intended for infants contain high drug concentrations to enable small doses and reduced dosing frequency. In some instances, an amount of drug in the composition can be from about 0.02 to about 15 percent by weight, e.g., from about 0.1 to about 10 percent by weight of the total composition. In the case of dry powder for reconstitution with water, the drug can be present as uncoated or coated particles.

In some instances, a liquid composition disclosed herein can comprise a taste masking liquid excipient base for administration of an unpleasant tasting medicine. In some instances, said excipient base has higher than normal viscosities, e.g., due to presence of polyethylene glycol and/or sodium carboxymethyl cellulose. In some instances, high viscosity liquid excipient base provides taste masking benefits to the extent that extra strength compositions can be prepared containing increased concentrations of adverse tasting pharmaceutical compositions. For example, an active agent normally administered in dosages of no more than 100 milligrams in 5 milliliters of liquid, can be administered in dosages of 200 milligrams in the same volume of liquid without the patient experiencing an unduly adverse taste.

In another aspect, a method disclosed herein increases the shelf-life and stability of the actives agents, e.g., by preventing the separation of the components by taking steps to reduce or eliminate bubble formation. In some instances, steps for minimizing, reducing and/or eliminating bubble formation include, but are not limited to using the following steps alone or in combination: using a diaphragm pump to combine, e.g., the water and the thixotropic agent and one or more preservatives, colorants and flavorants; placing the recirculating tube below the surface of the liquid; adding liquids along the side of a vessel holding the liquid; sprinkling beads (e.g., one or more beads that includes one or more active agents) onto the surface of the liquid; mixing the solution in the absence of one or more paddles that scrape the vessel; mixing the solution with a propeller mixer; mixing the solution with a propeller mixer at a speed that reduces or minimizes cavitation and combinations of two or more of these steps.

In some instances, a liquid composition disclosed herein can be for use in treating a disease or condition disclosed herein, e.g., cough, allergy, cold, or associated symptoms. In some instances, a subject (e.g., person) suffering from cold or cold-like symptoms finds relief by orally ingesting a safe and effective amount of the liquid compositions as described above. The safe and effective amount of liquid composition can be dependent upon the concentration of the therapeutic components present in the liquid compositions. In some instances, the safe and effective amount of liquid composition can be in a range of 1-30 ml, e.g. 1-10 ml, per dosage of the liquid composition. In some instances, a liquid composition disclosed herein can be safely consumed by a child. In some instances, a subject (e.g., person) can be taking multiple doses (1, 2, 3, 4, 5, 6, 7, or 8 doses) of the liquid composition per day. In some instances, a liquid composition herein provides an effective amount of one or more active agents for 2-4 hours, 4-6 hours, 6-8 hours, 12 hours, or 24 hours. In some instances, a liquid composition disclosed herein can be administered to a subject (e.g., person) in a liquid form (e.g. by dosage cup or reservoir such as a spoon) or it can be encapsulated in a soft gelatin capsule that can be chewable or swallowable by the individual. In some instances, the liquid composition can be blended with compositions such as ice, milk, soda, juice, or some other edible composition and administered to the individual.

In some instances, a liquid dosage form disclosed herein can be for oral administration, intravenous injection, intramuscular injection, or for topical administration (e.g., as a cream or gel). An orally administered liquid dosing form can be beneficial for subjects that have dysphagia or difficulty swallowing. A single dose of an orally administered liquid dosing form can be from 1 mL to about 500 mL in volume, or more. For example, the single dose of an orally administered liquid dosing form can be about 1-500 mL, 1-250 mL, 1-100 mL, 1-50 mL, 1-30 mL, 1-20 mL, 1-15 mL, 1-10 mL, 1-5 mL, 1-2.5 mL, 2.5-50 mL, 2.5-30 mL, 2.5-20 mL, 2.5-15 mL, 2.5-10 mL, 2.5-5 mL, 5-50 mL, 5-30 mL, 5-20 mL, 5-15 mL, 5-10 mL, 10-50 mL, 10-30 mL, 10-20 mL, 10-15 mL, 15-50 mL, 15-30 mL, 15-20 mL, 20-50 mL, 20-30 mL, 30-50 mL, 1 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL, 8 mL, 8.5 mL, 9 mL, 9.5 mL, 10 mL, 11 mL, 12 mL, 13 mL, 14 mL, 15 mL, 16 mL, 17 mL, 18 mL, 19 mL, 20 mL, 21 mL, 22 mL, 23 mL, 24 mL, 25 mL, 30 mL, 35 mL, 40 mL, 45 mL, 50 mL, 60 mL, 70 mL, 80 mL, 90 mL, 100 mL, 110 mL, 120 mL, 130 mL, 140 mL, 150 mL, 160 mL, 170 mL, 180 mL, 190 mL, 200 mL, 250 mL, 300 mL, 350 mL, 400 mL, 450 mL, or 500 mL.

In some instances, pharmaceutically acceptable carriers or excipients disclosed herein include pH modifying agent(s) (e.g., buffering agent(s)), stabilizing agent(s), thickening agent(s), sweetening agent(s), flavoring agent(s), colorant agent(s), preservative agent(s), emulsifying agent(s), solubilizing agent(s), antioxidant agent(s), or any combination thereof.

In some instances, a stabilizing agent disclosed herein includes any suitable monohydroxy phenol component or polyhydroxy phenol component, or a combination thereof. In some instances, such stabilizing agents are also function as antioxidant agents, or antimicrobial agents. In some instances, a thickening agent or viscosity-enhancing agent disclosed herein improves the mouth-feel of the liquid oral dosage form and/or to help coat the lining of the gastrointestinal tract. Exemplary thickening agents include acacia, alginic acid bentonite, carbomer, carboxymethylcellulose calcium or sodium, cetostearyl alcohol, methyl cellulose, ethylcellulose, glycerin, gelatin guar gum, hydroxyethyl cellulose, hydroxymethyl cellulose, hydroxypropyl cellulose, hydroxypropyl methyl cellulose ("HPMC"), any other suitable cellulose-based component, maltodextrin, polyvinyl alcohol, povidone, propylene carbonate, propylene glycol alginate, sodium alginate, sodium starch glycolate, starch tragacanth, and xanthan gum, or a combination thereof. Thickening agent, when included, can be present in an amount of about 0.1 volume percent to 20 volume percent (v/v), based on the total volume of the solution. In one example, glycerin can be present in an amount of about 1 volume percent to 10 volume percent (v/v), based on the total volume of the solution. Exemplary amounts of thickening agent include from about 1 volume percent to 12 volume percent (v/v), and preferably at an amount of about 4 volume percent to 10 volume percent (v/v), based on the total volume of the solution. An exemplary amount includes about 6 to 10 volume percent (v/v). In some instances, a sweetening agent can be optionally included in the oral liquid dosage form. Exemplary sweetening agents include sorbitol, saccharin, acesulfame, e.g., acesulfame potassium, sucralose, xylitol, maltitol, sucrose, aspartame, fructose, neotame, glycerin, sodium saccharate, glycyrrhizin dipotassium, acesulfame K, mannitol, invert sugar, and combinations thereof, or components containing a sweetening agent, such as one or more sucralose-containing components or saccharin-containing components, can be added to modify the taste of the composition. Alternatively, or in addition, a viscous sweetener such as one or more of a sorbitol solution, a syrup (sucrose solution), or high-fructose corn syrup can be used and, in addition to sweetening effects, can be useful to increase viscosity and to retard sedimentation. In some instances, the sweetening agent includes an acesulfame-containing, sucralose-containing, or saccharin-containing component. In some instances, the sweetening agent includes glycerin, saccharin, liquid sugar (sucrose solution), or a combination thereof. Such a sweetening agent, if present, can be present in an amount sufficient to minimize or mask any off-flavors in the taste of the active agents, and also to minimize or mask any other off-flavor components included in the formulation if desired. Sweetening agent(s), when included, can be present in an amount of about 0.1 volume percent to 85 volume percent (v/v), based on the total volume of the solution. In one example, the sweetening agent can be present in an amount of about 5 volume percent to 70 volume percent (v/v), based on the total volume of the solution. Exemplary amounts of glyercin include about 2 volume percent to 18 volume percent (v/v), preferably about 5 volume percent to 10 volume percent (v/v). In some instances, exemplary amounts of liquid sugar include about 40 volume percent to 75 volume percent (v/v), preferably about 60 volume percent to 70 volume percent (v/v), based on the total volume of the solution. In some instances, certain types of thickening agent or sweetening agent act as a solubilizing agent or a stabilizing agent, or both, or have other properties, when included as a component of a pharmaceutically acceptable carrier. For example, a sweetening agent such as glycerin acts as a thickening agent. In some instances, an oral liquid dosage form contains, in addition to a sweetening agent, a flavoring agent, for example, one or more of natural and artificial fruit, artificial banana, strawberry, and pineapple. In some instances, a colorant agent, when included in the liquid dosage form, can be provided in an amount sufficient to provide the compositions with a more aesthetic and/or distinctive appearance. Exemplary colorant agents include one or more synthetic organic food additives (e.g., food dyes such as food red dye Nos. 2 and 3, food yellow dye Nos. 4 and 5 and food blue dye Nos. 1 and 2), water-insoluble lake dyes (e.g., aluminum salts of the above synthetic organic food additives, etc.), and natural pigments (e.g., beta-carotene, chlorophyll, iron oxide red, etc.). Other suitable colorants include D&C Red No. 33, FD&C Red No. 3, FD&C Red No. 40, D&C Yellow No. 10, and C Yellow No. 6, or any combination of these or the above colorants. In some instances, suitable preservative agent(s) are optionally included in the liquid dosage form. The preservative agent(s) can be in an amount sufficient to extend the shelf-life or storage stability, or both, of the liquid dosage form. Exemplary preservative agents include sodium benzoate, paraoxybenzoic acid esters, methyl, ethyl, butyl, and propyl parabens, chlorobutanol, benzyl alcohol, phenylethylalcohol, dehydroacetic acid, sorbic acid, benzalkonium chloride (BKC), benzethonium chloride, phenol, phenylmercuric nitrate, thimerosal, and a combination thereof. In some instances, the pH of the liquid dosage form can be adjusted by a buffering agent. The buffering agent can be present in an amount sufficient to buffer the pH of the solution and minimize degradation of the active ingredients. In some instances, some buffering agents also modulate active ingredient solubility in the liquid dosage form. Exemplary buffering agents include one or more of gluconate, lactate, citrate, acetate, phosphate, benzoate, and/or carbonate salts. The pH can be adjusted with a combination of two or more of these buffering agents, e.g., citric acid and sodium benzoate. The buffering agent can be present as a buffer solution. In another example, the buffering agent includes a phosphate, such as a potassium phosphate or sodium phosphate, or a combination thereof. In some instances, emulsifying agents can be included in the liquid dosage form in an amount sufficient to facilitate more uniform dispersion of one or more active ingredients or other pharmaceutically acceptable excipient that can be not generally soluble in the liquid. Exemplary emulsifying agents include gelatin, egg yolk, casein, cholesterol, acacia, tragacanth, chondrus, pectin, methyl cellulose, carbomer, cetostearyl alcohol, cetyl alcohol, or a combination thereof. Solubilizing agents can be included in the liquid dosage form, e.g., in an amount sufficient to facilitate greater or more rapid dissolution of one or more active ingredients or other excipients. Exemplary solubilizing agents include an alcohol, e.g., 95% ethyl alcohol, a glycol, glycerin, D-mannitol, trehalose, benzyl benzoate, trisaminomethane, cholesterol, triethanolamine, sodium carbonate, sodium citrate, sodium salicylate, sodium acetate, and a combination thereof. Exemplary alcohols include ethanol, isopropanol, t-butanol, phenol, cresol, a benzyl alcohol, or a combination thereof. Exemplary glycols include C2-20 alkenes functionalized with a glycol, including propylene glycol, polypropylene glycol, polyethylene glycol, etc., or a combination thereof. A solubilizing agent can be included in an amount of about 1 volume percent to 20 volume percent (v/v), or about 4 volume percent to 15 volume percent (v/v), based on the total volume of the solution. Exemplary amounts of solubilizing agent include about 7 volume percent to 12 volume percent (v/v) based on the total volume of the solution. In some instances, a stabilizing agent can be included in the liquid dosage form. Exemplary stabilizing agents include, for example, one or more liquid excipients such as ethanol, glycerin; one or more glycols, such as polyethylene glycol, e.g., PEG-400, propylene glycol, or polypropylene glycol; a cellulose-based component, such as hydroxypropylmethylcellulose (HPMC) or hydroxymethylcellulose (HMC); or any combination thereof. In some instances, certain solubilizing agents function effectively as a stabilizing agent. For example, propylene glycol functions as both a solubilizing agent and as a stabilizing agent. In some instances, an antioxidant(s) can be included in the liquid dosage form. Exemplary antioxidants include one or more flavonoids, anthocyanidins, anthocyanins, proanthocyanidins, and combinations thereof. The antioxidant(s), when used, can help provide long term stability to the liquid compositions, e.g., at ambient conditions for at least about one month, preferably for at least about 3 months, at least about 24 months, or longer, depending on the type and concentration of antioxidant used and depending on other components of the storage microenvironment, such as pH, buffering agent, etc.

In some instances, a composition disclosed herein exhibits improved or more desired performance with respect to drug concentration, dissolution, dispersion, stability, safety, emulsification, efficacy, flavor, patient compliance, bioavailability, and/or other pharmacokinetic, chemical and/or physical properties. In some instances, an effective amount of one or more active agents can be dissolved to generate a substantially stable, or stable, solution with one or more of the pharmaceutically acceptable carriers or excipients as disclosed herein. In some instances, an oral liquid dosage form disclosed herein can be a controlled-release oral liquid dosage form. The controlled release oral liquid dosage form can provide for controlled or sustained release of one or more active ingredients from a gel, matrix, capsule, or resin material, or any combination of controlled or sustained release technology that can be suspended or dissolved in a liquid composition. In some instances, the controlled-release oral liquid dosage form can comprise one or more excipients such as xanthan gum, sodium alginate, complex coacervate pairs such as gelatin or other polymers and carrageenan, and thermal gelling methycellulose formulations. Such excipients can influence the dissolution and/or diffusion rate of a suspended active ingredient so as to modify the absorption characteristics of the active ingredient as compared to a conventional oral liquid dosage form. In some instances, the controlled-release oral liquid dosage form can be administered in a normally liquid composition and only subsequently forms a semi-solid or gel-like persistent matrix in the environment of the stomach. In some instances, a controlled-release oral liquid dosage form can comprise an aqueous, partially aqueous or non-aqueous solution or suspension of xanthan gum, sodium alginate, or sodium alginate LV (low viscosity, calcium depleted), gelatin and carrageenan, methylcellulose, or a combination thereof. In some instances, the controlled-release oral liquid dosage form can comprise xanthan gum (e.g., Kelco SS-4749 and other commercially available types) in an amount of from about 0.3 to about 3.0 percent by weight. In some instances, the controlled-release oral liquid dosage form can comprise xanthan gum in an amount of about 1.0 percent by weight. In some instances, the controlled-release oral liquid dosage form can comprise sodium alginate in an amount of from about 0.5 to about 3.0 weight percent, or from about 0.3 to about 1.5 percent by weight of each gelatin and carrageenan. In some instances, each carrageenan of the iota type and gelatin type B can be present at levels of at least about 0.5 percent by weight. In some instances, the controlled-release oral liquid dosage form can comprise at least about 1 weight percent of sodium alginate. In some instances, the controlled-release oral liquid dosage form can comprise methylcellulose (e.g., Type A15C, Dow Chemical Co.) in an amount of from about 1.0 to about 3.0 weight percent. In some instances, the controlled-release oral liquid dosage form can comprise methylcellulose (e.g., Type A15C, Dow Chemical Co.) in an amount of about 2.0 weight percent. In some instances, the controlled-release oral liquid dosage form comprise other excipients such as, for example, locust bean gum, salts such as NaCl, sugars such as sorbitol, $Na_3PO_4$, $CaCO_3$, $Ca_2HPO_4$ and the like. The controlled-release oral liquid dosage form can comprise carbonate compounds such as calcium carbonate. The calcium carbonate can "float" the gelatinous matrix in a predetermined region of the stomach so that it can be contacted with the most appropriate pH environment for a prolonged time period due to delayed gastric emptying. In some instances, the controlled-release oral liquid dosage form includes aqueous solutions or suspensions, partially aqueous solutions or suspensions such as, for example, high or low molecular weight glycerin, alcohols and glycols or even non-aqueous solutions or suspensions such as, for example, high or low molecular weight glycerin, alcohols and glycols.

In some instances, a liquid composition disclosed herein further can comprise one or more excipients: acorbic acid, EDTA dihydrate, glycerine, citric acid monohydrate, sodium citrate dihydrate, sorbitol solution (e.g., 70%), sucralose, food color (e.g., FD&C Yellow #6), food or fruit flavor (e.g., artificial or natural orange flavor), mint flavor (e.g., artificial or natural peppermint flavor), or water. In some instances, the liquid composition further can comprise one or both of sodium benzoate and sodium proionate. In some instances, the liquid composition further can comprise one or more of propylparaben, methylparaben, or propylene glycol. In some instances, the liquid composition further can comprise pseudoephedrine or a pharmaceutically acceptable salt thereof (e.g., pseudoephedrin HCl).

Methods of Making Liquid Compositions

In one aspect, a method for preparing a liquid composition disclosed herein includes blending one or more beads having one or more active agents with a dense, thixotropic solution having a density that can be at or about the density of the one or more beads and a thixotropic agent, water and one or more preservatives under conditions that reduce bubble formation. In another aspect, a method for preparing a liquid composition includes blending a mixture comprising one or more beads comprising one or more active agents, a thickening agent and a surfactant by mixing with a low cavitation propeller and recirculating the mixture under the surface of the mixture so as to minimize bubble formation. In another aspect, a method for preparing a liquid composition includes blending a mixture comprising one or more active agents on or about a carrier a thickening agent under conditions that minimize the introduction of air. The conditions that minimize, reduce and/or eliminate the introduction of air and/or air bubbles include one or more of the following steps used alone, in combination and/or in any order: using a diaphragm pump to combine, e.g., the water and the thixotropic agent and one or more preservatives, colorants and flavorants; placing the recirculating tube below the surface of the liquid; adding liquids along the side of a vessel holding the liquid; sprinkling beads (e.g., one or more beads that includes one or more active agents) onto the surface of the liquid; mixing the solution in the absence of one or more paddles that scrape the vessel; mixing the solution with a propeller mixer; mixing the solution with a propeller mixer at a speed that reduces or minimizes cavitation and combinations of two or more of these steps. In another aspect, a method for preparing a liquid composition includes blending a mixture of one or more controlled-release beads with one or more active agents on a carrier in a solution having a low ionic concentration and a thixotropic agent, under conditions that minimize the introduction of air bubbles.

As used herein, the term "thixotropic" can be used to describe one or more agents, e.g., certain gels, which liquefy when subjected to vibratory forces like simple shaking, and then solidify again when left standing. Thixotropic behavior can be observed when long-chain molecules tend to orient themselves in the direction of flow; as the applied force can be increased, the resistance to flow can be decreased. Yet when high shear stress can be removed, the solution will quickly revert to its original viscous state. Some celluloses exhibit thixotropic behavior wherein the solution returns to its viscous state over a period of time. Examples of thixotropic agents include cellulose (e.g., carboxymethylcellulose), gums (e.g., xanthan), collagen, gelatin, and aerogels.

In some instances, when formulated with particles, e.g., microparticles or nanoparticles, the release profile of one or more active agents are easily be adapted by adding a coating, e.g., a hard or soft gelatin coating, a starch coating, a resin or polymer coating and/or a cellulosic coating. Although not limited to microparticles or nanoparticles (as in, e.g., microcapsules or nanocapsules), such dosage forms can be further coated with, for example, a seal coating, an enteric coating, an extended release coating, or a targeted delayed release coating. A coating can be applied to an active that can be compressed, molded or extruded. A coating can be applied through an aqueous dispersion or after dissolving in appropriate solvent.

In some instances, a carrier disclosed herein can be fully or partially biodegradable. Exemplary carriers include permeable and semipermeable matrices or polymers that control the release characteristics of the formulation. Such polymers include, for example, cellulose acylates, and acetates, as well as the selectively permeable polymers formed by the coprecipitation of a polycation and a polyanioni. Other carriers include, e.g., starch, modified starch, and starch derivatives, gums, including but not limited to xanthan gum, alginic acid, other alginates, benitoniite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan (and derivatives), gum karaya, biosynthetic gum, etc. Other useful polymers include: polycarbonates (linear polyesters of carbonic acid); microporous materials (bisphenol, a microporous poly(vinylchloride), micro-porous polyamides, microporous modacrylic copolymers, microporous styrene-acrylic and its copolymers); porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly (urethane), cross-linked chain-extended poly(urethane), poly(imides), poly(benzimidazoles), collodion, regenerated proteins, semi-solid cross-linked poly(vinylpyrrolidone). Additional additives and their levels, and selection of a primary coating material or materials will depend on the following properties: resistance to dissolution and disintegration in the stomach; impermeability to gastric fluids and drug/carrier/enzyme while in the stomach; ability to dissolve or disintegrate rapidly at the target intestine site; physical and chemical stability during storage; non-toxicity; easy application as a coating (substrate friendly); and economical practicality.

Treatments and Uses

In some cases, the present disclosure provides a method of inhibiting or killing one or more bacteria, comprising contacting the antibiotic composition disclosed herein with the one or more bacteria. In some cases, the present disclosure provides a method of treating a bacterial infection, comprising contacting the antibiotic composition disclosed herein with the bacterial infection. In some instances, the one or more bacteria comprise one or more Gram-negative bacteria. In some instances, the one or more bacteria comprise one or more multidrug-resistance Gram-negative bacteria. In some instances, the one or more bacteria can comprise *K. pneumonia, A. baumannii, P. aeruginosa, E. cloacae, E. coli*, or any combination thereof. In some instances, the bacterial infection or one or more bacteria can be on a surface. In some instances, the bacterial infection or one or more bacteria can be in a mammal. In some instances, the bacterial infection or one or more bacteria can be in a human. In some instances, the contacting can be by injection, for example intravenous or subcutaneous injection. In some instances, the contacting can be by topical application. In some instances, the contacting can be by mouth. In some instances, the contacting lasts for at least about: 1 minute, 2 minute, 3 minutes, 4 minutes, 5 minutes, 10 minutes, 20 minutes, 30 minute, 40 minutes, 50 minutes, 1 hour, 2 hours, 3 hours, 4 hours, 5 hours, 6 hours, 7 hour, 8 hours, 9 hours, 10 hours, 11 hours, 12 hours, 18 hours, one day, two days, three days, four days, five days, six days, one week, or one month. In some instances, the contacting occurs 1, 2, 3, 4, 5, 6, 7, or 8 times hourly or daily. In some instances, the contacting occurs about every 3, 4, 5, 6, 7, 8, 9, 10, 11, or 12 minutes or hours daily. In some instances, the antibiotic composition can be in a single unit dose. In some instances, the amount of the organoselenium agent contacted with the bacterial infection or one or more bacteria can be about 10 to 100 mg, about 10 to 50 mg, or about 20 to 30 mg, for example about 25 mg, per dosage. In some instances, an amount of the silver contacted with the bacterial infection or one or more bacteria can be about 1 to 20 mg, about 1 to 10 mg, or about 5 to 7 mg, for example about 6 mg, per dosage.

In some instances, an antibiotic composition disclosed herein can be used to treat or prevent bacterial infections or viral infection, and in some instances, protozoan infections. In some instances, the treatment inhibits or kills one or more bacteria. In some instances, the antibiotic composition can be given as a preventive measure (prophylactic) to at-risk populations such as those with a weakened immune system (particularly in HIV cases to prevent pneumonia), those taking immunosuppressive drugs, cancer patients and those having surgery. In some instances, the antibiotic composition can be used in surgical procedures to help prevent infection of incisions made. In some instances, the antibiotic composition can be used in dental antibiotic prophylaxis to prevent bacteremia and consequent infective endocarditis. In some instances, the antibiotic composition can be used to prevent infection in cases of neutropenia particularly cancer-related.

In some instances, the antibiotic composition can be applied orally, topically, or by injection, e.g., intravenously, subcutaneously, or intramuscularly. In some instances, the antibiotic composition can be given topically, for example for some skin conditions including acne and cellulitis, or in the form of eye drops onto the conjunctiva for conjunctivitis or ear drops for ear infections and acute cases of swimmer's ear. In some stances, advantages of topical application include achieving high and sustained concentration of antibiotic at the site of infection; reducing the potential for systemic absorption and toxicity, and total volumes of antibiotic required are reduced, thereby also reducing the risk of antibiotic misuse. In some instances, the antibiotic composition can be applied topically over certain types of surgical wounds to reduce the risk of surgical site infections.

In some instances, an antibiotic composition disclosed herein, such as in a form of coating, are used to sterilize a surface. For example, the antibiotic composition can be applied to surgical equipment, and any surface in contact with surgical equipment, prior to an operation. Scientific equipment can also be coated with such antibiotic composition to prevent cross contamination of certain microbes that could interfere with a measurement to be taken with the equipment. In some cases, the antibiotic composition can be applied in the form of a film, sheet, liquid, aerosol, or coating to a biological or non biological surface. Further applications can include adhering an antibiotic composition onto a transplanted organ to prevent infection by a pathogen during a transplant process.

In some instances, a subject suitable for the treatment can be a surface. In some instances, a subject suitable for the treatment can be a mammal, e.g., a human, mouse, rat, guinea pig, dog, cat, horse, cow, pig, or non-human primate, such as a monkey, chimpanzee or baboon. In some instances, the subject can be a human. In some instances, the subject can be an adult. In some instances, the subject can be a child. In some instances, the subject can be 2 years of age or older, 4 years of age or older, 6 years of age or older, 12 years of age or older, or 18 years of age or older. In some instances, a subject suitable for the treatment can be younger than 18 years of age, 12 years of age, or 6 years of age.

In some instances, compositions disclosed herein are administered to a subject at about every 4 to about 6 hours, about every 12 hours, about every 24 hours, about every 48 hours, or more often. In some instances, a composition disclosed herein can be administered once, twice, three times, four times, five times, six times, seven times, eight times, or more often daily. In some instances, a dosage form disclosed herein provides an effective plasma concentration of an active agent at from about 1 minute to about 20 minutes after administration, such as about: 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min. In some instances, a dosage form of the disclosure herein provides an effective plasma concentration of an active agent at from about 20 minutes to about 24 hours after administration, such as about 20 minutes, 30 minutes, 40 minutes, 50 minutes, 1 hr, 1.2 hrs, 1.4 hrs, 1.6 hrs, 1.8 hrs, 2 hrs, 2.2 hrs, 2.4 hrs, 2.6 hrs, 2.8 hrs, 3 hrs, 3.2 hrs, 3.4 hrs, 3.6 hrs, 3.8 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 23 hrs, or 24 hrs following administration. In some instances, the active agent can be present in an effective plasma concentration in a subject for about 4 to about 6 hours, about 12 hours, about 24 hour, or 1 day to 30 days, including but not limited to 1, 2, 3, 4, 5, 6, 7, 8, 9, 10, 12, 12, 13, 14, 15, 16, 17, 18, 19, 20, 21, 22, 23, 24, 25, 26, 27, 28, 29 or 30 days.

In some instances, an antibiotic composition disclosed herein inhibits or kills one or more multidrug-resistant bacteria. In some instances, an antibiotic composition disclosed herein inhibits or kills one or more Gram-positive bacteria or Gram-negative bacteria. In some instances, an antibiotic composition disclosed herein inhibits or kills one or more multidrug-resistant Gram-positive bacteria. In some instances, an antibiotic composition disclosed herein inhibits or kills one or more multidrug-resistant Gram-negative bacteria, which have nonsusceptibility to at least one agent in three or more antimicrobial categories. In some instances, an antibiotic composition disclosed herein inhibits or kills one or more bacteria, including *Bacillus cereus* var *mycoides*, *Escherichia coli*, *Pseudomonas aeruginosa*, *Staphylococcus aureus*, *Streptococcus faecalis*, *Aspergillus niger*, *Aureobasiduim pullulans*, *Chaetomium globosum*, *Gliocladium virens*, *Penicillum funiculosum*, *Candida albicans*, *Acinetobacter baumannii*, Enterobacteriaceae, cocci, bacilli, vancomycin-resistant enterococci, or *Saccharomyces cerevisiae*. In some instances, an antibiotic composition disclosed herein inhibits or kills one or more Gram-negative bacteria, including *K. pneumonia*, *A. baumannii*, *P. aeruginosa*, *E. cloacae*, *E. coli*, or any combination thereof. In some instances, an antibiotic composition disclosed herein inhibits or kills one or more of *Escherichia coli* (*E. coli*), *Salmonella*, *Shigella*, and other Enterobacteriaceae, *Pseudomonas*, *Moraxella*, *Helicobacter*, *Stenotrophomonas*, Bdellovibrio, acetic acid bacteria, *Legionella*, cyanobacteria, spirochaetes, green sulfur, and green non-sulfur bacteria. In some instances, the antibiotic composition disclosed herein exhibits a 50% inhibitory concentration (IC50) of less than about: 50 µM, 25 µM, 20 µM, 10 µM, 5 µM, 1 µM, 0.5 µM, 0.1 µM, 50 nM, 25 nM, 20 nM, 10 nM, 5 nM, or 1 nM to one or more bacteria.

In some instances, an antibiotic composition disclosed herein treats infection caused by one or more organism(s) that are species of *Staphylococcus* (e.g., *Staphylococcus aureus*, *Staphylococcus epidermidis*), *Streptococcus* (e.g., *Streptococcus viridans*, *Streptococcus pneumoniae*), *Enterococcus*, *Bacillus*, *Corynebacterium*, *Propionibacterium*, *Chlamydia*, *Moraxella*, *Haemophilus* and *Neisseria*. In some instances, the species are *Staphylococcus aureus*, *Staphylococcus epidermidis*, *Streptococcus pneumoniae*, *Streptococcus pyogenes*, *Streptococcus viridans*, *Enterococcus faecalis*, *Corynebacterium* sp., *Propionibacterium* sp., *Moraxella catarrhalis* and *Haemophilus influenzae*.

In some instances, an antibiotic composition disclosed herein can be suitable for topical administration to an eye, such as a form of eye drop or eye cream, the composition comprising: a combination of active agents in a concentration effective for treatment and/or prophylaxis of a gram-positive or gram-negative bacterial infection of at least one tissue of the eye, and at least one ophthalmically acceptable excipient that reduces a rate of removal of the composition from the eye by lacrimation.

In some instances, an antibiotic composition disclosed herein penetrates or dissolves a microbial biofilm. A microbial biofilm, also referred to as a biological biofilm, can be a community of microbial cells embedded in an extracellular matrix of polymeric substances and adherent to a biological or a non-biotic surface. A range of microorganisms (bacteria, fungi, and/or protozoa, with associated bacteriophages and other viruses) can be found in these biofilms. Biofilms are ubiquitous in nature, are commonly found in a wide range of environments. Biofilms are being increasingly recognized by the scientific and medical community as being implicated in many infections, and especially their contribution to the recalcitrance of infection treatment. Biofilms can be etiologic agents for a number of disease states in mammals and are involved in 80% of infections in humans. Examples can include skin and wound infections, middle-ear infections, gastrointestinal tract infections, peritoneal membrane infections, urogenital tract infections, oral soft tissue infections, formation of dental plaque, eye infections (including contact lens contamination), endocarditis, infections in cystic fibrosis, and infections of indwelling medical devices such as joint prostheses, dental implants, catheters and cardiac implants. Microbes in biofilms can be significantly more resistant to antimicrobial treatment than their planktonic counterparts. Biofilm formation is not limited solely to the ability of microbes to attach to a surface. Microbes growing in a biofilm can interact more between each other than with the actual physical substratum on which the biofilm initially developed.

EXAMPLES

Figure 1A:
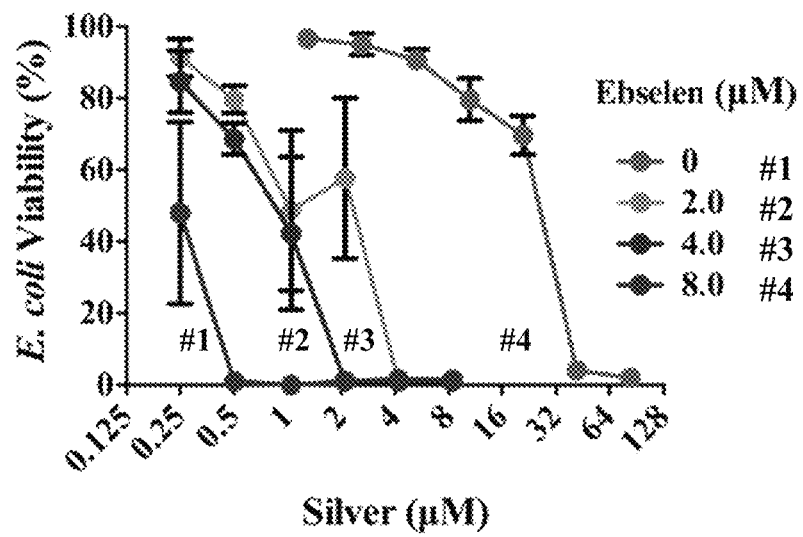
FIGS. 1A and 1B illustrate effects of silver with ebselen in combination on the growth of E. coli and HeLa Cells.
Figure 1B:
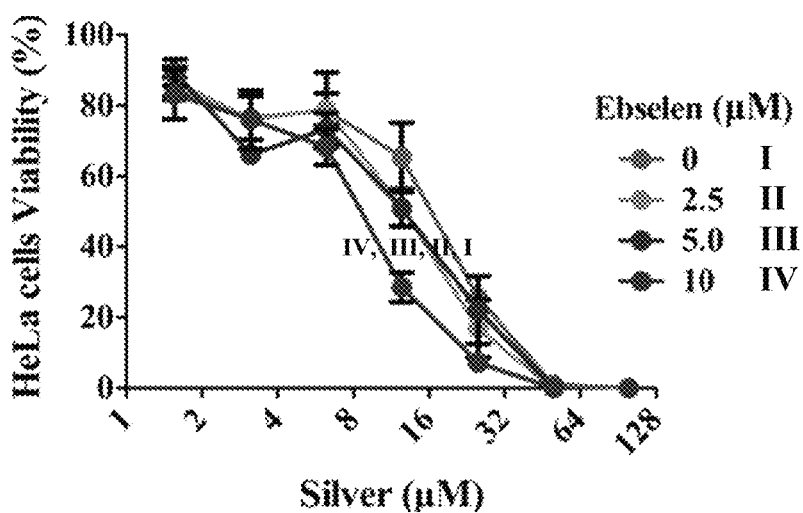
Figure 1C:
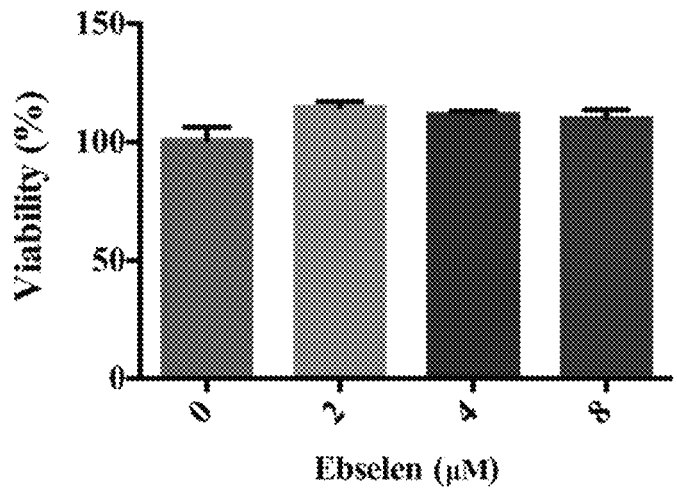
FIG. 1C is a bar chart showing that ebselen alone has no effect on the growth of E. coli. E. coli DHB4 overnight cultures were diluted 1:1000 into 100 µl of LB medium in 96 micro-well plates and treated with different concentrations of ebselen for 16 h. The cell viability was determined by measuring the absorbance at 600 nm. Data are presented as means±s. d. of three independent experiments. *: p<0.05, : p<0.01, *: p<0.001 (t-test).

Example 1. In Vitro Experiments 1.1 Results
Combination of Silver with Ebselen Exhibited Selective Synergistic Toxicity Against Bacteria The effect of silver nitrate with ebselen in combination on the growth of Gram-negative model bacteria, E. coli, was investigated in the microplates. DHB4 overnight cultures were diluted 1:1000 times in Luria-Bertani (LB) medium, and treated with ionic silver ($Ag^+$) as a nitrate salt ($AgNO3$) for 16 h. $Ag^+$ alone inhibited E. coli growth with a minimal inhibition concentration (MIC) of 42 μM after 16 h treatment, while the addition of 2 μM ebselen dramatically decreased the MIC of $Ag^+$ to 4.2 μM ($p=0.000028<0.001$) (FIG. 1A). Meanwhile, 5 μM $Ag^+$ and 2.5 μM ebselen in combination showed no synergistic toxicity on human HeLa cells ($p=0.98>0.05$) (FIG. 1B). In addition, the toxicity of ebselen itself (2, 4, 8 μM) on bacterial and mammalian cells was similar (FIGS. 1A and 1B) with no effects on bacterial growth (FIG. 1C). These results indicate that treatment of $Ag^+$ with ebselen in combination exhibits significant selective synergistic toxicity on bacteria over mammalian cells, and the dramatic decrease of MIC of silver against bacteria in the presence of ebselen make the systemic medical use of silver feasible.

Figure 2A:
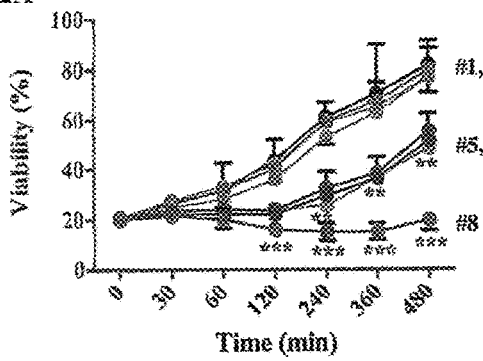
FIGS. 2A to 2D illustrate silver with ebselen in combination exhibited synergistic bactericidal effect. E. coli DHB4 grown to $OD_{600\ nm}$ of 0.4 were treated with serial dilutions of ebselen and AgNO3 in combination.
Figure 2B:
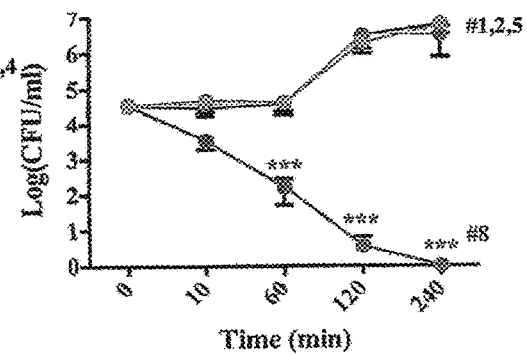
Figure 2C:
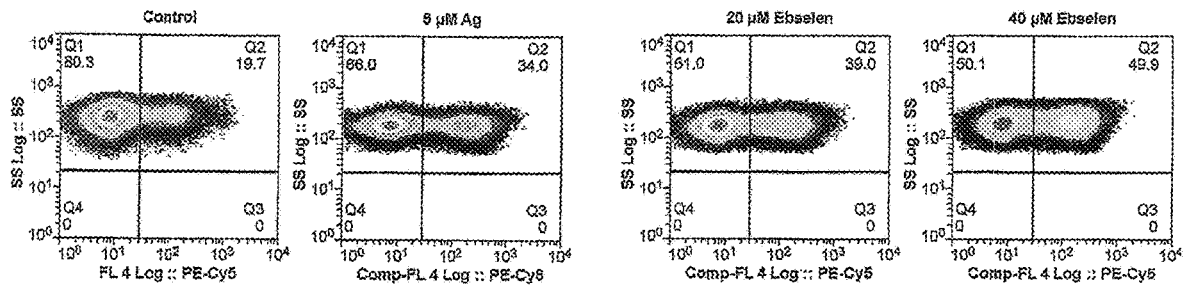
Figure 2C:
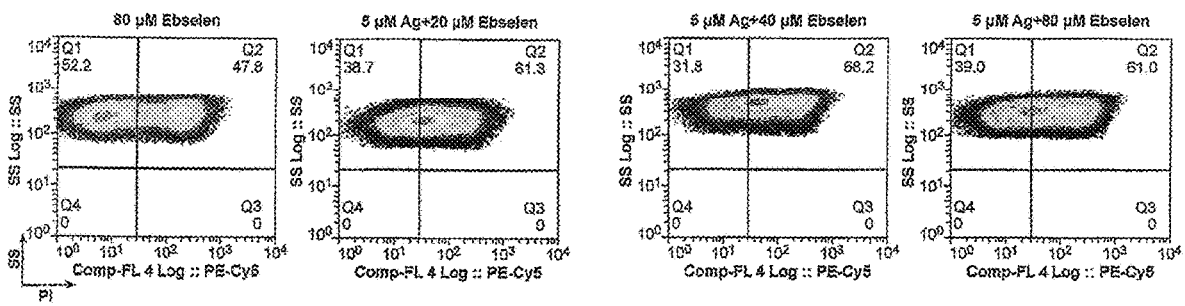
Figure 2D:
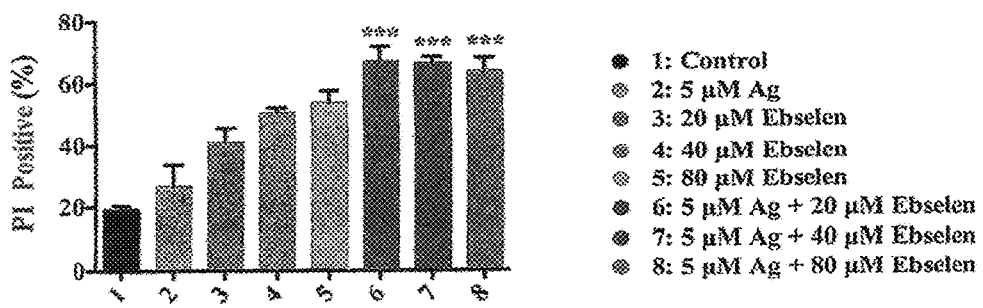

The large scale growth inhibition of E. coli by $Ag^+$ with ebselen in combination was also observed in shaking testing 15 ml tubes. E. coli DHB4 cells were grown until an $OD_{600\ nm}$ of 0.4, and treated with 5 μM $Ag^+$ and serial concentrations of ebselen (0, 20, 40, 80 μM). The growth curves showed a synergistic bacteriostatic effect of Ag+ with ebselen in combination in LB medium (FIG. 2A), and the synergistic bactericidal effect of 5 μM Ag+ and 80 μM ebselen in combination was further confirmed by the colony formation assay on LB-agar plates (FIG. 2B). Meanwhile, only 80 μM ebselen itself could inhibit E. coli growth in first 8 h, and gains back into normal 12 h post-treatment. While 40 μM ebselen or 5 μM $Ag^+$ alone did not inhibit bacterial growth, $Ag^+$ with ebselen in combination resulted in strong inhibition of E. coli growth (FIGS. 2A and 2B). In line with this, 5 μM Ag+ and 20 μM ebselen in combination enhanced the frequency of propidium iodide (PI) staining ($p=0.00083<0.001$) (FIGS. 2C and 2D). PI is a membrane-impermeable fluorescent dye that has been widely used to detect permeation of cell membrane and dead cells. Above all, these results indicate that $Ag^+$ and ebselen in combination exhibited a selective synergistic effect on bacteria.

Clinically Isolated Five Most Difficult-to-Treat MDR Gram-Negative Pathogens were Sensitive to $Ag^+$ with Ebselen in Combination There are five most difficult-to-treat MDR Gram-negative pathogen species in the clinic, which are also typical GSH-positive bacteria: Klebsiella pneumonia, Acinetobacter baumannii, Pseudomonas aeruginosa, Enterobacter cloacae and Escherichia coli. Two strains of each species were isolated, overnight cultures were diluted 1:1000 times in LB medium, and treated with $Ag^+$ with a serial concentration of ebselen in combination for 16 h. The synergistic bactericidal effects of $Ag^+$ with ebselen in combination against all 10 tested strains were observed (Table 1). Among these five species, A. baumannii and E. cloacae are very readily formed drug-resistant strains, which are needed to be treated by or the fourth-generation cephalosporin in the clinic, including imipenem, cefepime, and cefotaxime, etc. The isolated imipenem, cefepime, and cefotaxime-resistant A. baumannii (AB-1/2) and E. cloacae (ECL-1) strains were identified (Table 2, and 3), and were sensitive to $Ag^+$ with ebselen in combination (Table 1). These results indicate that $Ag^+$ with ebselen in combination might be 'the last life-saving straw' that are active against a range of bacteria with existing resistance, which would increase the correct chance for empirically-prescribed therapy, even for infections resistant to conventional antibiotics.

Figure 3A:
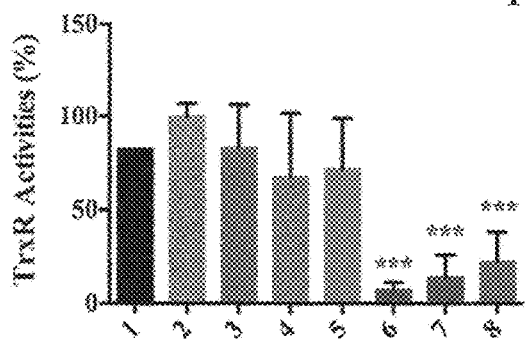
FIGS. 3A to 3F illustrate silver with ebselen in combination directly disrupted bacterial Trx and GSH systems. E. coli DHB4 grown to $OD_{600\ nm}$ of 0.4 were treated with serial dilutions of ebselen and AgNO3 in combination.
Figure 3B:
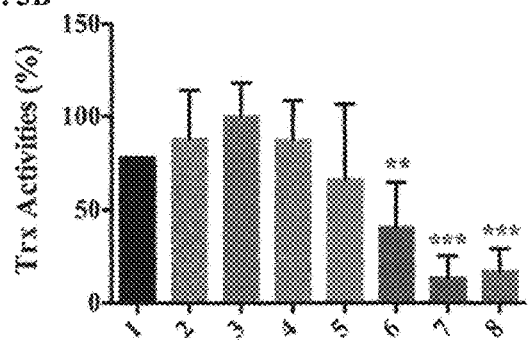
Figure 3C:
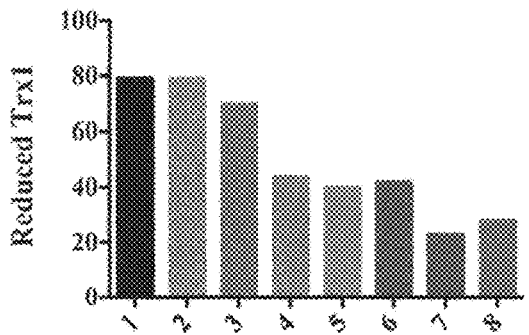
Figure 3E:
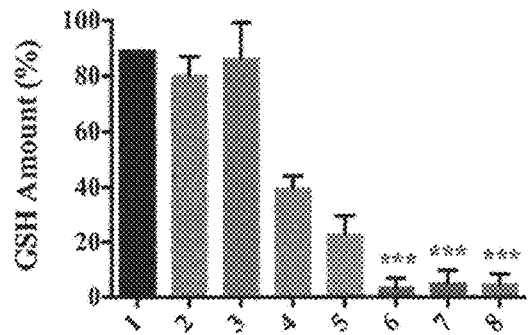
Figure 3D:
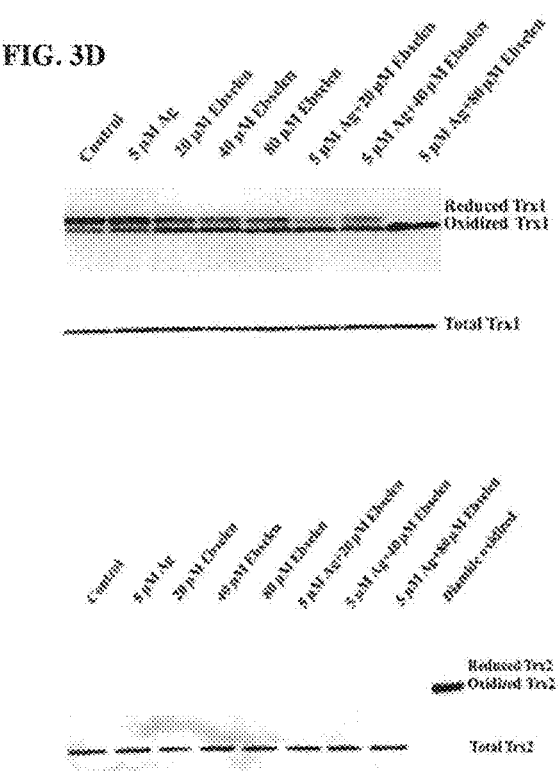

$Ag^+$ with Ebselen in Combination Directly Disrupted Bacterial Trx and GSH Systems Since $Ag^+$ and ebselen are generally thought to be thiol-targeting agents, bacterial TrxR or Trx activity in cells were treated by $Ag^+$ with ebselen in combination (FIGS. 3A and 3B). While TrxR and Trx activities in cell extracts were not influenced by either $Ag^+$ or ebselen alone, 5 μM $Ag^+$ and 20 μM ebselen in combination resulted in a dramatic loss of TrxR ($p=0.00018<0.001$) and Trx ($p=0.0036<0.01$) activities (FIGS. 3A and 3B). Consistent with this observation, the redox state of Trx1 measured by Redox Western Blot was also affected by treatment of $Ag^+$ with ebselen in combination. Trx1 was mostly in reduced form in untreated bacteria, which became oxidized upon treatment of drugs in combination (FIG. 3C). A Trx2 antibody was used to detect oxidized Trx2 in the experiment to investigate the effect of treatment on the redox state of Trxs. Reduced Trx2 could not be detected by this antibody probably because of the blockage of the recognition site. None of the oxidized Trx2 was observed upon the treatment, while the positive control diamide-oxidized Trx2 was detected (FIG. 3D). These results showed that Trx2 was less sensitive to the treatment compared to Trx1. In addition, the protein levels of Trx 1 and 2 were not affected by the 10 min treatment with $Ag^+$ and ebselen combination (FIGS. 3C and 3D).

The addition of 5 μM $Ag^+$ and 20, 40 or 80 μM ebselen also decreased the GSH levels. Five μM $Ag^+$ and 20 μM ebselen in combination treatment depleted the functional GSH in 10 min compared with control ($p=0.000021<0.001$) (FIG. 3E). Ebselen alone at 80 and 40 μM also reduced GSH levels, albeit less efficiently than the corresponding drugs in combination at the same concentration ($p=0.000076$, and $0.000029$, $<0.01$). Instead, neither 5 μM $Ag^+$ nor 20 μM ebselen modulated GSH levels in the conditions tested compared with control ($p=0.081$, and $0.712$, $>0.05$) (FIG. 3E).

Figure 3F:
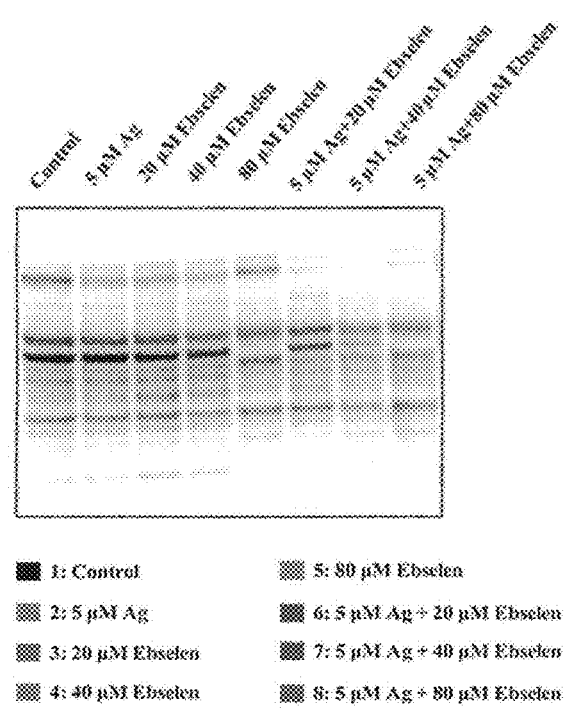

Whether $Ag^+$ with ebselen in combination decreased or depleted GSH could affect proteins S-glutathionylation was further explored (FIG. 3F). Proteins S-glutathionylation was decreased in $Ag^+$ with ebselen treated bacteria, but not in those incubated only with 5 μM $Ag^+$ or 20 μM ebselen alone. Thus the presence of 5 μM $Ag^+$ decreased protein S-glutathionylation when combined with 20 μM ebselen reflecting the loss of GSH (FIG. 3F).

Since Trx and GSH/Grx are major thiol-dependent systems, investigated were the effects of $Ag^+$ with ebselen in combination on Trx or GSH system-deficient E. coli redox mutants. E. coli mutants lacking GSH system components ($gshA^-$) and living on Trx and TrxR were more sensitive to $Ag^+$ and ebselen treatment compared with the wild type (WT) (Table 4-6). All results showed that $Ag^+$ with ebselen in combination has strong synergistic effects on bacterial Trx and GSH systems, and targeting thiol-dependent systems as a novel antibiotic strategy.

Silver Irreversibly Inhibits Bacterial Trx and TrxR Activities

Figure 4A:
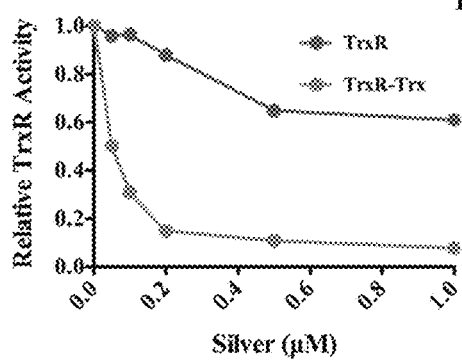
FIGS. 4A to 4D illustrate inhibitory effects of silver on E. coli Trx system in vitro.
Figure 4B:
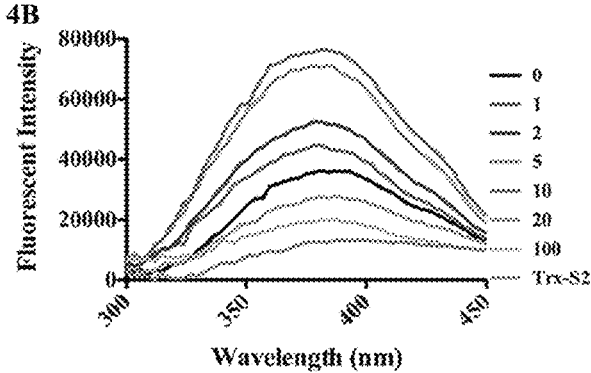
Figure 4C:
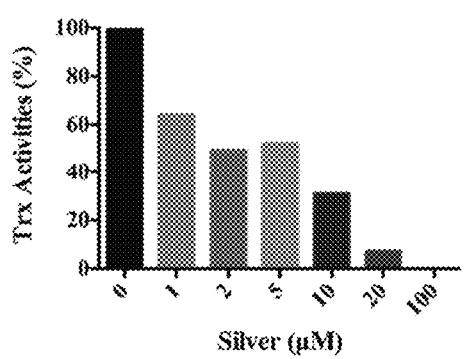
Figure 4D:
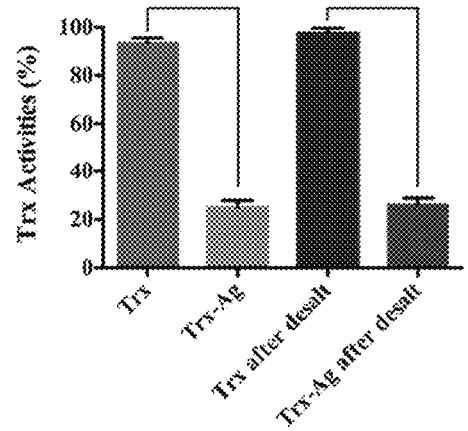

Cellular TrxR and Trx1 enzyme activities were decreased while the corresponding protein levels were unaltered by the treatment of $Ag^+$ with ebselen in combination, suggesting that TrxR and Trx were inhibited. Since ebselen is a known reversible competitive inhibitor of bacterial TrxR, the effect of $Ag^+$ on the activity of *E. coli* TrxR and Trx was investigated. When 100 nM of NADPH-pre-incubated *E. coli* TrxR was incubated with $Ag^+$, the $IC_{50}$ was about 50 nM (FIG. 4A), similar to the gold compound auranofin. To detect whether *E. coli* TrxR can be specifically inhibited by $Ag^+$, the enzyme was incubated with $Ag^+$ in the presence of reduced *E. coli* Trx1, the inhibitory efficiency toward TrxR decreased (FIG. 4A). This indicated that Trx also reacted with $Ag^+$ and played a protective role for the TrxR. Fluorescence spectroscopy further verified that $Ag^+$ interacted with reduced Trx1 and changed its fluorescence spectra (FIG. 4B). Incubation with 1-10 µM $Ag^+$ increased the tryptophan fluorescence intensity of 10 µM Trx1. Meanwhile, the fluorescent intensity of 10 µM Trx1 decreased when treated with 20-100 µM $Ag^+$ (FIG. 4B). In line with this, the activity of Trx decreased along with the increase of $Ag^+$ concentration (FIG. 4C). The inhibition of Trx1 by $Ag^+$ was irreversible since the Trx1 activity was not recovered after desalting (p=0.00021<0.001) (FIG. 4D). This indicated that $Ag^+$ formed a tight complex with the sulfhydryl groups in reduced *E. coli* Trx1. All these results show that silver irreversibly inhibits bacterial Trx and TrxR activities.

Figure 5A:
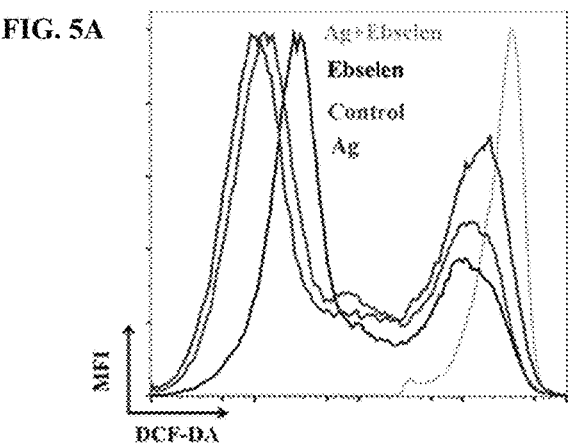
FIGS. 5A to 5C illustrate ROS was a determining factor for synergistic bactericidal effect of silver and ebselen.
Figure 5B:
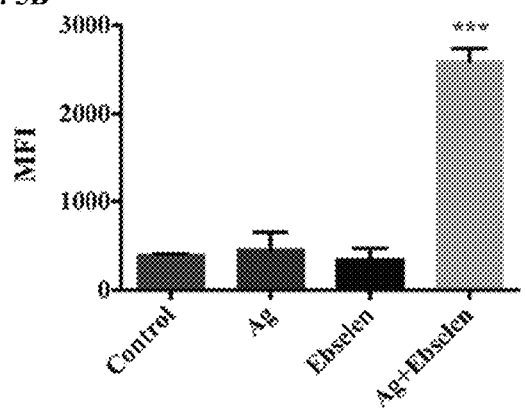
Figure 5C:
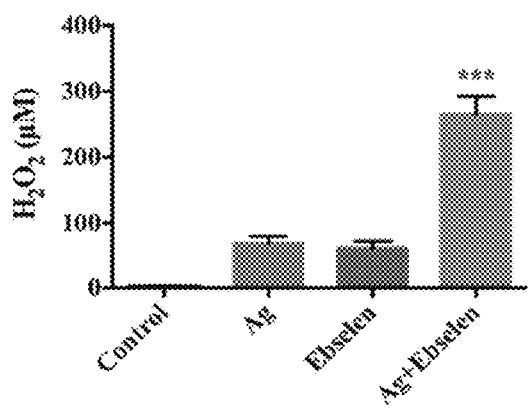

ROS is a Determining Factor for Synergistic Bactericidal Effect of $Ag^+$ and Ebselen One major function of GSH and Trx systems is to scavenge ROS to keep cellular redox balance and protect against oxidative stress. The inhibition of the Trx system and depletion of GSH may responsible for the elevation of ROS. To determine whether increased ROS levels accounted for the bactericidal effect, ROS levels were determined in $Ag^+$ and ebselen treated cells. Treatment with either 5 µM $Ag^+$ or 20 µM ebselen alone did not change ROS concentrations, while the combination of 5 µM $Ag^+$ and 20 µM ebselen resulted in increased levels of ROS (p=0.00012<0.001) (FIGS. 5A and 5B). Further, the enhancement of $H_2O_2$ levels caused by the treatment with 5 µM $Ag^+$ and 20 µM ebselen in combination was also verified by Amplex Red method (p=0.00057<0.0001)(FIG. 5C). In addition, *E. coli* mutants lacking OxyR components ($OxyR^-$) that impair *E. coli* dehydratase clusters from $H_2O_2$ injury were more sensitive to $Ag^+$ and ebselen treatment compared with the wild type (WT) (Table 4-6). All results showed that lethality of $Ag^+$ with ebselen against bacteria is accompanied by ROS generation.

1.2 Materials and Methods

Bacterial Strains

All in vitro experiments were performed with *Escherichia coli* (*E. coli*) DHB4 and its derived redox phenotypes (Table 6), and clinically isolated multidrug-resistance (MDR) Gram-negative strains (Table 2, 3, 7). All in vivo experiments were performed with *E. coli* ZY-1 (Table 7), which was isolated from the urine of clinical patient in the First Affiliated Hospital of Three Gorges University in Hubei Province, P. R. China, with an approval for research from the Ethics Committee of First Affiliated Hospital of Three Gorges University and an informed-consent of the patient. The strain was thoroughly identified and stored. Other clinical isolated MDR Gram-negative strains (Table 2, 3) were obtained from clinical patients in Renmin Hospital of Three Gorges University in Hubei Province, PRC, with all approvals and informed consents.

Antibiotics and Chemicals

All experiments were performed in Luria-Bertani (LB) medium (EMD millipore). Unless otherwise specified, the following concentrations were used for the antibacterial experiments with *E. coli* strains and clinical pathogens: 0, 1, 2, 4, 5, 20, 40, 80 µM 2-Phenyl-1, 2-benzisoselenazol-3 (2H)-one (ebselen) (Daiichi), and 0, 0.625, 1.25, 2.5, 5, 10, 20, 40, 80 µM silver nitrate (Sigma-Aldrich). 4-acetamido-4'-maleimidylstilbene-2,2'-disulfonic acid (AMS) (Invitrogen), protease inhibitor cocktails (Roche), DC™ protein assay (Bio-RAD), propidium iodide (PI) (BD Biosciences), *E. coli* DHB4 TrxR, sheep anti-*E. coli* Trx1 antibody and Rabbit anti-*E. coli* Trx2 antibody were from IMCO Corp. (Stockholm, Sweden), Goat anti-Rabbit IgG-HRP (Santa Cruz, lot #H1015), Rabbit anti-Goat IgG-HRP (Southern Biotech, lot #12011-PG56), IgG2a mouse monoclonal antibody for glutathione-protein complexes (VIROGEN, lot #101-A, clone number D8), 4-12% bolt Bis-Tris gel (VWR), all the other reagents were from Sigma-Aldrich.

Synergistic Effect of Silver with Ebselen in Combination on *E. coli* Growth

*E. coli* DHB4 cells overnight cultures were diluted 1:1000 times in Luria-Bertani (LB) medium and treated with serial concentrations of AgNO3 and/or ebselen for 16 h. The cell viability was determined by measuring the absorbance at 600 nm. The culture treated with 0.8% (v/v) DMSO was used as a control.

Toxicity Analysis of Silver with Ebselen in Combination Against Mammalian Cells

HeLa cells were purchased from ATCC, and through *mycoplasma* detection and human cell line authentication by STR analysis (ATCC, U.S.A). HeLa cells cultured in DMEM medium supplemented with 10% FCS, 100 units/ml penicillin, and 100 µg/ml streptomycin at 37° C. in a 5% $CO_2$ incubator. The cells were seeded in 96 micro-well plates and grown till 70-80% confluency. The cells were treated with serial combinations of ebselen and AgNO3 for 24 h. The cell toxicity was detected by MTT assay.

Antibacterial Effect of Silver with Ebselen in Synergistic Combination on the Growth of Clinical Isolated MDR Gram-Negative Strains Ten clinical isolated MDR Gram-negative (GSH-positive) strains were grown until an $OD_{600\ nm}$ of 0.4 and were diluted 1:100 into 100 µl of LB medium in 96 micro-well plates. Serial dilutions of 100 µl ebselen and AgNO3 were added to the individual wells. The minimum inhibitory concentration (MIC) was determined after 16 h culture at 37° C. The culture treated with 0.8% (v/v) DMSO was used as a control.

Detection of Bactericidal Effect of Silver with Ebselen in Combination on *E. coli* Strains

*E. coli* DHB4 cells were grown in 15 ml tubes until an $OD_{600\ nm}$ of 0.4, and treated with 5 µM AgNO3 and serial concentration of ebselen (0, 20, 40, 80 µM) in combination. The survival of untreated *E. coli* was compared with the antibiotic-treated cells by measuring $OD_{600\ nm}$ and counting the colonies. For colony formation assay, cells were harvested at 10 min, 1 h, 2 h, and 4 h by centrifugation at 6,000 rpm for 5 min and thoroughly washed 3 times with PBS. The cells were serially diluted in PBS, and 100 µl cultures were plated on LB plates. The colonies were counted after overnight incubation, and CFU/ml was calculated using the following formula: [(colonies)*(dilution factor)]/(amount plated).

Further, cells cultured and washed as above were harvested at 10 min by centrifugation at 6,000 rpm for 5 min and thoroughly washed 3 times with PBS. Nuclei were stained with 5 µg/ml propidium iodide (PI) for 20 min in the absence of a cell permeate and analyzed by flow cytometry (CyAn adp, Beckman coulter).

Measurement of Trx/TrxR Activity and GSH Amount in Silver and Ebselen Treated *E. coli* Cell Lysates

*E. coli* DHB4 cells were grown till the absorbance at $OD_{600\ nm}$ of 0.4 in LB medium, and the bacterial cells were treated with different dilutions of ebselen and AgNO3 for 10 min. Cells were harvested by centrifugation at 6,000 rpm for 5 min and thoroughly washed 3 times with PBS, then cells were re-suspended in lysis buffer (25 mM Tris·HCl, pH 7.5, 100 mM NaCl, 2.5 mM EDTA, 2.5 mM EGTA, 20 mM NaF, 1 mM $Na_3VO_4$, 20 mM sodium ß-glycerophosphate, 10 mM sodium pyrophosphate, 0.5% Triton X-100) containing protease inhibitor cocktail and lysed by sonication. The cell lysates were obtained by centrifugation at 13,000 rpm for 20 min and the protein concentration was measured by Lowry protein assay (Bio-Rad DC™).

*E. coli* DHB4 TrxR activity in cell extracts was measured by a DTNB reduction activity assay. The experiments were performed with 96 micro-well plates in the solution containing 50 mM Tris·HCl (pH 7.5), 200 µM NADPH, 1 mM EDTA, 1 mM DTNB, in the presence of 5 µM *E. coli* Trx. The absorbance at 412 nm was measured for 5 min with a VERSA micro-well plate reader and the slope of initial 2 min was used to represent TrxR activity. The Trx activity was detected by this method coupled with 100 nM *E. coli* TrxR instead of 5 µM *E. coli* Trx in the reaction mixture.

To measure GSH levels, 25 µg of the cell lysates was added in the solution containing 50 nM GR, 50 mM Tris·HCl (pH 7.5), 200 µM NADPH, 1 mM EDTA, 1 mM DTNB. The absorbance at 412 nm was measured for 5 min.

Trx Redox State in *E. coli* Treated with Silver and Ebselen in Combination

*E. coli* DHB4 cells were grown till the absorbance at $OD_{600\ nm}$ of 0.4 in LB medium, and the bacterial cells were treated with different dilutions of ebselen and AgNO3 for 10 min. Western blotting was performed to detect the Trx1 and Trx2 redox state of the ebselen and AgNO3 treated *E. coli* cells. The cells were harvested by centrifugation at 6,000 rpm for 5 min and thoroughly washed 3 times with PBS, and precipitated the protein with 5% TCA in 1.0 ml. The precipitates were washed with 1 ml pre-ice-cold acetone for 3 times, and dissolved in 50 mM Tris·HCl (pH 8.5) with 0.5% SDS containing 15 mM AMS at 37° C. for 2 h. Proteins were obtained by centrifugation at 13,000 rpm for 20 min to remove the pellets, and the protein concentration was measured by Lowry protein assay (Bio-Rad DC™). Redox state of Trx1 and Trx2 was detected with sheep anti-*E. coli* Trx1 antibody and (Rabbit anti-*E. coli* Trx2 antibody) at 1:1000 dilution, followed by the detection of Chemiluminescence Reagent Plus.

Proteins S-Glutathionylation in *E. coli* Treated with Silver and Ebselen in Combination Total proteins S-glutathionylation of the ebselen with AgNO3 in combination treated *E. coli* cells were detected by Western blotting. Cells were cultured and washed as described above, and re-suspended in lysis buffer (25 mM Tris·HCl, pH 7.5, 100 mM NaCl, 2.5 mM EDTA, 2.5 mM EGTA, 20 mM NaF, 1 mM $Na_3VO_4$, 20 mM sodium ß-glycerophosphate, 10 mM sodium pyrophosphate, 0.5% Triton X-100, protease inhibitor cocktail) containing 30 mM IAM. After lysed by sonication, the cell lysates were obtained by centrifugation at 13,000 rpm for 20 min. Protein concentration was measured by Lowry protein assay (Bio-Rad DC™). Samples were incubated with SDS-loading buffer at 90° C. for 10 min, and then separated on the 4-12% bolt Bis-Tris gel with MES running buffer (150V, 40 min). Western blotting assay was performed with IgG2a mouse monoclonal antibody (VIROGEN, 101-A/D8) for glutathione-protein complexes.

Synergistic Effect of Silver and Ebselen on the Growth of *E. coli* DHB4 Redox Phenotypes Eleven *E. coli* DHB4 redox phenotypes were grown until an $OD_{600\ nm}$ of 0.4, and were diluted 1:100 into 100 µl of LB medium in 96 micro-well plates. Serial dilutions of ebselen and AgNO3 were added to the individual wells. The minimum inhibitory concentration (MIC) was determined after 24 h culture at 37° C. The culture treated with 0.8% (v/v) DMSO was used as a control.

Inhibition of Recombinant Bacterial Trx/TrxR by Silver

Inhibition of recombinant bacterial TrxR by Silver was performed by using *E. coli* enzyme. The experiments were performed with 96 micro-well plates in the solution containing 50 mM Tris·HCl (pH 7.5), 200 µM NADPH, 1 mM EDTA, 1 mM DTNB, in the presence of 5 µM *E. coli* Trx. The absorbance at 412 nm was measured for 5 min with a VERSA micro-well plate reader and the slope of initial 2 min was used to represent TrxR activity. The Trx activity was detected by this method, coupled with the use of 100 nM *E. coli* TrxR instead of 5 µM *E. coli* Trx in the reaction mixture.

Analysis of Fluorescent Spectra

Fluorescent Spectra of reduced *E. coli* Trx with Silver were recorded at 10 µM in a PerkinElmer Enspire multilabel recorder using an excitation at 280 nm.

Measurement of ROS Production

The *E. coli* DHB4 cells were grown till the absorbance at $OD_{600\ nm}$ of 0.4 in LB medium, and the bacterial cells were treated with different combinations of ebselen and AgNO3 for 10 min. To analyze the amount of ROS production in the bacteria, cells were harvested by centrifugation at 6,000 rpm for 5 min and thoroughly washed 3 times with PBS, and stained with 5 µM $H_2$DCF-DA for 20 min. After the incubation, cells were spin down and re-suspended in PBS, and the ROS production was quantified by flow cytometry (CyAn adp, Beckman coulter).

$H_2O_2$ Production

The *E. coli* DHB4 cells were grown till the absorbance at $OD_{600\ nm}$ of 0.4 in LB medium, and the bacterial cells were treated with 20 µM ebselen and 5 µM AgNO3 for 10 min. Cells were harvested by centrifugation at 6,000 rpm for 5 min and thoroughly washed 3 times with PBS, and sonicated for 10 s. In the presence of 50 µM Amplex® Red reagent, 0.1 U/mL HRP in 50 mM sodium phosphate buffer, pH 7.4, 50 µl samples were incubated for 30 minutes at room temperature protected from light, and detected with absorbance at 560 nm (Molecular Probes, Eugene, Oreg.).

Effect of Ebselen on *E. coli* Growth

*E. coli* DHB4 cells were grown until an $OD_{600\ nm}$ of 0.4, and treated with serial dilutions of ebselen (0, 2, 4, 8 µM) for 16 h. The cell viability was determined by measuring the absorbance at 600 nm. The culture treated with 0.8% (v/v) DMSO was used as a control.

Direct Survival Rate Assay

The direct survival rate assay was performed to assess the survival capacity of ebselen and AgNO3 treated *E. coli* DHB4 strain in healthy mice blood. The phosphate-buffered saline (PBS, pH 7.6) treated cells were used as the positive control, and the experiment was performed in duplicate. Briefly, blood was extracted from 3 mice and collected in heparinized tubes. Approximately 100 *E. coli* DHB4 cells were harvested during the logarithmic phase, washed with sterile PBS, and added to 100 µl blood. After incubation at 37° C. for 6 h, duplicate 100 µl aliquots from each blood sample were spread onto LB agar, and the surviving colonies were enumerated after overnight incubation. The results showed that ebselen and AgNO3 could help innate immunity to clear *E. coli*.

Inhibition of Recombinant Mammalian TrxR by Silver

The experiments were performed with 96 micro-well plates in the solution containing 50 mM Tris·HCl (pH 7.5), 250 μM NADPH, 1 mM EDTA, 1 mM DTNB, in the presence of 10 nM *E. coli* TrxR. The absorbance at 412 nm was measured for 5 min with a VERSA micro-well plate reader and the slope of initial 2 min was used to represent TrxR activity.

Statistical Analysis

Mean, Standard Deviation (SD) and t-test (two tails, unpaired) significances were calculated in GrapPad Prism Software. *: $p<0.05$, : $p<0.01$, *: $p<0.001$.

Example 2. In Vivo Experiments 2.1 Results

The bactericidal effect of $Ag^+$ with ebselen in combination was also observed in LB medium containing heparinized mice blood. To investigate whether the bactericidal activity of $Ag^+$ with ebselen in combination is also efficient in vivo, mice were infected i.p. with $6.0\times10^7$ or $1.7\times10^6$ MDR *E. coli* ZY-1 (Table 7), modeling an acute and a mild peritonitis, respectively. The LD50 of *E. coli* ZY-1 administered i.p. was $1.3\times10^7$ CFU/ml. One hour (acute model) or 24 h (mild model) after infection, mice were treated i.p. with ebselen, $Ag^+$, or the drugs in combination, or remained untreated. The combination of $Ag^+$ and ebselen led to a significant reduction of bacterial load compared with the control in the mild peritonitis model. Mice treated with ebselen alone or left untreated showed similar levels of bacteria load after 36 h of infection with $6.0\times10^7$ *E. coli*, whereas treatment with $Ag^+$ with ebselen in combination achieved a 100-fold reduction compared with control ($p=0.0055<0.01$)(FIG. 6A). Additionally, 80% of mice treated with $Ag^+$ with ebselen in combination survived in the acute peritonitis mice model, compared with 30% in control group (FIG. 6B). These findings demonstrated the effective antibacterial effect of $Ag^+$ and ebselen against MDR Gram-negative pathogen in vivo.

$Ag^+$ or ebselen alone has been proven to be safe in previous studies. To test the toxicity of the combination, mice were divided 5 per group, which were treated with 6 mg AgNO3/kg body weight in combination with serial concentrations of ebselen (10, 15, 20, and 25 mg ebselen/kg body weight). Mice were observed for 7 days and remained viable with no mortality. The effect of 25 mg ebselen/kg and 6 mg AgNO$_3$/kg body weight in combination were evaluated on mice by measuring key metabolite and enzyme concentrations using a Blood Chemistry Analyzer after treatment for 6, 24 and 48 hours. The density of lymphocytes and monocytes and some enzymes, such as alanine transaminase in mice treated with $Ag^+$ and ebselen in combination were reduced at the initial point (6 h); however, their values gain back into normal at 24 h post-treatment (Table 8), indicating that there is a stress response upon the initial treatment. These results demonstrated that $Ag^+$ and ebselen were not toxic for mice at the conditions tested.

2.2 Materials and Methods

Mild Peritonitis Mice Model Assay

Approval from the Medical Animal Care & Welfare Committee of China Three Gorges University was obtained prior to using the animals for research. Healthy 6-week-old Kunming male mice (body weight, 18±2 g) were purchased from Laboratory Animal Center of China, Three Gorges University. All mice were kept in individually ventilated cages (five mice per cage) under a constant dark (12 h)-light (12 h) cycle in a conventional SPF animal house and were free access to food and water. Five mice were sampled randomly to examine bacterial recovery from the brain, liver, spleen and kidney to rule out *E. coli* infection before experimental manipulation, and no bacteria were detected.

The experimentation was performed in random block design and single-blind trial. The sample size was calculated by power analysis, and estimated as: corrected sample size=sample size/(1−[% attrition/100]). Forty-eight mice were divided into 4 groups, 12 mice/group. Inoculation was performed by intraperitoneal injection of 100 μl $1.7\times10^6$ *E. coli* ZY-1 cells using a 26-gauge syringe. The inoculum was delivered in suspension with 8% (w/v) mucin in sterile saline. 24 h after introduction of the inoculum, 12 mice per group received antibacterial treatments. 0, 12, 24, and 36 h post-infection, peritoneal washes were performed by injecting 1.0 ml of sterile saline in the intraperitoneal cavity followed by a massage of the abdomen (100 times/mouse). Subsequently, the abdomen was opened and 200 μl of peritoneal fluid (PF) was recovered from the peritoneum for analysis of *E. coli* CFU/ml, and CFU/ml was enumerated. For the CFU/ml measurement, the peritoneal fluid was serially diluted in PBS (pH 7.6). Experiments are performed triplicate.

Acute Peritonitis Mice Model Assay

The experimentation was designed in random block design and single-blind trial, and 40 mice were divided into 4 groups, 10 mice/group. Inoculation was performed by intraperitoneal injection of 100 μl of $6.0\times10^6$ CFU/ml *E. coli* ZY-1 inoculums using a 26-gauge syringe. The inoculum was delivered in suspension with 8% (w/v) mucin in sterile saline. 1 h after introduction of the inoculum, 10 mice per group received antibacterial treatments, and the mice were observed for 7 days to evaluate overall survival. Experiments are performed duplicate.

In Vivo Toxicity Analysis of Silver with Ebselen in Combination

Five mice per group were treated with 6 mg AgNO3/kg body weight and serial concentration of ebselen (10, 15, 20, 25 mg AgNO$_3$/kg body weight) intraperitoneally. Mice were observed for 7 days, and the overall survival was calculated.

Blood Samples Analysis

Three mice per group were treated with parenterally administered PBS, 25 mg ebselen/kg body weight in combination with 6 mg AgNO$_3$/kg body weight, and vehicle. The animals were observed for two days and retro-orbital blood sample collection was performed 6, 24 and 48 h after treatment. Blood was collected in heparinized whole blood test tubes and further analyzed by Blood Chemistry Analyzer (SYSMEX XE5000).

Statistical Analysis

Mean, Standard Deviation (SD) and t-test (two tails, unpaired) significances were calculated in GrapPad Prism Software. *: $p<0.05$, : $p<0.01$, *: $p<0.001$.

Example 3. Comparison with Conventional Antibiotics 3.1. Results Against *E. coli*

Combination of Silver with Certain Antibiotics Exhibited Synergistic Toxicity Against *E. coli*

Figure 7:
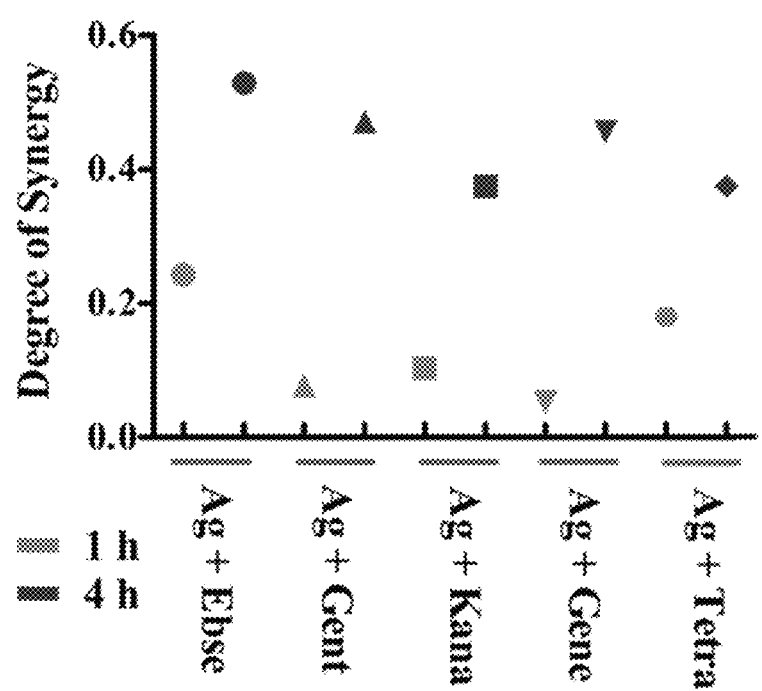
FIG. 7 is a chart showing that the Bliss model for synergy confirms a synergistic effect, between Ag+ and 4 antibiotics, against a model Gram-negative bacteria, E. coli. The degree of synergy was quantified, using the Bliss Model for Synergy, after 1 and 4 h of treatment with 5 µM $AgNO_3$ in combination with the following antibiotics: 80 µM gentamicin, 80 µM kanamycin, 80 µM geneticin, 80 µM tetracycline, and 80 µM Ebselen was used as positive control.

The antibacterial effects of silver nitrate (AgNO$_3$) and nine antibiotics representing five different functional categories (beta-lactams, aminoglycosides, synthesis, tetracycline, and macrolides) on the growth of a model Gram-negative bacterium, E. coli, was investigated in the 96 wells microplates. E. coli DHB4 overnight cultures were diluted 1:1000 times in Luria Bertani (LB) medium, and treated with serial dilutions of ionic silver ($Ag^+$) as a nitrate salt and 9 antibiotics in combinations, separately, for 24 h. Ebselen was used as the positive control, which acted synergistically with silver against Gram-negative bacteria. The results here showed that 4 (gentamicin, kanamycin, geneticin, tetracycline) out of 9 antibiotics had synergistic activity on E. coli DHB4 growth (Table 9). Further, the Bliss model was used to determine the nature of the therapeutic effects exhibited by the silver and antibiotics in combinations. The degree of synergy was quantified at 1 and 4 h between $Ag^+$ and 4 antibiotics (gentamicin, kanamycin, geneticin, and tetracycline) in combinations, and the results showed that $Ag^+$ and 4 antibiotics indeed had synergistic combinations against E. coli (FIG. 7). All the results pointed out that silver could enhance the antibacterial effects of certain antibiotics against Gram-negative bacteria.

Figure 8A:
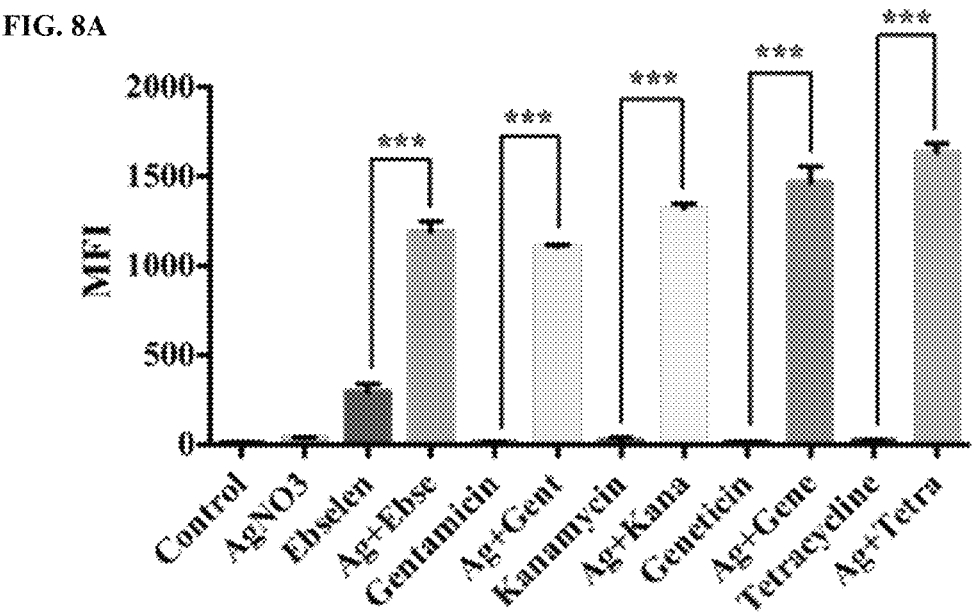
FIGS. 8A and 8B illustrate that ROS was a determining factor for synergistic bactericidal effects of silver and antibiotics in combinations. E. coli DHB4 grown to $OD_{600\,nm}$ of 0.4 were treated with 80 µM antibiotics and 5 µM $AgNO_3$ in combinations, and silver and ebselen in combination was used as a positive control.
Figure 8B:
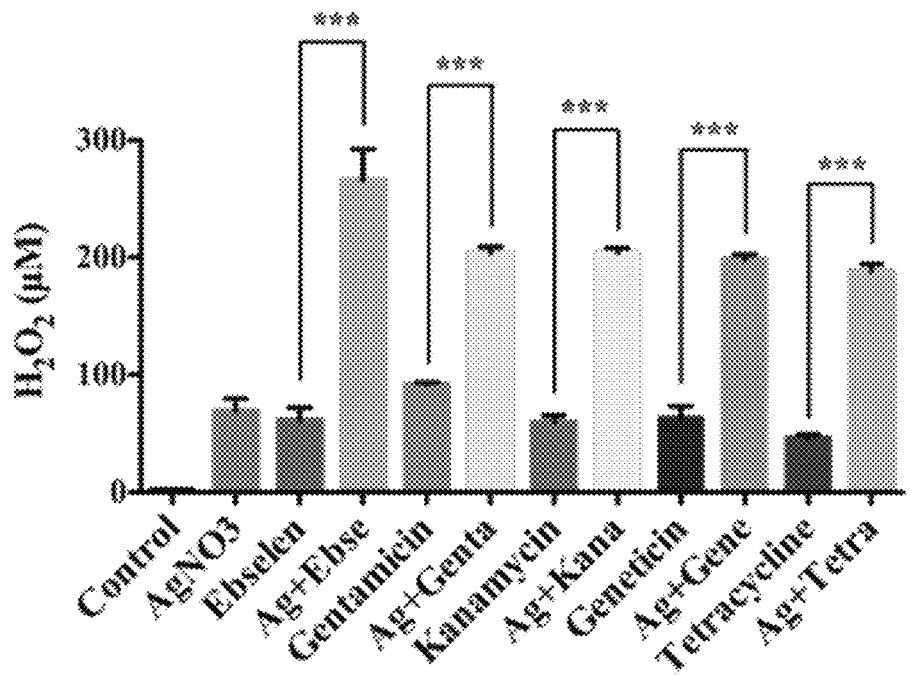

ROS was a Lethal Factor for Synergistic Bactericidal Effects of $Ag^+$ and Antibiotics $Ag^+$ and ebselen in combination could induce a high level of ROS, and the effects of $Ag^+$ and antibiotics in combinations need further studies. We, therefore, determined ROS levels in $Ag^+$ and 4 antibiotics in combinations treated cells, and $Ag^+$ and ebselen in combination was used as a positive control. The results showed that treatment with 5 μM $Ag^+$ and 80 μM antibiotics in combinations resulted in increased levels of ROS ($p<0.0001$) (FIG. 8A). Further, the enhancement of $H_2O_2$ levels caused by the treatment with 5 μM $Ag^+$ and 80 μM antibiotics in combinations were also verified by Amplex Red method ($p<0.0001$) (FIG. 8B). The results demonstrated that ROS was one of the determining factors for synergistic bactericidal effects of $Ag^+$ and antibiotics in combinations against E. coli.

$Ag^+$ and Antibiotics could Disrupt Bacterial Trx System

Figure 9A:
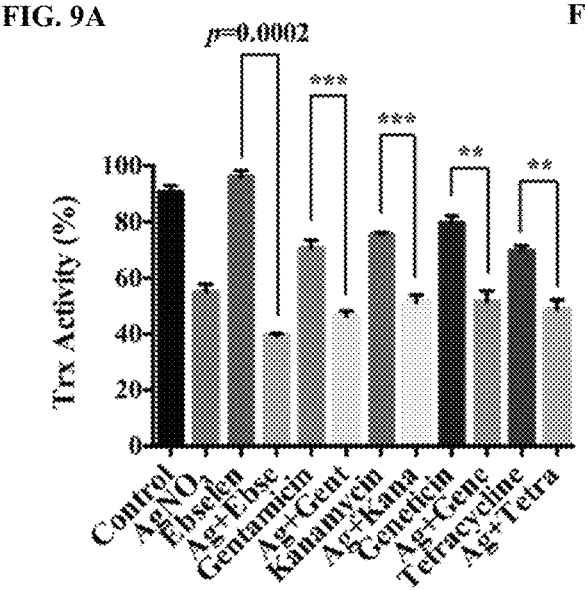
FIGS. 9A to 9C illustrate that antibiotics alone could not directly disrupt bacterial Trx system. E. coli DHB4 grown to $OD_{600\,nm}$ of 0.4 were treated with antibiotics and AgNO3 in combinations for 10 min, and ebselen and $AgNO_3$ in combination was used as a positive control.
Figure 9B:
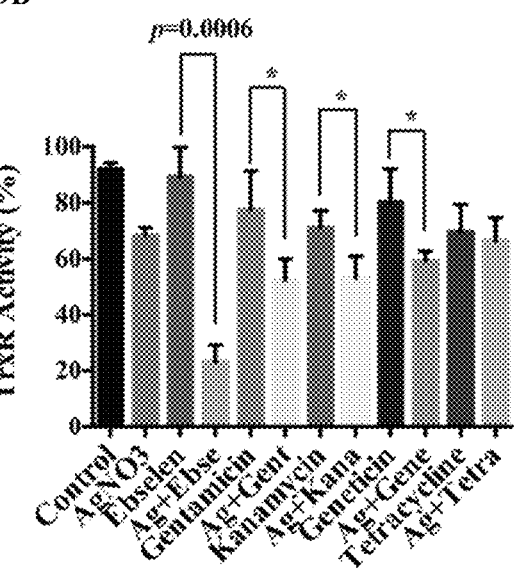

One major function of thiol-dependent antioxidant systems is to scavenge ROS to keep cellular redox balance and protect against oxidative stress. The inhibition of the Trx system and depletion of GSH may responsible for the elevation of ROS. $Ag^+$ and ebselen in combination has been proven to target both bacterial Trx and GSH systems, while the effects of $Ag^+$ and antibiotics in combinations need further studies. E. coli DHB4 grown to $OD_{600\ nm}$ of 0.4 were treated with 5 μM $Ag^+$ and 80 μM antibiotics in combinations, and $Ag^+$ and ebselen in combination was used as a positive control. Results here showed that after 10 min treatment, the Trx activities in cell extracts treated by $Ag^+$ and antibiotics in combinations were dramatically inhibited compared with antibiotics or control group (FIG. 9A, $p<0.001$); meanwhile, the TrxR activities in cell extracts treated by $Ag^+$ and antibiotics in combinations were also statistically lowered when compare with antibiotics or control group (FIG. 9B, $p<0.05$). The same results were obtained when the treatment time was prolonged to 60 min. These results suggested that silver and antibiotics in combinations have direct influences on Trx1.

Figure 9C:
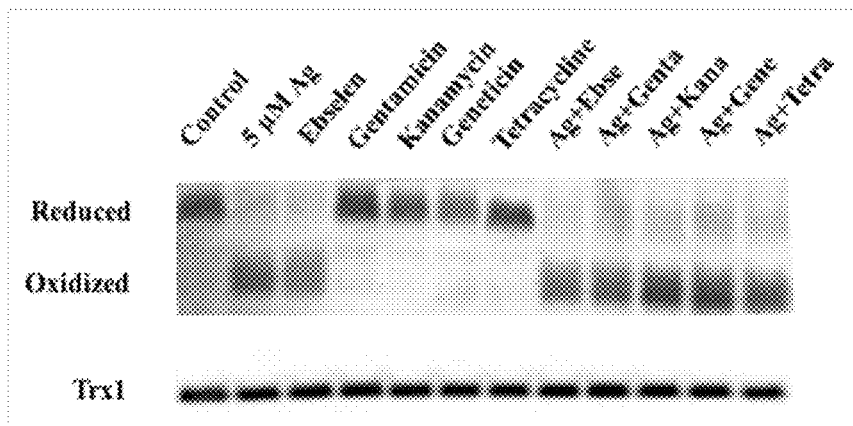

Consistent with this observation, redox state of Trx1 measured by Redox Western Blot was also affected by $Ag^+$ and antibiotics in combinations after 60 min treatment. Trx1 was in reduced form in untreated bacteria, and became oxidized upon the treatment by $Ag^+$ and antibiotics in combinations (FIG. 9C). In contrast, only 10 min treatment by $Ag^+$ and antibiotics in combinations could not cause Trx1 oxidization. At the same time, the total protein levels of Trx1 were not affected following a 10 min or 60 min treatment by $Ag^+$ and antibiotics in combinations. These results showed that when targeting Trx system, silver and antibiotics in combinations was not acting as fast as silver and ebselen do. All the results showed that silver and antibiotics in combinations had direct influences on the Trx system.

Figure 10A:
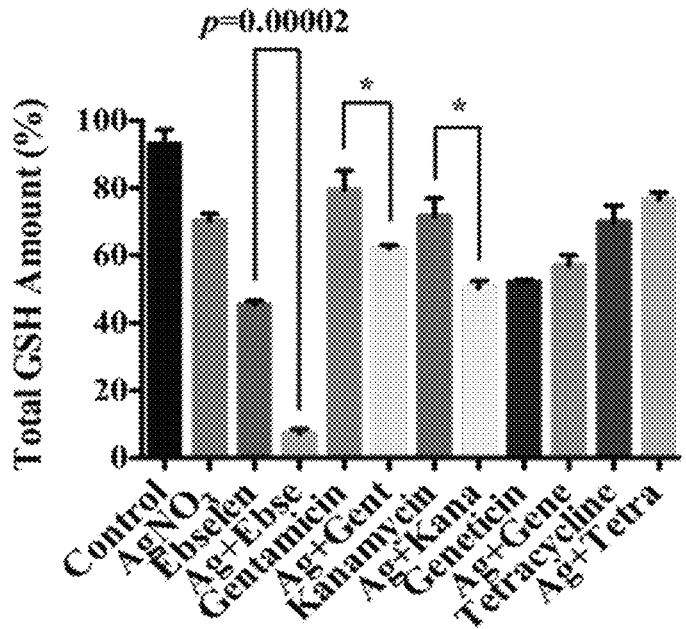
FIGS. 10A and 10B illustrate that silver and conventional antibiotics in combinations could not directly disrupt the bacterial GSH system for 10 minutes. E. coli DHB4 grown to $OD_{600\,nm}$ of 0.4 were treated with antibiotics and $AgNO_3$ in combinations for 10 min, and ebselen and $AgNO_3$ in combination was used as a positive control.
Figure 10B:
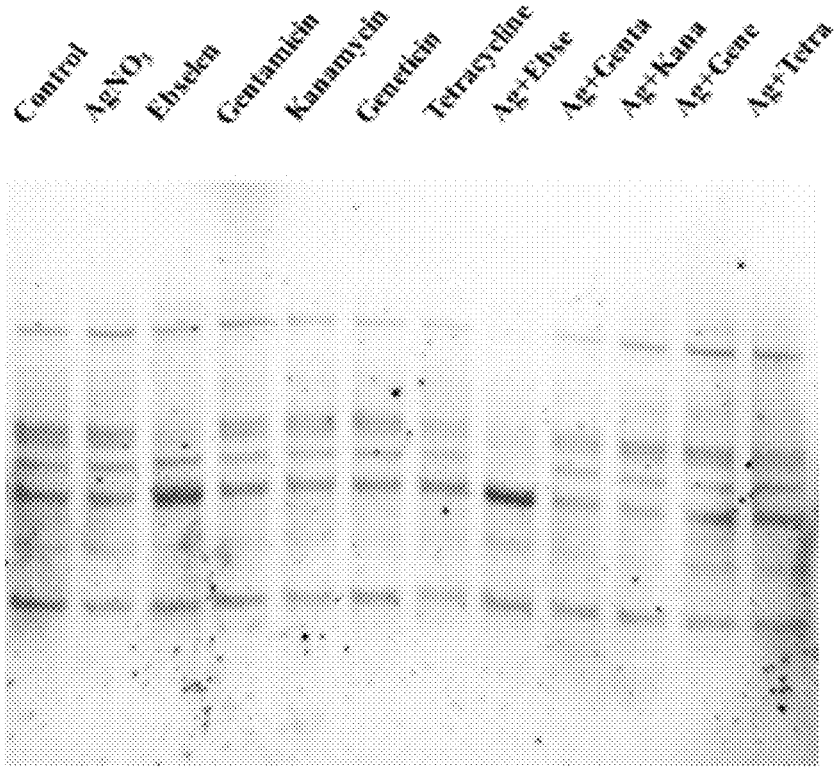
Figure 11A:
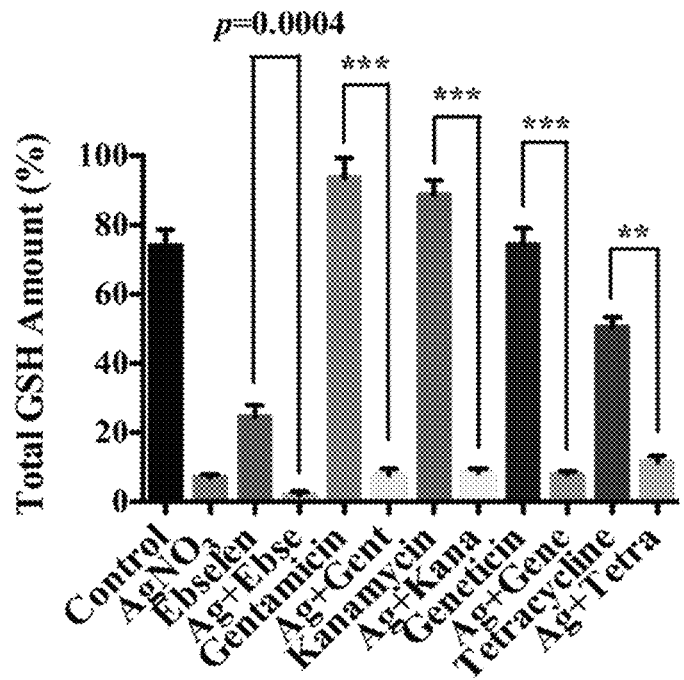
FIGS. 11A and 11B illustrate that silver and conventional antibiotics in combinations could not directly disrupt the bacterial GSH system for 60 minutes. E. coli DHB4 grown to $OD_{600\,nm}$ of 0.4 were treated with antibiotics and $AgNO_3$ in combinations for 60 min, and ebselen and $AgNO_3$ in combination was used as a positive control.
Figure 11B:
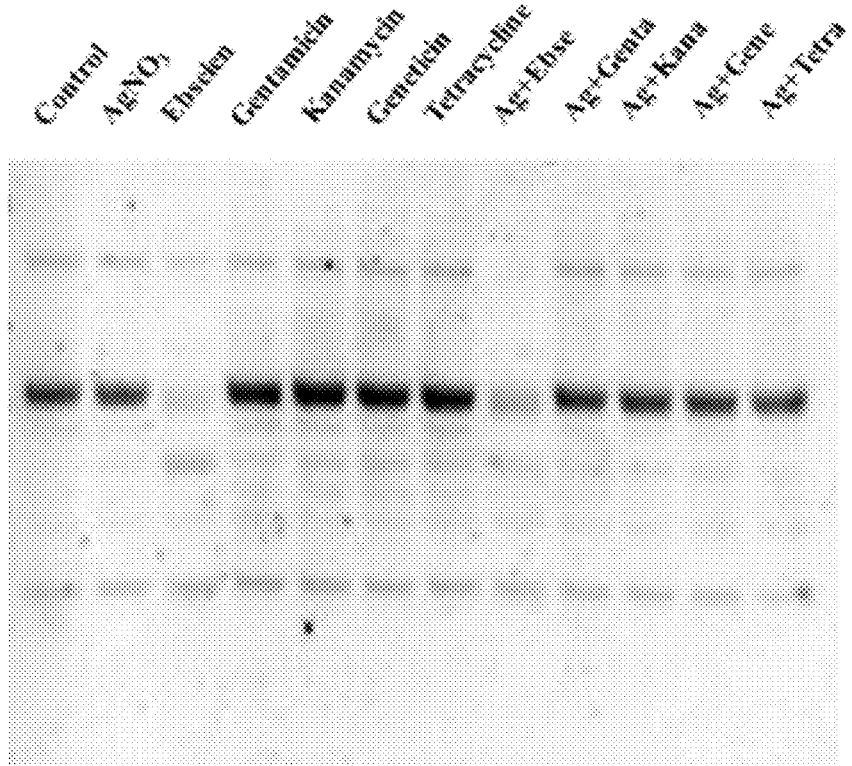

$Ag^+$ and Conventional Antibiotics could not Directly Disrupt Bacterial GSH System 5 μM $Ag^+$ and 80 μM ebselen in combination has also been proven to deplete the GSH after 10 min treatment. In that study, only 5 μM $Ag^+$ and 80 μM gentamicin or kanamycin in combinations could slightly deplete the total GSH amount in cell extracts when compared with antibiotics themselves ($p<0.05$) (FIG. 10A), meanwhile other combinations showed no differences (FIG. 10B) ($p>0.05$). The same results were obtained when the treatment time was prolonged to 60 min (FIGS. 11A and 11B). Further, the protein S-glutathionylation was decreased in $Ag^+$ and ebselen in combination treated bacteria, but not in those incubated with 5 μM $Ag^+$ and antibiotics in combination for 10 min (FIG. 10B) or 60 min treatments (FIG. 11B).

All the results above suggested that silver and conventional antibiotics had no direct effect on bacterial GSH system when acting against Gram-negative bacteria. 4 out of 9 conventional antibiotics acted synergistically with silver against E. coli, a model Gram-negative bacterium (Table 9), which might occur through a direct targeting of Trx and TrxR and inducing ROS production (FIGS. 8A-8B, and 9A-9C), but not the GSH content (FIGS. 10A-10B and 11A-11B). The synergistic effect came along with the production of reactive oxygen species.

3.2 Results Against Five MDR Gram-Negative Pathogens

The four conventional antibiotics identified in 3.1 were further studied in comparison with ebselen in combination with silver. Using clinically isolated strains of K. pneumonia, A. baumannii, P. aeruginosa, E. cloacae and E. coli, only ebselen at 4 μM, out of five antibiotics lowered the MIC of silver dramatically.

Clinically Isolated Five Most Difficult-to-Treat MDR Gram-Negative Pathogens were Highly Sensitive to Only $Ag^+$ and Ebselen in Combinations There are five clinically most difficult-to-treat MDR Gram-negative pathogen species: Klebsiella pneumonia, Acinetobacter baumannii, Pseudomonas aeruginosa, Enterobacter cloacae and Escherichia coli. One strain from each species was isolated, and overnight cultures were diluted 1:1000 times in LB medium, and treated with serial concentrations of $Ag^+$ and antibiotics in combinations for 24 h (Table 10). The results showed that $Ag^+$ and antibiotics in combination exhibited weak antibacterial effects on these MDR Gram-negative bacteria, meanwhile, $Ag^+$ and ebselen in combination might be the only effective antibiotic against a range of resistant bacteria. The results might be explained by the fact that silver and antibiotics in combination could only directly disrupt the Trx system but not both the Trx and GSH systems.

Although silver and 4 different antibiotics in combinations could directly inhibit Trx and TrxR, yet the direct effect targeting GSH system is not universal. The presence of the GSH-Grx system in E. coli may be regarded as a backup for the Trx system. GSH/Grxs in E. coli participate in the antioxidant process by deglutathionylation and transfer electrons to ribonucleotide reductase. Silver and four conventional antibiotics in combinations showed no effects on GSH amount, and the S-glutathionylated proteins are not much different from that of in control group (FIG. 10). Thus, this might explain the anti-MDR-Gram-negative bacteria activities of silver and antibiotics in combinations were much weaker than silver and ebselen in combination.

3.3 Materials and Methods

Bacterial Strains

All in vitro experiments were performed with *Escherichia coli* (*E. coli*) DHB4, and clinically isolated multidrug-resistance (MDR) Gram-negative strains shown below. Clinical isolated MDR Gram-negative strains were obtained from clinical patients in Renmin Hospital of Three Gorges University in Hubei Province, PRC, with all approvals and informed consents.

| Clinically isolated multidrug-resistant Gram-negative strains used in this work | |
|---|---|
| Strain | Description |
| KP-2 | *K. pneumonia*subsp. *pneumonia* 0322# |
| AB-1 | *Acinetobacter baumannii* (*A. baumannii*) H# |
| PA-1 | *Pseudomonas aeruginosa* (*P. aeruginose*) 1298# |
| ECL-2 | *E. cloacae* 2301# |
| ECO-1 | *Escherichia coli* (*E. coli*) 1139# |

| Drug sensitivity of clinical isolated multidrug-resistant Gram-negative bacteria | | | | | |
|---|---|---|---|---|---|
| Antibiotic | KP-2 | AB-1 | PA-1 | ECL-2 | ECO-1 |
| Amikacin | S | R | S | S | S |
| Ampicillin | R | R | R/S | / | S |
| Aztreonam | R | R | R | R | R |
| Cefazolin | R | R | R | / | R |
| Cefepime | R | R | R | R | R |
| Cefotaxime | R | R | R | R | R |
| Ceftazidime | R | R | R | R | R/S |
| Chloramphenicol | R | R | / | R | S |
| Ciprofloxacin | R | R | R | R | R |
| Gentamicin | R | R | S | R | S |
| Imipenem | S | R | S | R | S |
| Levofloxacin | R | R | R | R | R |
| Meropenem | S | R | R | R | S |
| Piperacillin | R | R | R/S | R | R |
| Polymyxin | / | S | S | S | / |
| Sulbactam | R | R | / | / | R/S |
| Sulfanilamide | R | / | R | R | R |
| Tazobactam | R | R | R/S | R | S |
| Tetracycline | R | R | R | R | R |

*R: resistant; S: sensitive.

Antibiotics and Chemicals

All experiments were performed in Luria Bertani (LB) medium (EMD millipore), 2-Phenyl-1, 2-benzisoselenazol-3(2H)-one (ebselen) (Daiichi), 9 antibiotics: ampicillin, carbenicillin, gentamicin, streptomycin, geneticin, kanamycin, chloramphenicol, tetracycline, erythromycin, silver nitrate (Sigma-Aldrich), Methoxypolyethylene glycol maleimide (MeO-PEG-Mal) (Sigma-Aldrich), Iodoacetamide (IAM) (Sigma-Aldrich), protease inhibitor cocktails (Roche), N-acelytcysteine (NAC) (Sigma-Aldrich), DC™ protein assay (Bio-RAD), *E. coli* DHB4 TrxR, sheep anti-*E. coli* Trx1 antibody was from IMCO Corp. (Stockholm, Sweden; http://www.imcocorp.se), Rabbit anti-sheep IgG-HRP (Santa cruz), IgG2a mouse monoclonal antibody for glutathione-protein complexes (VIROGEN), 4-12% bolt Bis-Tris gel (VWR), all the other reagents were from Sigma-Aldrich.

| Antibiotics used in the study with their dosages and primary targets | | | |
|---|---|---|---|
| Antibiotic | Abbreviation | Dose (µM) used | Primary target |
| Ampicillin | Amp | 0/1/2/4 | Cell wall formation |
| Carbenicillin | Car | 0/1/2/4 | Cell wall formation |
| Chloramphenicol | Chl | 0/1/2/4 | Protein synthesis, 50S ribosomal subunit |
| Erythromycin | Ery | 0/1/2/4 | Protein synthesis, 50S ribosomal subunit |
| Gentamicin | Gent | 0/1/2/4/80 | Protein synthesis, 30S ribosomal subunit |
| Geneticin | Gene | 0/1/2/4/80 | Protein synthesis, 30S ribosomal subunit |
| Kanamycin | Kan | 0/1/2/4/80 | Protein synthesis, 30S ribosomal subunit |
| Streptomycin | Str | 0/1/2/4 | Protein synthesis, 30S ribosomal subunit |
| Tetracycline | Tet | 0/1/2/4/80 | Protein synthesis, 30S ribosomal subunit |

Synergistic Antibacterial Effect of Silver and Antibiotics in Combinations on the Growth of *E. coli* DHB4

*E. coli* DHB4 from frozen stock were grown overnight at 37° C., 400 rpm. The overnight culture was diluted 1:100 with 5 ml of LB medium in 15 ml tubes and incubated at 37° C. at 400 rpm. Cells were grown until an $OD_{600\ nm}$ of 0.4 and were used for antibiotic treatment. Briefly, cells were diluted 1:1,000 into 100 µl of LB medium in 96 micro-well plates. Serial dilutions of antibiotics 100 µl (0, 1, 2, 4 µM) and silver nitrate ($AgNO_3$, 0, 1.25, 2.5, 5, 10, 20, 40, 80 µM) were added to the individual wells. The minimum inhibition concentration (MIC) was determined as the lowest concentration of drugs that inhibited 90% of growth compared to the untreated cells after 24 h culture at 37° C. The cultures treated with the same serial dilutions of 100 µl ebselen and silver nitrate were used as the positive control.

Quantifying Synergy of Ebselen and Silver Using the Bliss Model

Drug synergism was determined using the Bliss Independence Model, which calculates a degree of synergy using the following formula: $S=(f_{X0}/f_{00})(f_{0Y}/f_{00})-(f_{XY}/f_{00})$, where $f_{XY}$ refers to the wild-type growth rate in the presence of the combined drugs at a concentration X, for one of the drugs, and Y for the other; $f_{X0}$ and $f_{0Y}$ refer to the wild-type growth rates in the presence of the individual drugs at a concentration of X and Y, respectively; $f_{00}$ refers to the wild-type growth rate in the absence of drugs; and S corresponds to the degree of synergy, a parameter that determines a synergistic interaction for positive values and an antagonistic interaction for negative ones. Growth rates at different time points are determined by calculating the slope of the growth or kill curve being analyzed[18].

Measurement of ROS Production

The *E. coli* DHB4 cells were grown till the absorbance at $OD_{600\ nm}$ of 0.4 in LB medium, and the bacterial cells were treated with silver and antibiotics in combinations for 10 min. To analyze the amount of ROS production in the bacteria, cells were harvested by centrifugation at 6,000 rpm for 5 min and thoroughly washed 3 times with PBS, and stained with 5 µM $H_2DCF-DA$ for 20 min. After the incubation, cells were spun down and re-suspended in PBS, and the ROS production was quantified by flow cytometry (CyAnadp, Beckman coulter).

Measurement of $H_2O_2$ Production

The E. coli DHB4 cells were grown till the absorbance at $OD_{600\ nm}$ of 0.4 in LB medium, and the bacterial cells were treated with silver and antibiotics in combinations for 10 min. Cells were harvested by centrifugation at 6,000 rpm for 5 min and thoroughly washed 3 times with PBS, and sonicated for 10 s. In the presence of 50 μM Amplex® Red reagent, 0.1 U/mL HRP in 50 mM sodium phosphate buffer, pH 7.4, 50 μl samples were incubated for 30 minutes at room temperature protected from light and detected with absorbance at 560 nm (Molecular Probes, Eugene, Oreg.).

Measurement of Trx/TrxR Activities and GSH Amount in Antibiotics and Silver Treated E. coli Cell Lysates E. coli DHB4 cells were grown till the absorbance at $OD_{600\ nm}$ of 0.4 in LB medium, and the bacterial cells were treated with 80 μM antibiotics and 5 μM $AgNO_3$ for 10 and 60 min, respectively. The cultures treated with 80 μM ebselen and 5 μM $AgNO_3$ were used as the positive control. Cells were harvested by centrifugation at 6,000 rpm for 5 min and thoroughly washed 3 times with PBS, then cells were re-suspended in lysis buffer (25 mM Tris·HCl, pH 7.5, 100 mM NaCl, 2.5 mM EDTA, 2.5 mM EGTA, 20 mM NaF, 1 mM $Na_3VO_4$, 20 mM sodium ß-glycerophosphate, 10 mM sodium pyrophosphate, 0.5% Triton X-100) containing protease inhibitor cocktail and lysed by sonication. The cell lysates were obtained by centrifugation at 13,000 rpm for 20 min and the protein concentrations were measured by the Lowry protein assay.

E. coli DHB4 TrxR activity in cell extracts was measured by a DTNB reduction activity assay[23]. The experiments were performed with 96 micro-well plates in the solution containing 50 mM Tris·HCl (pH 7.5), 200 μM NADPH, 1 mM EDTA, 1 mM DTNB, in the presence of 5 μM E. coli Trx1. The absorbance at 412 nm was measured for 5 min with a VERSA micro-well plate reader and the slope of initial 2 min was used to represent TrxR activity. The Trx activity was detected by this method coupled with 100 nM E. coli TrxR instead of 5 μM E. coli Trx in the reaction mixture. To measure GSH levels, 25 μg of the cell lysates was added in the solution containing 50 nM GR, 50 mM Tris·HCl (pH 7.5), 200 μM NADPH, 1 mM EDTA, 1 mM DTNB. The absorbance at 412 nm was measured for 5 min.

Trx1 Redox State in E. coli Treated by Silver and Antibiotics in Combinations

E. coli DHB4 cells were grown till the absorbance at $OD_{600\ nm}$ of 0.4 in LB medium, and the bacterial cells were treated with 80 μM antibiotics and 5 μM $AgNO_3$ for 10 and 60 min, respectively. The cultures treated with 80 μM ebselen and 5 μM $AgNO_3$ were used as the positive control. Western blotting was performed to detect the Trx1 redox state of the treated E. coli cells. The cells were harvested by centrifugation at 6,000 rpm for 5 min and thoroughly washed 3 times with PBS, and precipitated the protein with 5% TCA in 1.0 ml. The precipitates were washed with 1 ml pre-ice-cold acetone for 3 times and dissolved in 50 mM Tris·HCl (pH 8.5) with 0.5% SDS containing 15 mM MeO-PEG-Mal at 37° C. for 2 h. Proteins were obtained by centrifugation at 13,000 rpm for 20 min to remove the pellets, and the protein concentration was measured by the Lowry protein assay. Proteins were incubated with SDS-loading buffer at 90° C. for 10 min, and then separated on the 4-12% bolt Bis-Tris gel with MES running buffer (150 V, 40 min). The redox state of Trx1 was detected with sheep anti-E. coli Trx1 antibody at 1:1000 dilution, followed by the detection of Chemiluminescence Reagent Plus.

Proteins S-Glutathionylation in E. coli Treated by Silver and Antibiotics in Combinations Total protein S-glutathionylation of antibiotics and $AgNO_3$ in combinations treated E. coli cells were also detected by Western blotting. E. coli DHB4 cells were grown till the absorbance at $OD_{600\ nm}$ of 0.4 in LB medium, and the bacterial cells were treated with 80 μM antibiotics and 5 μM $AgNO_3$ for 10 and 60 min, respectively. The cultures treated with 80 μM ebselen and 5 μM $AgNO_3$ were used as the positive control. Cells were washed 3 times, and re-suspended in lysis buffer (25 mM Tris·HCl, pH 7.5, 100 mM NaCl, 2.5 mM EDTA, 2.5 mM EGTA, 20 mM NaF, 1 mM $Na_3VO_4$, 20 mM sodium ß-glycerophosphate, 10 mM sodium pyrophosphate, 0.5% Triton X-100, protease inhibitor cocktail) containing 50 mM IAM. After lysed by sonication, the cell lysates were obtained by centrifugation at 13,000 rpm for 20 min. Protein concentration was measured by Lowry protein assay, and Western blotting assay was performed as described above with IgG2a mouse monoclonal antibody (VIROGEN, 101-A/D8) for S-glutathione-protein complexes.

Antibacterial Effects of Antibiotics and Silver on the Growth of Clinical Isolated MDR Gram-Negative Bacteria Five clinical isolated MDR Gram-negative strains were grown until an $OD_{600\ nm}$ of 0.4, and were diluted 1:1,000 into 100 μl LB medium in 96 micro-well plates. Serial dilutions of 100 μl antibiotics (0, 1, 2, 4 μM) and $AgNO_3$ (0, 1.25, 2.5, 5, 10, 20, 40, 80, 160 μM) in combinations were added to the individual wells. The MIC was determined after 16 h culture at 37° C. The cultures treated with the same serial dilutions of 100 μl ebselen and silver nitrate were used as the positive control.

Statistical Analysis

Mean, Standard Deviation (SD) and t-test (two tails, unpaired) significances were calculated in Grap Pad Prism Software. *: $p<0.05$, : $p<0.01$, *: $p<0.001$.

TABLE 1

MIC of Silver (μM) in the presence of ebselen against different multidrug-resistant Gram-negative species

| Ebselen | MIC of silver (μM) in the presence of ebselen against multidrug-resistant Gram-negative species | | | | | | | | | | Others | | |
|---|---|---|---|---|---|---|---|---|---|---|---|---|---|
| (μM) | KP-1 | KP-2 | AB-1 | AB-2 | PA-1 | PA-2 | ECL-1 | ECL-2 | ECO-1 | ECO-2 | ECO-3 | ECO-4 |
| 0 | 80 | 80 | 80 | 80 | 80 | 80 | 80 | 80 | 40 | 80 | 40 | 40 |
| 1 | 80 | 40 | 80 | 80 | 80 | 80 | 40 | 40 | 20 | 80 | 40 | 20 |

TABLE 1-continued

MIC of Silver (μM) in the presence of ebselen against different multidrug-resistant Gram-negative species

| Ebselen (μM) | MIC of silver (μM) in the presence of ebselen against multidrug-resistant Gram-negative species | | | | | | | | | | Others | | |
|---|---|---|---|---|---|---|---|---|---|---|---|---|---|
| | KP-1 | KP-2 | AB-1 | AB-2 | PA-1 | PA-2 | ECL-1 | ECL-2 | ECO-1 | ECO-2 | ECO-3 | ECO-4 | |
| 2 | 40 | 20 | 40 | 40 | 20 | 40 | 20 | 40 | 10 | 40 | 20 | 10 | |
| 4 | 10 | 20 | 10 | 20 | 20 | 20 | 20 | 10 | 5 | 10 | 10 | 5 | |

KP-1: Klebsiella pneumoniae (K. pneumoniae) subsp. pneumoniae 13#; KP-2: K. pneumoniae subsp. pneumoniae 0322#; AB-1: Acinetobacter baumannii (A. baumannii) H#; AB-2: A. baumannii 0361#; PA-1: Pseudomonas aeruginosa (P. aeruginosa) 1298#; PA-2: P. aeruginosa 0009#; ECL-1: Enterobacter cloacae (E. cloacae) 0431#; ECL-2: E. cloacae 2301#; ECO-1: Escherichia coli (E. coli) 1139#; ECO-2: E. coli 2219#; ECO-3: E. coli ZY-1; ECO-4: MG1655 (ATCC 700926).

TABLE 2

Clinical isolated multidrug-resistant Gram-negative strains

| Strain | Description |
|---|---|
| KP-1 | Klebsiella pneumonia (K. pneumonia) subsp. pneumonia 13# |
| KP-2 | K. pneumonia subsp. pneumonia 0322# |
| AB-1 | Acinetobacter baumannii (A. baumannii) H# |
| AB-2 | A. baumannii 0361# |
| PA-1 | Pseudomonas aeruginose (P. aeruginose) 1298# |
| PA-2 | P. aeruginose 0009# |
| ECL-1 | Enterobacter cloacae (E. cloacae) 0431# |
| ECL-2 | E. cloacae 2301# |
| ECO-1 | Escherichia coli (E. coli) 1139# |
| ECO-2 | E. coli 2219# |
| WZ11 | E. coli ZY-1 |
| MG1655 | ATCC 700926 |

TABLE 3

Drug sensitivity of clinical isolated multidrug-resistant Gram-negative strains

| Antibiotic | KP-1 | KP-2 | AB-1 | AB-2 | PA-1 | PA-2 | ECL-1 | ECL-2 | ECO-1 | ECO-2 | ECO-3 |
|---|---|---|---|---|---|---|---|---|---|---|---|
| Amikacin | R | S | R | R | S | R | S | S | S | S | S |
| Ampicillin | R | R | R | R | R/S | R | / | / | S | R | S |
| Aztreonam | R | R | R | R | R | R | R | R | R | R | S |
| Cefazolin | R | R | R | R | R | R | / | / | R | R | S |
| Cefepime | R | R | R | R | R | R | R | R | R | R | S |
| Cefotaxime | R | R | R | R | R | R | R | R | R | R | S |
| Ceftazidime | R | R | R | R | R | R | R | R | R/S | R | S |
| Chloramphenicol | R | R | R | R | / | R | R | R | S | S | S |
| Ciprofloxacin | R | R | R | R | R | R | R | R | R | R | R |
| Gentamicin | R | R | R | R | S | R | R | R | S | R | S |
| Imipenem | R | S | R | R | S | / | S | R | S | S | S |
| Levofloxacin | R | R | R | R | R | R | R | R | R | R | / |
| Meropenem | R | S | R | R | R | R/S | S | R | S | S | S |
| Piperacillin | R | R | R | R | R/S | R | R | R | R | R | S |
| Polymyxin | / | / | S | S | S | S | R | S | / | / | / |
| Sulbactam | R | R | R | / | / | / | / | / | R/S | R | S |
| Sulfanilamide | S | R | / | S | R | R | R | R | R | R | R |
| Tazobactam | R | R | R | R | R/S | R | S | R | S | R/S | S |
| Tetracycline | S | R | R | R | R | R | R | R | R | S | S |

*R: resistant; S: sensitive.

TABLE 4

MIC of silver (μM) in the presence of ebselen against E. coli DHB4 mutants

| Ebselen (μM) | MIC of silver (μM) in the presence of ebselen against Escherichia coli DHB4 redox mutants | | | | | | | | | | |
|---|---|---|---|---|---|---|---|---|---|---|---|
| | WT | trxA⁻ | trxB⁻ | trxC⁻ | trxA⁻B⁻C⁻ | oxyR⁻ | gshA⁻ | trxA⁻gshA⁻ | gor⁻ | gor⁻grxA⁻B⁻C⁻ | grxA⁻trxA⁻ |
| 0 | 40 | 40 | 40 | 40 | 40 | 20 | 20 | 20 | 40 | 20 | 20 |
| 1 | 10 | 10 | 10 | 10 | 10 | 5 | 5 | 5 | 10 | 10 | 10 |
| 2 | 5 | 2.5 | 2.5 | 5 | 2.5 | 1.25 | 2.5 | 2.5 | 5 | 2.5 | 2.5 |
| 4 | 1.25 | 1.25 | 0.625 | 1.25 | 1.25 | 0.625 | 0.625 | 0.625 | 1.25 | 0.625 | 0.625 |

TABLE 5

MIC of ebselen (μM) in the presence of silver against E. coli DHB4 mutants

MIC of ebselen (μM) in the presence of ebselen against Escherichia coli DHB4 redox mutants

| Silver (μM) | WT | trxA⁻ | trxB⁻ | trxC⁻ | trxA⁻ B⁻C⁻ | oxyR⁻ | gshA⁻ | trxA⁻ gshA⁻ | gor⁻ | gor⁻grxA⁻ B⁻C⁻ | grxA⁻ trxA⁻ |
|---|---|---|---|---|---|---|---|---|---|---|---|
| 0 | 80 | 80 | 80 | 80 | 80 | 40 | 40 | 40 | 80 | 40 | 40 |
| 0.625 | 8 | 8 | 8 | 8 | 8 | 4 | 4 | 4 | 8 | 8 | 8 |
| 1.25 | 4 | 4 | 2 | 4 | 4 | 2 | 2 | 2 | 4 | 2 | 2 |
| 2.5 | 4 | 2 | 2 | 4 | 2 | 2 | 2 | 2 | 2 | 2 | 2 |
| 5 | 2 | 1 | 1 | 2 | 1 | 1 | 1 | 1 | 1 | 1 | 1 |
| 10 | 1 | 1 | 0.5 | 1 | 0.5 | 0.5 | 0.5 | 0.5 | 1 | 0.5 | 0.5 |
| 20 | 0.5 | 0.5 | 0.5 | 0.5 | 0.5 | 0 | 0 | 0 | 0.5 | 0 | 0 |
| 40 | 0 | 0 | 0 | 0 | 0 | 0 | 0 | 0 | 0 | 0 | 0 |

TABLE 6

Escherichia coli DHB4 redox phenotypes

| Strain | Genotype |
|---|---|
| Wild type | DHB4 (F' lac-pro lacI^Q/Δ(ara-leu)7697 araD139 ΔlacX74 galE galK rpsL phoR Δ(phoA)PvuII ΔmalF3 thi) |
| trxA⁻ | DHB4 ΔtrxA |
| trxB⁻ | DHB4 trxB::Kan |
| trxC⁻ | DHB4 ΔtrxC |
| trxA⁻trxB⁻trxC⁻ | DHB4 ΔtrxA ΔtrxC trxB::Kan nadB::Tn |
| oxyR⁻ | DHB4 oxyR::Kan |
| gshA⁻ | DHB4 gshA20::Kan |
| trxA⁻gshA⁻ | DHB4 ΔtrxA gshA20::Kan |
| gor⁻ | DHB4 gor522 ... mini-Tn10Tc |
| gor⁻grxA⁻B⁻C⁻ | DHB4 gor522gxA::Kan grxB::Kan mini-Tn10Tc grxC::Cm |
| grxA⁻trxA⁻ | DHB4 ΔtrxA grxA::Kan |

TABLE 7

Drug sensitivity of clinical isolated E. coli ZY-1

| Antibiotic | ZY-1 |
|---|---|
| Amikacin | S |
| Ampicillin | S |
| Aztreonam | S |
| Cefazolin | S |
| Cefepime | S |
| Cefotaxime | S |
| Ceftazidime | S |
| Chloramphenicol | S |
| Ciprofloxacin | S |
| Gentamicin | S |
| Imipenem | S |
| Levofloxacin | S |
| Meropenem | S |
| Piperacillin | S |
| Polymyxin | / |
| Sulbactam | S |
| Sulfanilamide | R |
| Tazobactam | S |
| Tetracycline | R |

TABLE 8

Analysis of blood samples from mice treatment with or without silver and ebselen

| | Vehicle | | | Ebselen + Ag | | | PBS | | |
|---|---|---|---|---|---|---|---|---|---|
| | 6h | 24h | 48h | 6h | 24h | 48h | 6h | 24h | 48h |
| ALT (U/L) | 32.7 ± 9.3 | 24.0 ± 3.6 | 25.33 ± 4.0 | 79.0 ± 41.0 | 31.7 ± 6.4 | 25.8 ± 5.62 | 28.7 ± 6.4 | 25.3 ± 7.2 | 28.3 ± 17.0 |
| AST (U/L) | 130.7 ± 46.6 | 108.0 ± 5.0 | 106.67 ± 38.1 | 300.7 ± 15 | 145.3 ± 28.6 | 102.5 ± 53.4 | 113.3 ± 6.0 | 110.3 ± 23.5 | 88.7 ± 7.0 |
| BUN (mmol/L) | 5.3 ± 1.14 | 5.9 ± 0.93 | 6.74 ± 2.0 | 6.0 ± 0.71 | 6.53 ± 0.8 | 5.74 ± 0.5 | 4.6 ± 0.8 | 7.2 ± 0.6 | 5.8 ± 1.5 |
| CRE (μmol/L) | 29.3 ± 2.52 | 37.7 ± 1.53 | 29.7 ± 2.08 | 23.0 ± 1.7 | 39.0 ± 2.6 | 30.0 ± 5.5 | 23.0 ± 3.5 | 26.7 ± 2.3 | 28.3 ± 5.9 |
| TBIL (μmol/L) | 0.10 ± 0.17 | 0 | 0 | 0.43 ± 0.40 | 0 | 0 | 0.40 ± 0.5 | 0 | 0 |
| WBC ($10^9$/L) | 3.29 | 2.52 | 3.50 | 4.36 | 3.27 | 2.21 | 3.12 | 3.13 | 2.38 |
| Neu# ($10^9$/L) | 1.46 | 0.69 | 0.84 | 2.69 | 1.20 | 0.52 | 0.82 | 0.90 | 0.55 |
| Lym# ($10^9$/L) | 1.72 | 1.72 | 2.57 | 0.07 | 2.39 | 1.57 | 2.2 | 1.98 | 1.78 |
| Mon# ($10^9$/L) | 0.07 | 0.05 | 0.03 | 1.57 | 0.05 | 0.01 | 0.02 | 0.06 | 0.04 |
| Eos# ($10^9$/L) | 0.02 | 0.06 | 0.06 | 0.03 | 0.07 | 0.01 | 0.08 | 0.18 | 0.01 |
| Bas# ($10^9$/L) | 0.02 | 0 | 0 | 0 | 0.01 | 0 | 0 | 0.01 | 0 |
| IMG# ($10^9$/L) | 0 | 0 | 0.01 | 0.02 | 0.01 | 0 | 0 | 0.04 | 0 |
| Neu % (%) | 44.3 | 27.3 | 24.1 | 61.7 | 32.2 | 23.5 | 26.3 | 28.7 | 23.3 |
| Lym % (%) | 52.3 | 68.4 | 73.3 | 1.6 | 64.5 | 75.3 | 70.4 | 63.4 | 74.5 |
| Mon % (%) | 2 | 2 | 0.9 | 35.9 | 1.3 | 0.5 | 0.6 | 1.9 | 1.7 |
| Eos % (%) | 0.7 | 2.2 | 1.7 | 0.7 | 1.8 | 0.5 | 2.6 | 5.7 | 0.4 |
| Bas % (%) | 0.7 | 0.1 | 0 | 0.1 | 0.2 | 0.2 | 0.1 | 0.3 | 0.1 |
| IMG % (%) | 0 | 0.1 | 0.2 | 0.3 | 0.3 | 0.1 | 0 | 1.4 | 0 |
| PLT ($10^9$/L) | 574 | 912 | 956 | 566 | 602 | 744 | 605 | 187 | 928 |
| MPV (fL) | 7.7 | 6.7 | 6.5 | 7.3 | 7.1 | 6.1 | 7.0 | 7.9 | 6.1 |
| PDW | 14.8 | 14.8 | 14.7 | 14.9 | 15 | 14.7 | 15 | 15.4 | 14.6 |
| PCT (%) | 0.442 | 0.613 | 0.62 | 0.413 | 0.428 | 0.456 | 0.422 | 0.147 | 0.566 |

TABLE 8-continued

Analysis of blood samples from mice treatment with or without silver and ebselen

| | Vehicle | | | Ebselen + Ag | | | PBS | | |
|---|---|---|---|---|---|---|---|---|---|
| | 6h | 24h | 48h | 6h | 24h | 48h | 6h | 24h | 48h |
| P-LCC ($10^9$/L) | 76 | 72 | 65 | 66 | 61 | 39 | 62 | 37 | 48 |
| P-LCR (%) | 13.2 | 7.9 | 6.8 | 11.7 | 10.1 | 5.3 | 10.3 | 19.7 | 5.1 |
| RBC ($10^{12}$/L) | 9.26 | 8.56 | 8.35 | 7.95 | 7.25 | 8.21 | 8.31 | 8.91 | 7.79 |
| HGB (g/L) | 145 | 129 | 127 | 124 | 112 | 130 | 133 | 141 | 122 |
| HCT (%) | 48.7 | 43.3 | 42 | 41.8 | 38 | 44.8 | 44.6 | 46.6 | 41.2 |
| MCV (fL) | 52.7 | 50.6 | 50.3 | 52.5 | 52.4 | 54.5 | 53.7 | 52.3 | 52.8 |
| MCH (pg) | 15.77 | 15.1 | 15.2 | 15.6 | 15.5 | 15.9 | 16.0 | 15.8 | 15.6 |
| MCHC (g/L) | 297 | 299 | 301 | 298 | 296 | 291 | 297 | 302 | 296 |
| RDW-CV (%) | 18.1 | 18.2 | 18.1 | 20.2 | 16.3 | 21.6 | 17.8 | 21.2 | 18.1 |
| RDW-SD (fL) | 33.2 | 31.9 | 32.0 | 36.7 | 29.5 | 41.1 | 33.3 | 38.7 | 33.5 |

*ALT: alanine transaminase; AST: aspartate aminotransferas; BUN: blood urea nitrogen; CRE: Creatinine; TBIL: total bilirubin; WBC: white blood cell count; Neu: neutrophil; Lym: lymphocyte; Mon: monocyte; Eos: eosinophil; Bas: basophil; IMG: immunoglobulin; PLT: platelets; MPV: mean platelet volume; PDW: platelet distribution width; PCT: plateletocrit; P-LCC: large platelet count; P-LCR: large platelet ratio; RBC: red bllod cell count; HGB: hemoglobin; HCT: hematocrit; MCV: mean corpuscular volume; MCH: mean corpuscular hemoglobin; MCHC: mean corpuscular hemoglobin concentration; RDW-CV: red cell distribution width coefficient of variation; RDW-SD: red cell distribution width standard deviation. Data are means ± s. d. of three independent experiments.

TABLE 9

Antibacterial effect as MIC of nine antibiotics and silver on wild type *E. coli* DHB4

| Silver | Beta-lactams | | Aminoglycosides | | | | Tetracycline | Macrolides | Synthesis | Control |
|---|---|---|---|---|---|---|---|---|---|---|
| (µM) | Amp | Car | Genta | Strep | Gene | Kana | Tetra | Ery | Chlor | Ebse |
| 0 | 40 | 40 | 40 | / | 40 | 40 | 40 | 40 | 40 | 40 |
| 1 | 40 | 40 | 20 | / | 40 | 20 | 20 | 40 | 40 | 10 |
| 2 | 40 | 40 | 2.5 | / | 10 | 2.5 | 10 | 40 | 40 | 5 |
| 4 | 40 | 40 | 1.25 | 40 | 2.5 | 1.25 | 1.25 | 40 | 40 | 1.25 |

Ampiciline: Amp; Carbenicillin: Car; Gentamycin: Genta; Streptomycin: Strep; Geneticin: Gene; Kanamycin: Kana; Tetracycline: Tetra; Erythromycin: Ery;Chloramphenicol: Chlo; Ebse: Ebselen. Streptomycin: 4 + 40, 8 + 40, 16 + 40, no synergistic effect.

TABLE 10

MIC of silver (µM) in the presence of different antibiotics against MDR Gram-negative bacteria

| Antibiotics | Multi-drug Resistant Gram-negative Strains | | | | |
|---|---|---|---|---|---|
| (4 µM) | KP-2 | AB-1 | PA-1 | ECL-2 | ECO-1 |
| Genta | 160 | 80 | 40 | 160 | 40 |
| Kana | 160 | 80 | 80 | 160 | 40 |
| Gene | 160 | 80 | 80 | 160 | 40 |
| Tetra | 160 | 80 | 80 | 160 | 80 |
| Ebse | 40 | 10 | 20 | 10 | 5 |

What is claimed is:

1. A non-biological surface coated with an antibiotic composition, wherein: the antibiotic composition comprises a metal-containing agent, which comprises silver, and an organoselenium agent that
comprises ebselen or ebselen diselenide,
and the antibiotic composition is present in an amount effective for killing or inhibiting one or more bacteria when the one or more bacteria contact the non-biological surface.

2. The non-biological surface of claim 1, wherein the metal-containing agent further comprises copper, zinc, mercury, tin, lead, bismuth, cadmium, cerium, chromium, thallium, or any combination thereof.

3. The non-biological surface of claim 1, wherein the metal-containing agent comprises silver nitrate.

4. The non-biological surface of claim 1, wherein the silver is silver nitrate, silver acetate, silver benzoate, silver carbonate, silver iodate, silver iodide, silver lactate, silver laurate, silver oxide, silver palmitate, silver protein, silver sulfadiazine, or any combination thereof.

5. A method of making the non-biological surface of claim 1, the method comprising coating the non-biological surface with the antibiotic composition comprising the metal-containing agent comprising silver and the organoselenium agent comprising ebselen or ebselen diselenide.

6. The non-biological surface of claim 1, wherein the non-biological surface is a surgical equipment surface.

7. The non-biological surface of claim 1, wherein the non-biological surface is on or in a joint prosthesis, a dental implant, a catheter, or a cardiac implant.

8. The non-biological surface of claim 1, wherein the organoselenium agent is ebselen.

9. The non-biological surface of claim 1, wherein the organoselenium agent is ebselen diselenide.

10. The non-biological surface of claim 1, wherein the metal-containing agent comprising silver and the organoselenium agent are present in a molar ratio ranging from about 1:2 to about 1:20.

11. The non-biological surface of claim 10, wherein the metal-containing agent comprising silver and the organoselenium agent are present in a molar ratio ranging from about: 1:4, 1:8, or 1:16.

12. The non-biological surface of claim 10, wherein the organoselenium agent is ebselen.

13. The non-biological surface of claim 10, wherein the organoselenium agent is ebselen diselenide.

14. The non-biological surface of claim 1, wherein the non-biological surface coated with the antibiotic composition exhibits an $IC_{50}$ value of about 50 nM or lower to one or more Gram-negative bacteria.

15. The non-biological surface of claim 14, wherein the one or more Gram-negative bacteria comprises *K. pneumonia, A. baumannii, P. aeruginosa, E. cloacae, E. coli*, or any combination thereof.

16. The non-biological surface of claim 14, wherein the organoselenium agent is ebselen.

17. The non-biological surface of claim 14, wherein the organoselenium agent is ebselen diselenide.

18. The method of claim 5, wherein the organoselenium agent is ebselen.

19. The method of claim 5, wherein the organoselenium agent is ebselen diselenide.

* * * * *